(12) United States Patent  
Anand-Apte

(10) Patent No.: US 8,431,396 B2
(45) Date of Patent: Apr. 30, 2013

(54) ANTI-ANGIOGENIC PEPTIDES

(75) Inventor: Bela Anand-Apte, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 27 days.

(21) Appl. No.: 12/529,650

(22) PCT Filed: Feb. 29, 2008

(86) PCT No.: PCT/US2008/055488
§ 371 (c)(1),
(2), (4) Date: Sep. 2, 2009

(87) PCT Pub. No.: WO2008/109433
PCT Pub. Date: Sep. 12, 2008

(65) Prior Publication Data
US 2010/0099611 A1    Apr. 22, 2010

Related U.S. Application Data

(60) Continuation-in-part of application No. 11/653,647, filed on Jan. 16, 2007, which is a division of application No. 10/804,937, filed on Mar. 19, 2004, now Pat. No. 7,183, 256.

(60) Provisional application No. 60/892,553, filed on Mar. 2, 2007, provisional application No. 60/456,768, filed on Mar. 21, 2003.

(51) Int. Cl.
C12N 5/07    (2010.01)
A61K 38/10   (2006.01)
A61K 38/18   (2006.01)

(52) U.S. Cl.
USPC ......... 435/375; 514/21.3; 514/21.4; 514/21.5

(58) Field of Classification Search .................. 435/375; 514/21.3, 21.4, 21.5
See application file for complete search history.

(56) References Cited

U.S. PATENT DOCUMENTS 7,183,256 B2 * 2/2007 Anand-Apte .................. 514/8.1
2002/0086420 A1  7/2002 Moses et al.

FOREIGN PATENT DOCUMENTS

| JP | 9-235300 A | 9/1997 |
| WO | WO-95/05478 A1 | 2/1995 |
| WO | WO-95/09918 A1 | 4/1995 |
| WO | WO 2004085617 A2 * | 10/2004 |
| WO | WO-2005/007090 A2 | 1/2005 |
| WO | WO-2007/033215 A2 | 3/2007 |

OTHER PUBLICATIONS

Supplementary search report issued by the European Patent Office dated Mar. 26, 2010, (11 pgs.), in Application No. EP08731118.

(Continued)

*Primary Examiner* — Rosanne Kosson
(74) *Attorney, Agent, or Firm* — Tarolli, Sundheim, Covell & Tummino LLP

(57) ABSTRACT

A purified polypeptide includes about 10 to about 40 amino acids and has an amino acid sequence corresponding to a portion of SEQ ID NO: 2. The polypeptide can inhibit binding of VEGF to VEGFR2 of cells that express VEGFR2.

1 Claim, 28 Drawing Sheets

Control (PBS)

N-Term peptide (10)    Tail peptide (10)    Loop 6 (10)    Loop 5 (10)

OTHER PUBLICATIONS

Abstract of Database UniProt dated Mar. 1, 2002 for Seuanez, H.N. et al.: "Tissue Inhibitor of Metalloproteinase 3", XP002572807 retrieved from EBI Database Accession No. Q8WP05, *100% indentity in 31 aa overlap of the sequence Q8WP05 (31 aa) with SEQ ID No. 2 (91aa) of the present application * & Chromosome Research, vol. 9, No. 8, 2001, pp. 631-639, ISSN: 0967-3849.

Abstract of Database UniProt dated Jun. 5, 2004 for Higuchi, T. et al.: TIM-3, XP002572808 retrieved from EBI Database Accession No. Q6IEP5 * 100% identity in 11 aa overlap of Q6LEP5 (11 aa) with SEQ ID No. 2 (91 aa) of the present application*.

Uria et al. "Structure and Expression in Breast Tumors of Human TIMP-3, a New Member of the Metalloproteinase Inhibitor Family", *Cancer Res.* 1994, vol. 54, pp. 2091-2094.

Qi et al., ARVO Annula Meeting Abstract Search and Program Planner, Abstract No. 2753, May 5-10, 2002.

Database NCBI Conserved Domain Search for Human TIMP3, printed on Oct. 28, 2005.

* cited by examiner

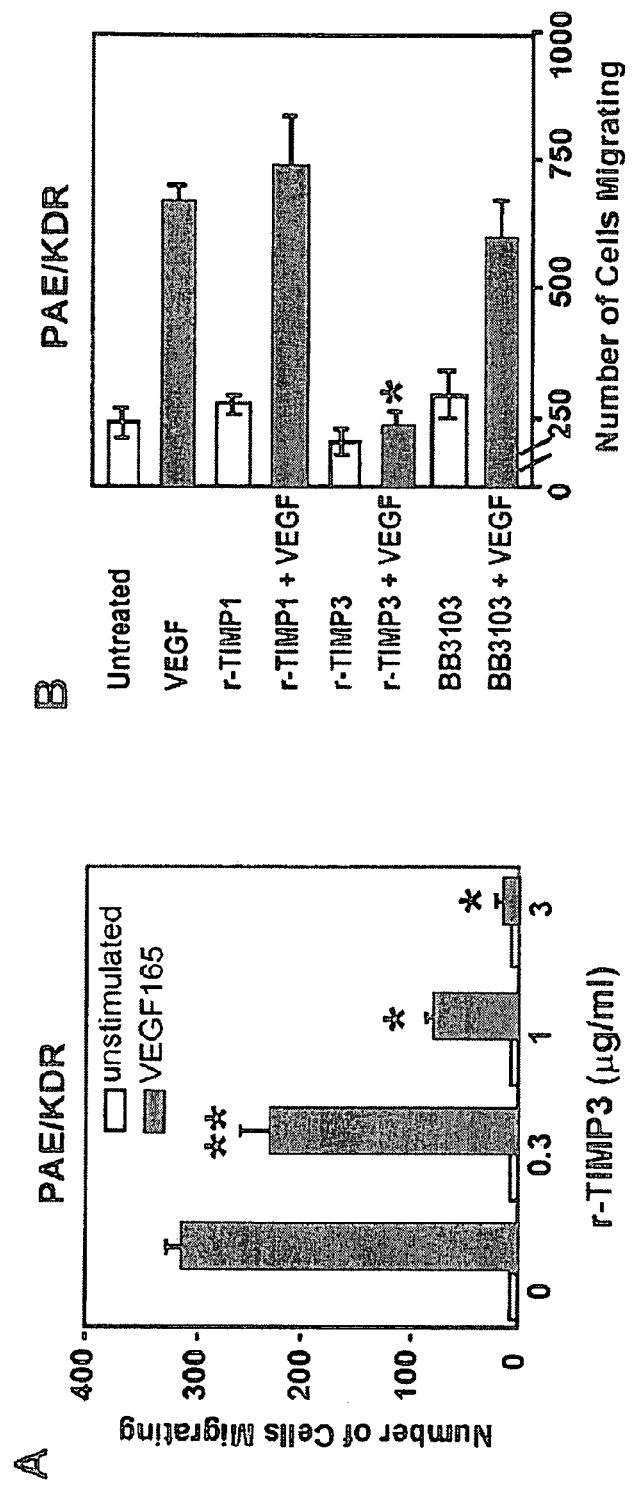
FIG. 2A-B

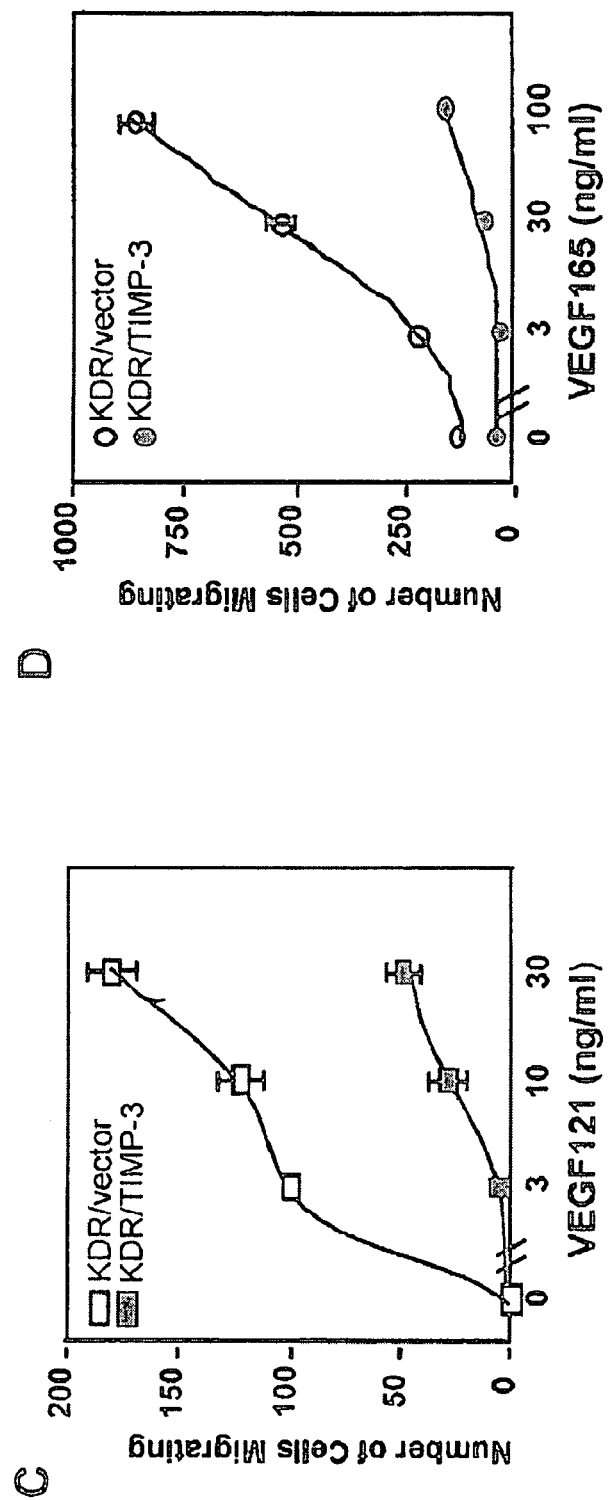
FIG. 2C-D

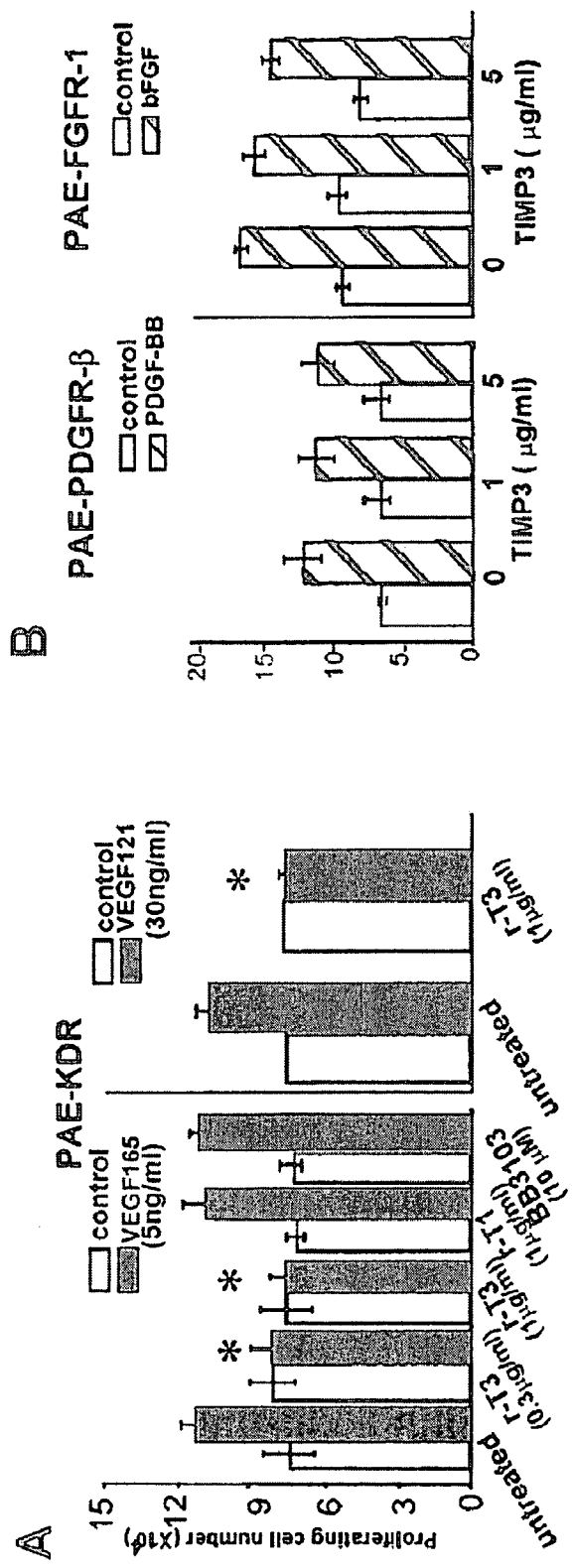
FIG. 3A-B

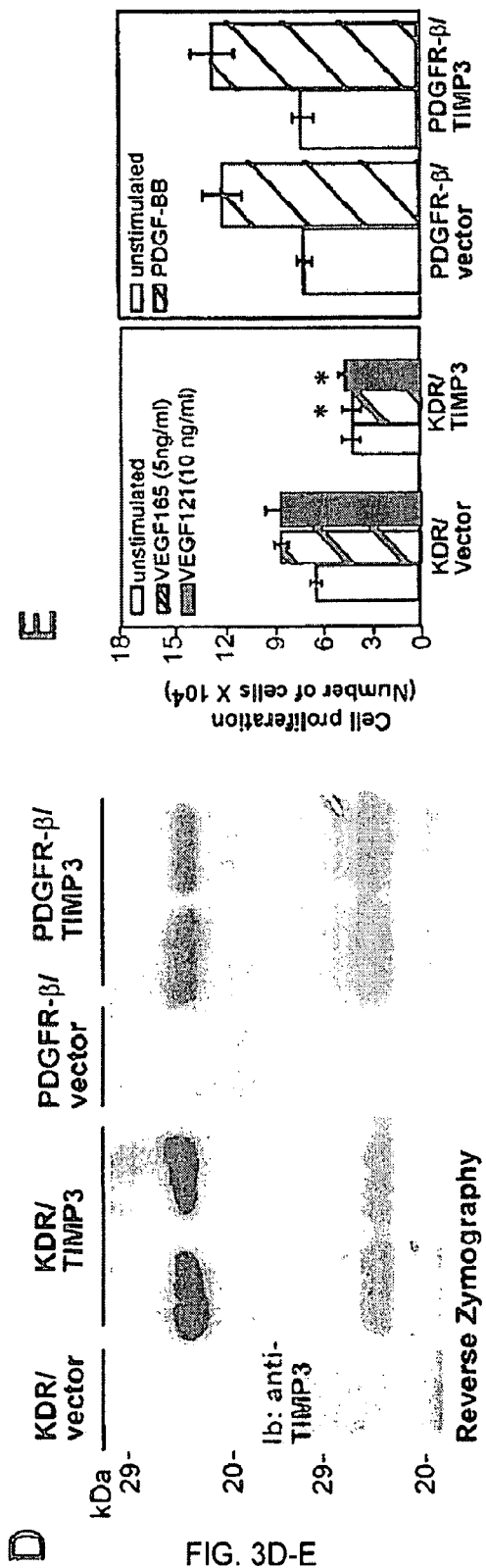
FIG. 3D-E

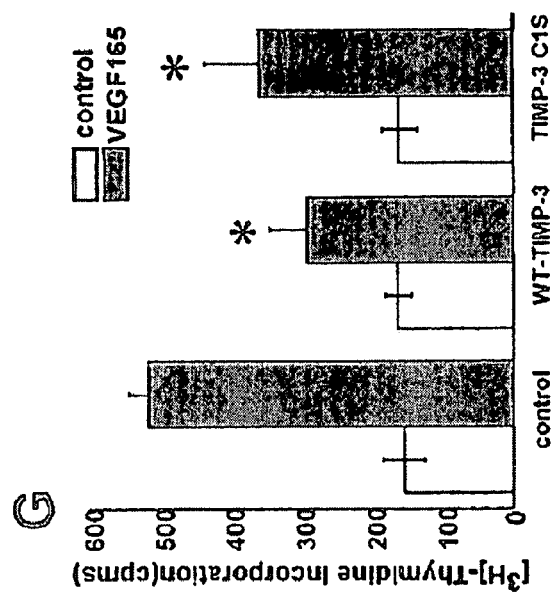
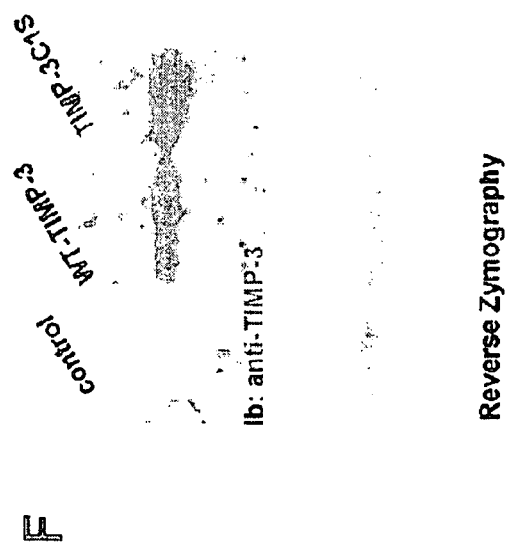
FIG. 3F-G

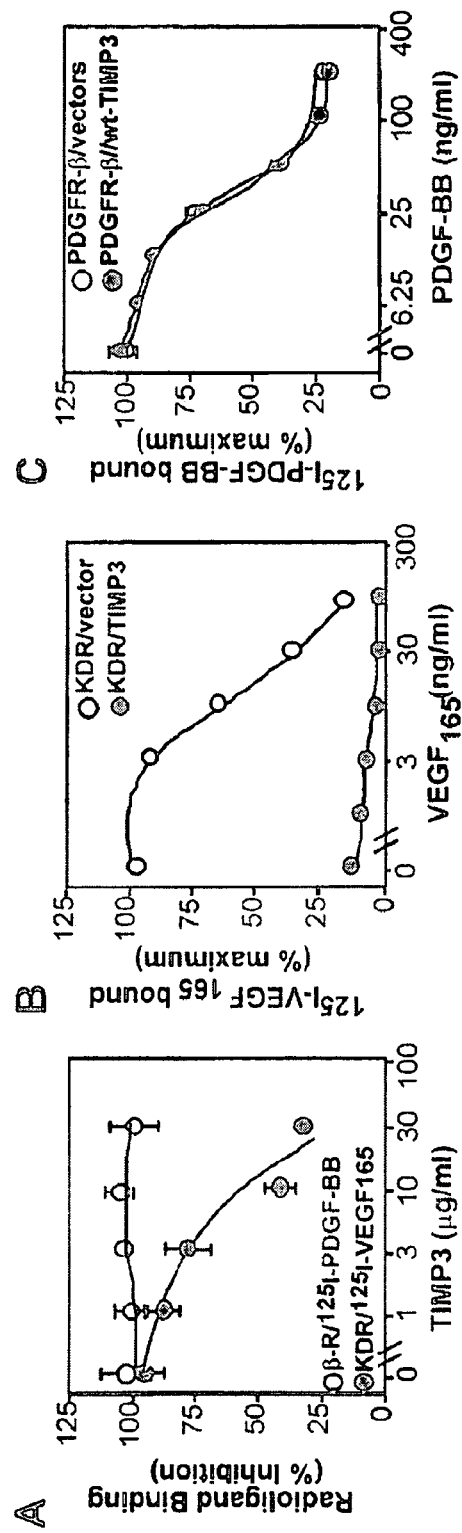
FIG. 5A-C

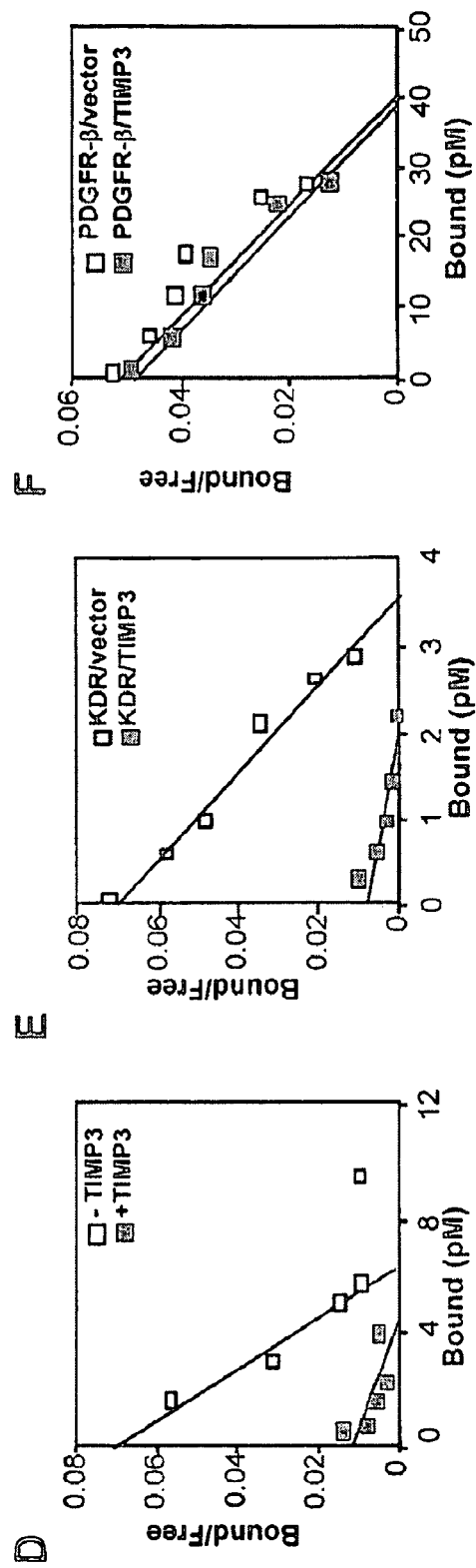
FIG. 5D-F

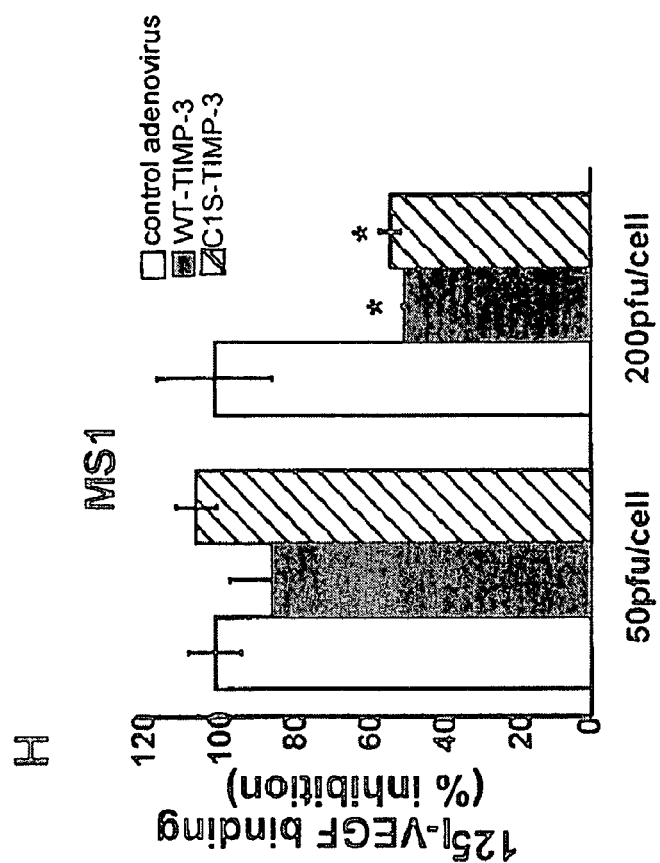
FIG. 5G-H

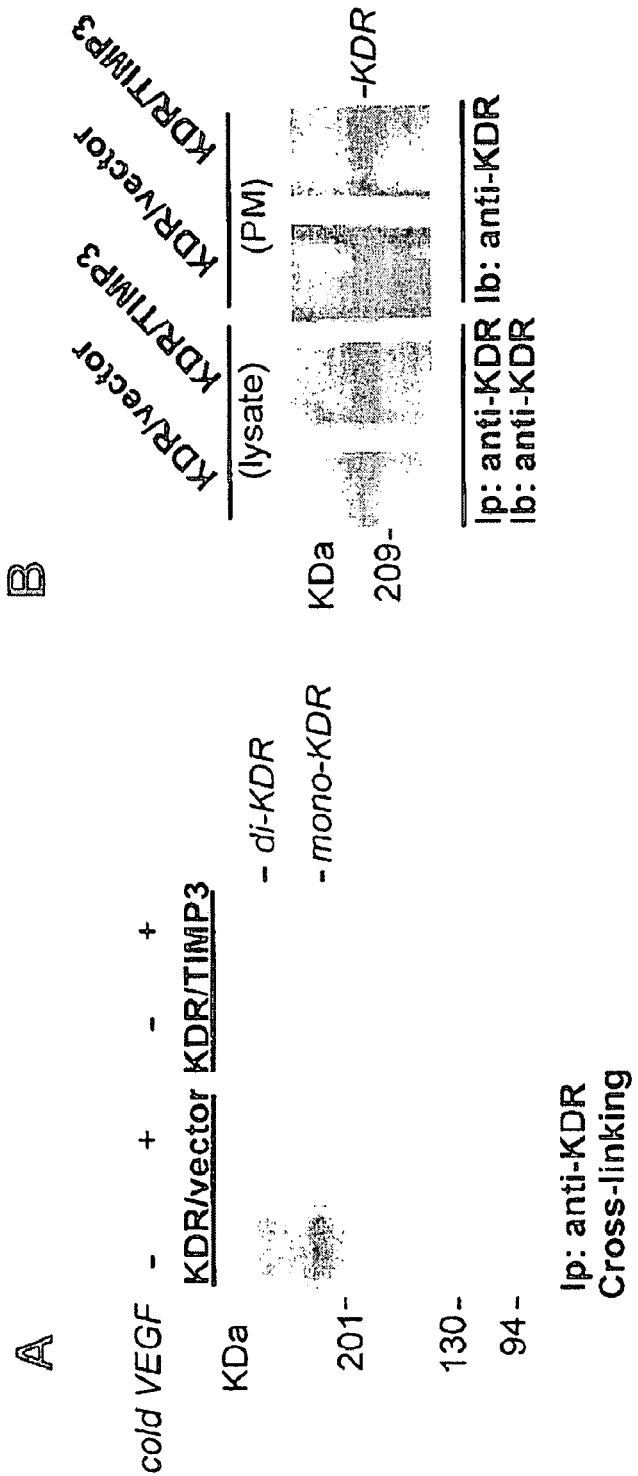
FIG. 6A-B

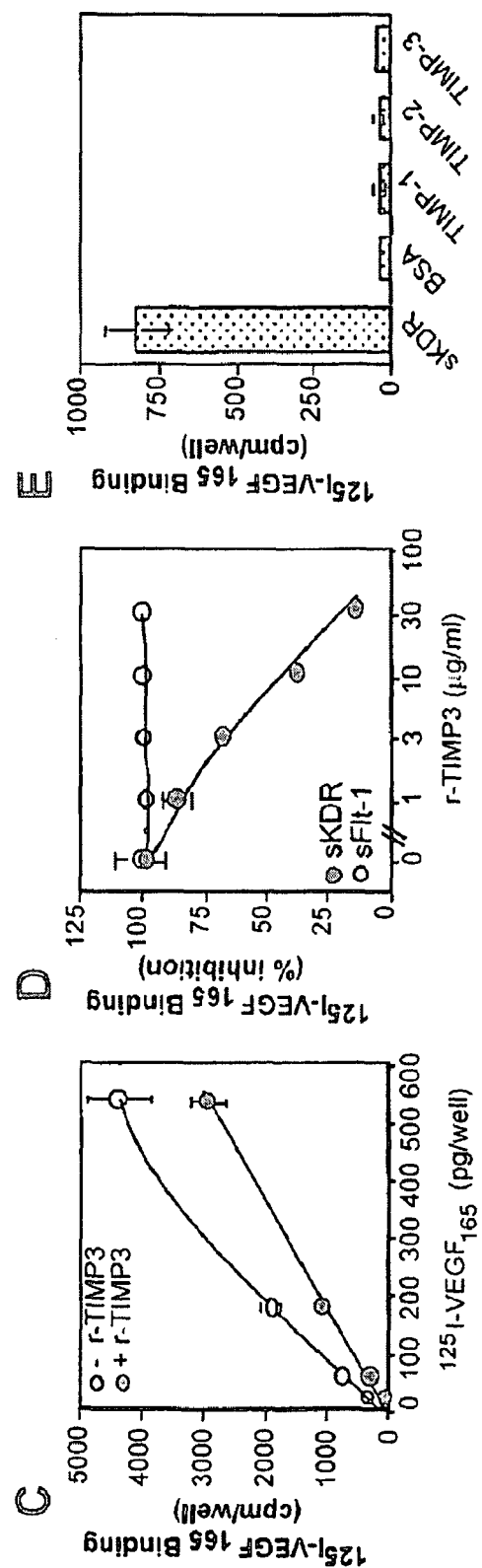
FIG. 6C-E

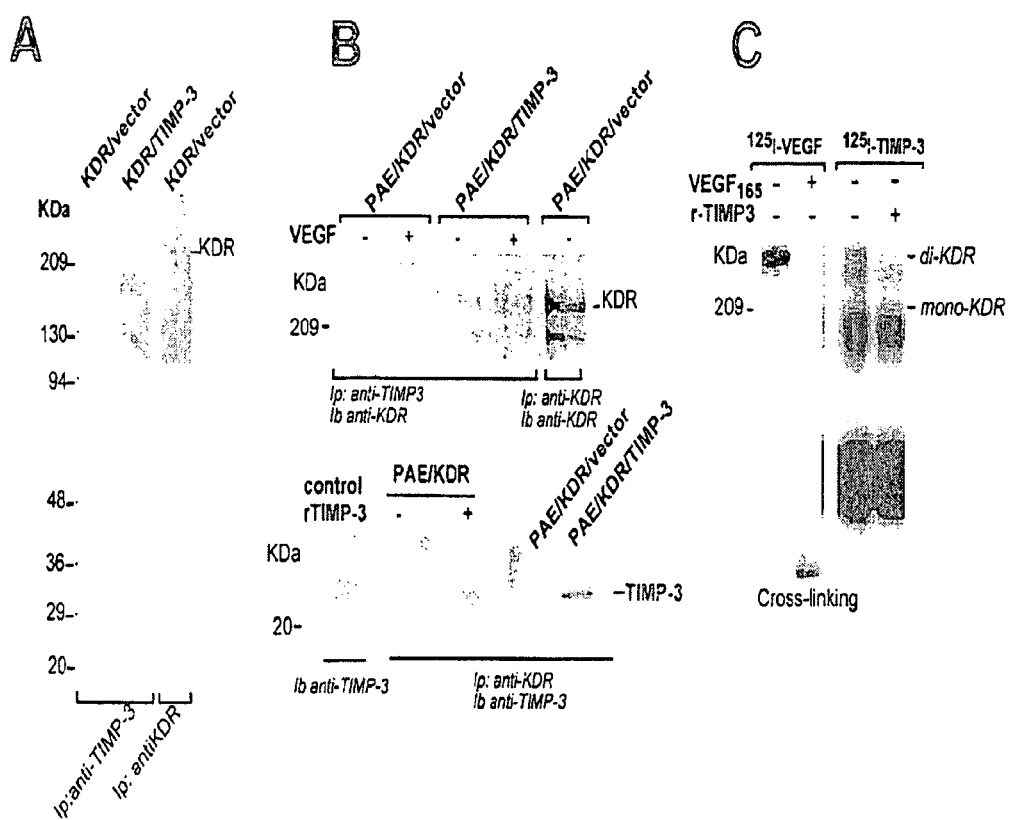
FIG. 7A-C

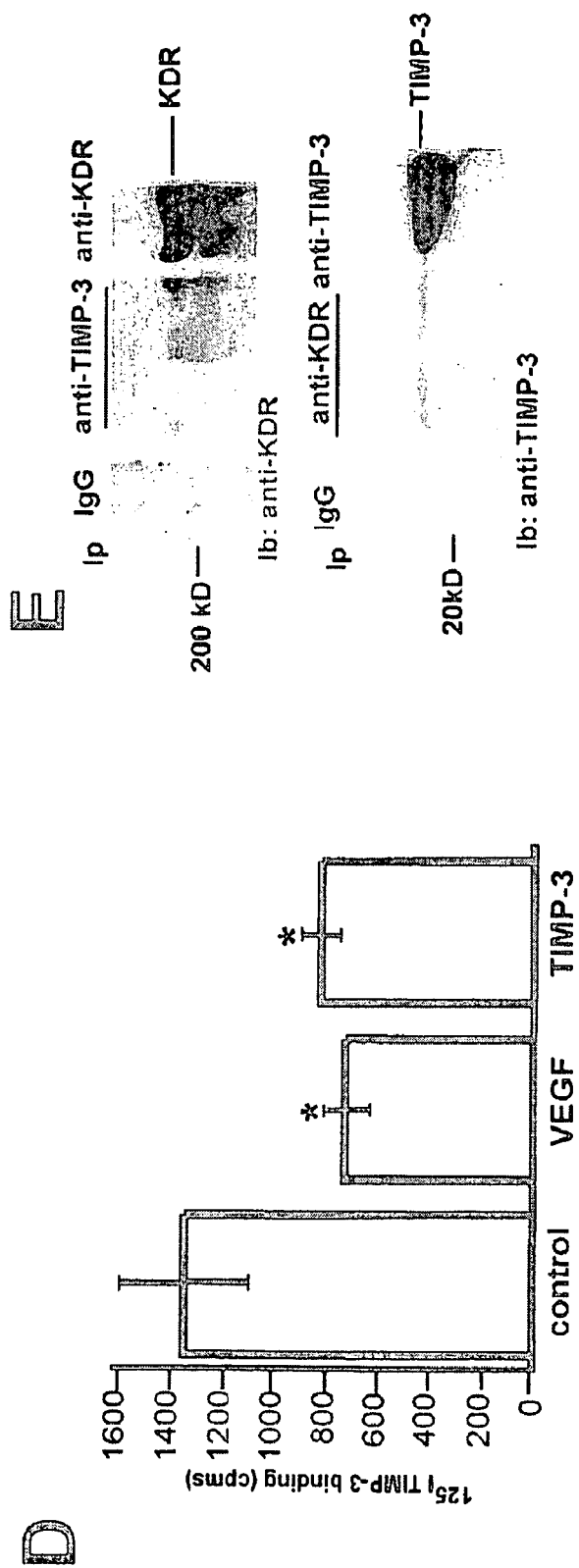
FIG. 7D-E

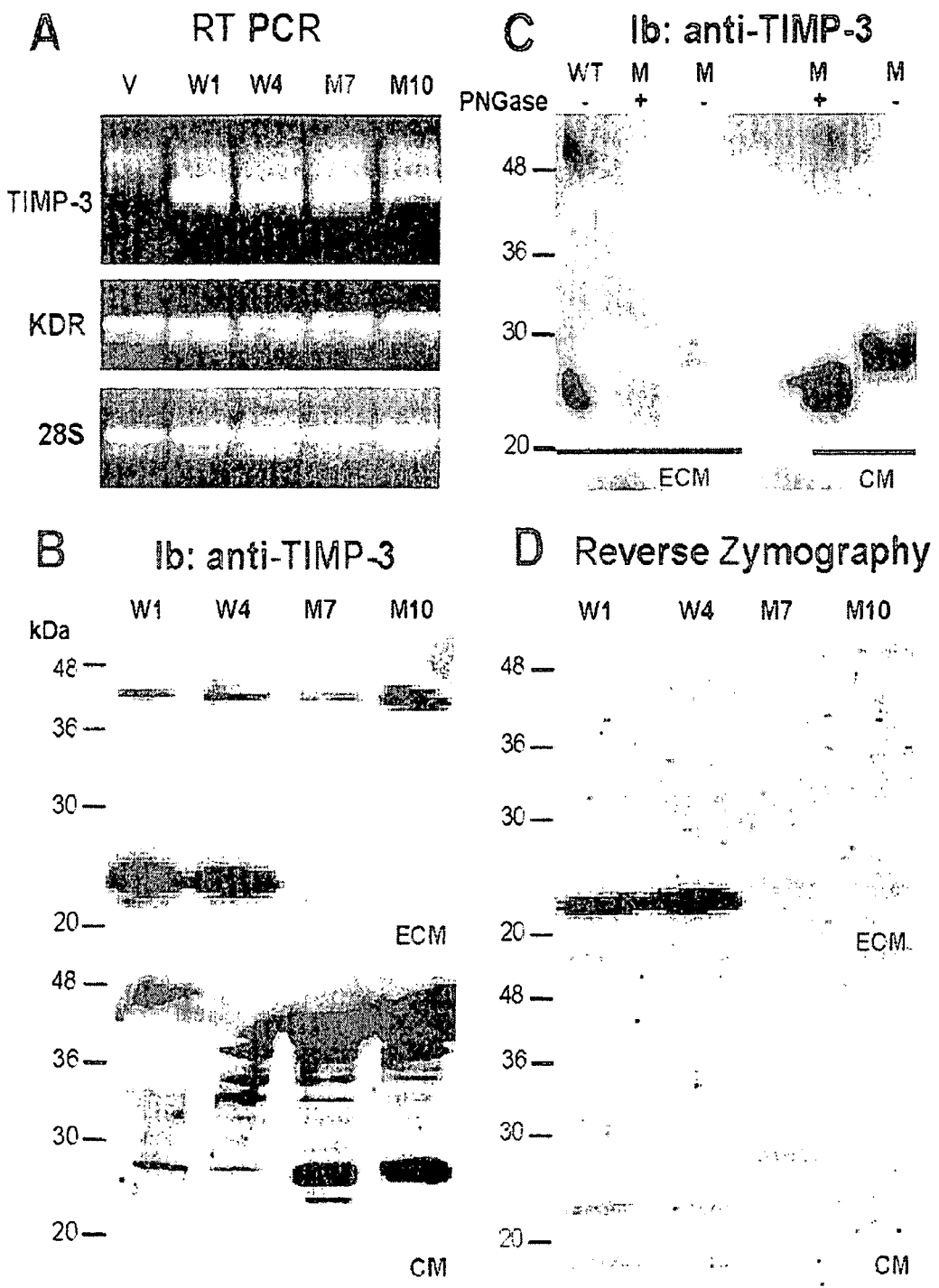
FIG. 13A-D

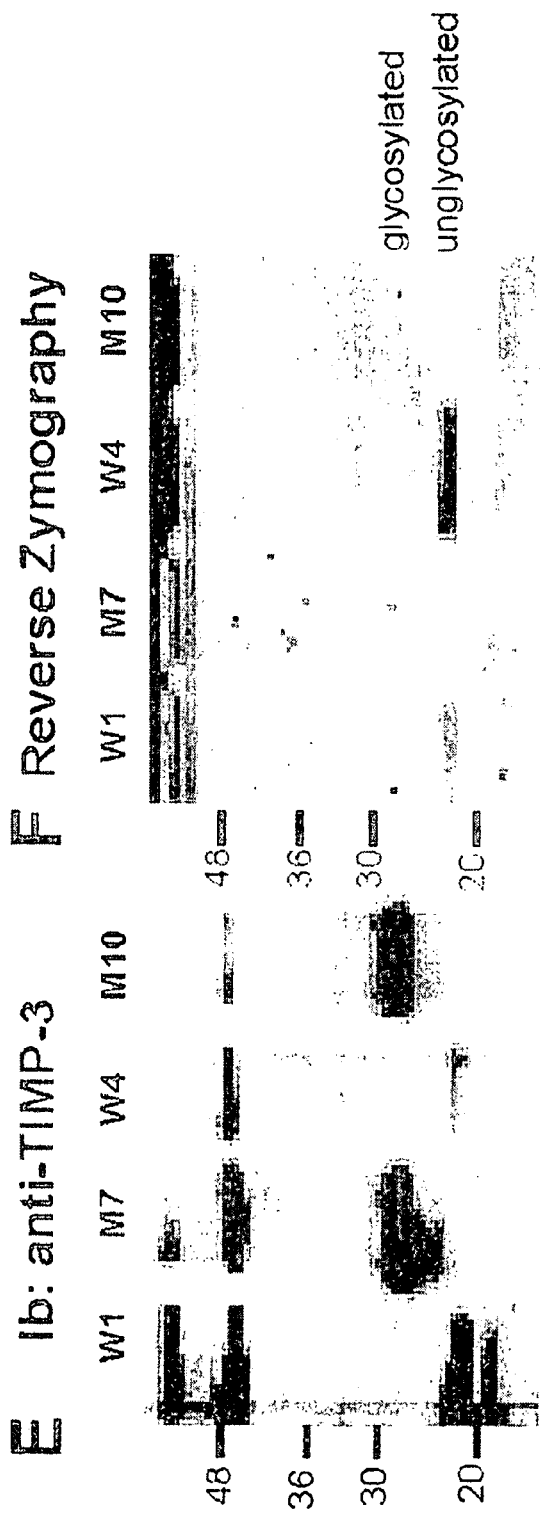
FIG. 13E-F

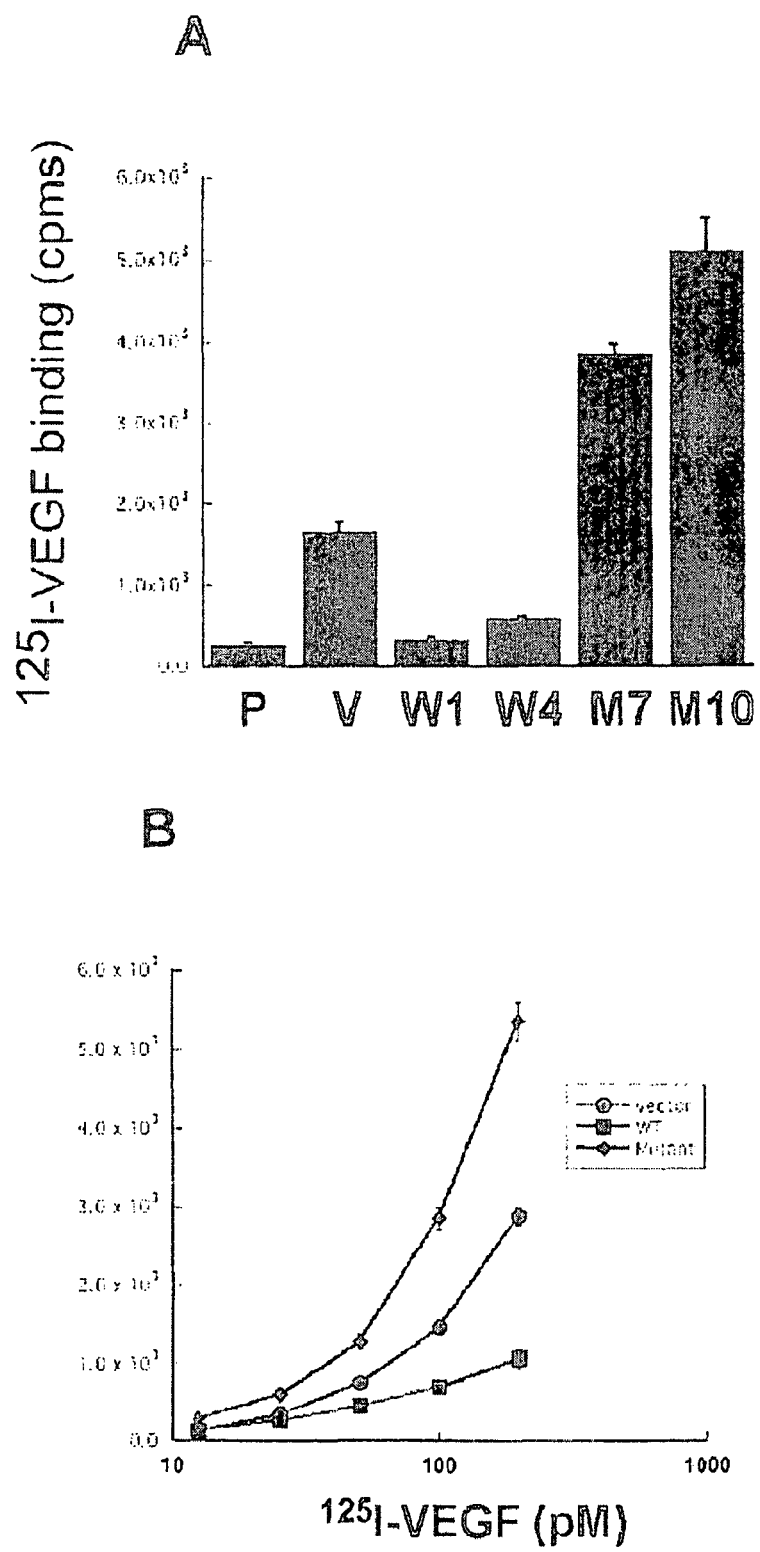
FIG. 14A-B

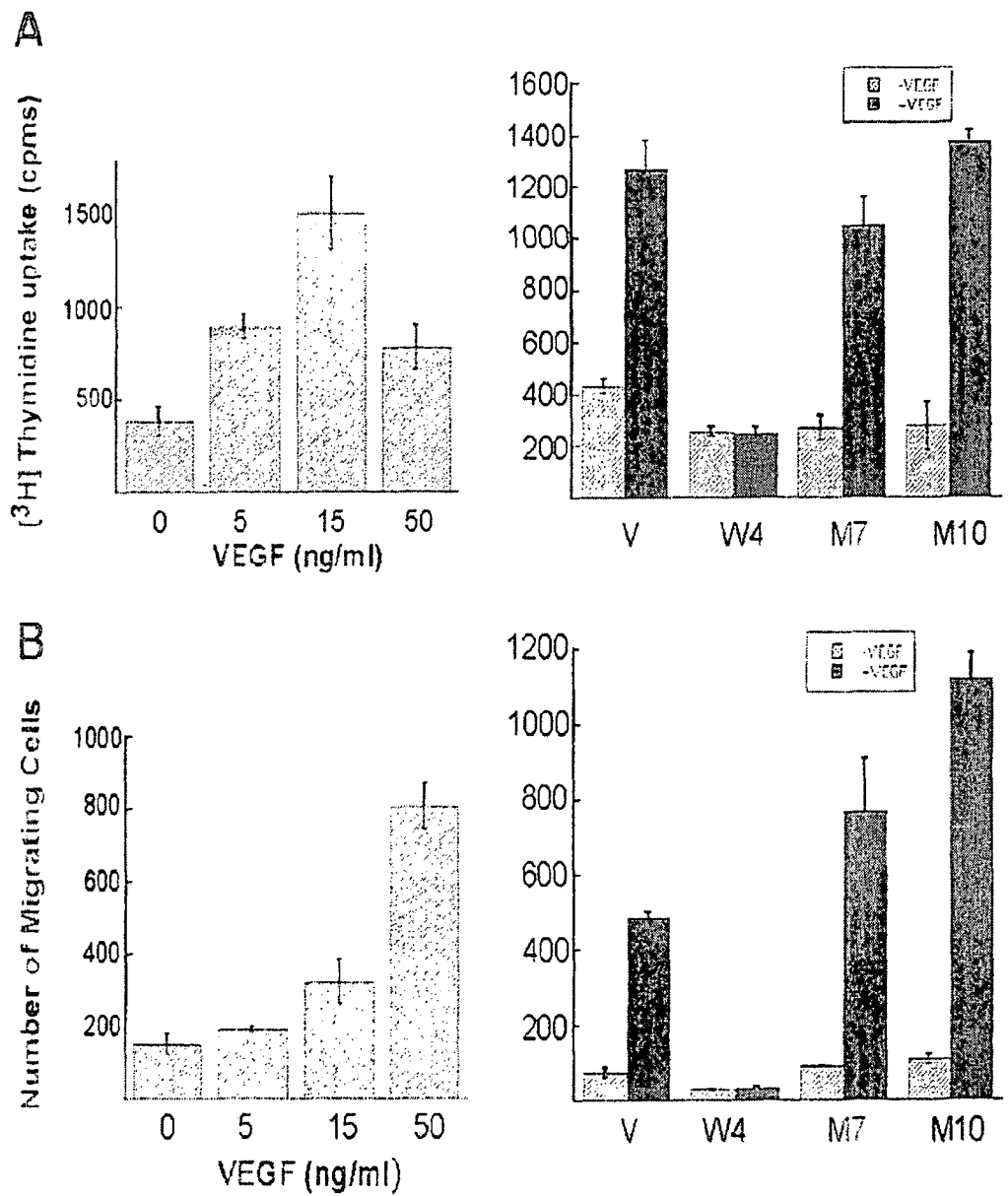
FIG. 15A-B

ANTI-ANGIOGENIC PEPTIDES

RELATED APPLICATIONS

The present application claims priority from PCT International Patent Application No. PCT/US2008/055488, filed Feb. 29, 2008 which claims benefit of U.S. Provisional Patent Application Ser. No. 60/892,553, filed Mar. 2, 2007, and is a continuation-in-part of U.S. patent application Ser. No. 11/653,647, filed Jan. 16, 2007, which is a Divisional of U.S. patent application Ser. No. 10/804,937, filed Mar. 19, 2004, which issued as U.S. Pat. No. 7,183,256 on Feb. 27, 2007, which claims benefits of U.S. Provisional Patent Application Ser. No. 60/456,768, filed Mar. 21, 2003, the entire text and drawings of which are specifically incorporated by reference in their entirety herein.

GOVERNMENT FUNDING

The U.S. Government may own rights in the present invention pursuant to grant number 1 R29EY12109-01 from the National Institutes of Health.

TECHNICAL FIELD

The present invention relates generally to polypeptides and proteins, and, more particularly, to polypeptides, proteins, and nucleic acids encoding such polypeptides and proteins that can be used to inhibit the interaction of vascular endothelial growth factor (VEGF) to VEGF receptor-2 (VEGFR2).

BACKGROUND OF THE INVENTION

Angiogenesis is the development of new vasculature from preexisting blood vessels and/or circulating endothelial stem cells (Asahara et al., Science, 275, (5302): 964-967, 1997; Springer et al., Mol. Cell, 2(5): 549-558, 1998; Folkman and Shing, J. Biol. Chem., 267:10931-10934, 1992). Angiogenesis plays a vital role in many physiological processes, such as embryogenesis, wound healing and menstruation. Angiogenesis is also important in certain pathological events. In addition to a role in solid tumor growth and metastasis, other notable conditions with an angiogenic component are arthritis, psoriasis and diabetic retinopathy (Hanahan and Folkman, Cell, 86(3): 353-364, 1996; Fidler and Ellis Cell 79(2): 185-188, 1994).

Angiogenesis is regulated in normal and malignant tissues by the balance of angiogenic stimuli and angiogenic inhibitors that are produced in the target tissue and at distant sites (Fidler et al., Cancer J. Sci. Am., 4 Suppl 1: S58-66, 1998; McNamara et al. Br. J. Surg., 85(8): 1044-1055, 1998). Vascular endothelial growth factor (VEGF) is an important factor driving angiogenesis or vasculogenesis in numerous physiological and pathological processes, including wound healing (Frank et al., J. Biol. Chem., 270:12607-12613, 1995; Burke et al., Biochem. Biophys. Res. Comm., 207:348-354, 1995), diabetic retinopathy (Alon et al., Nature Med., 1:1024-1028, 1995; Malecaze et al., Arch. Opthalmol, 112:1476-1482, 1994), psoriasis (Detmar et al., J. Exp. Med., 180:1141-1146, 1994), atherosclerosis (Inoue et al., Circulation, 98(20): 2108-16, 1998), rheumatoid arthritis (Harada et al., Scandinavian J. Rheumatol., 27(5): 377-80, 1998; Nagashima et al., Clin. Exp. Immunol., 116(2): 360-5, 1999), solid tumor growth (Plate et al., Int. J. Cancer, 59:520-529, 1994; Claffey et al., Cancer Res., 56:172-181, 1996).

VEGF is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and endothelial cell proliferation factor (Thomas, J. Biol. Chem., 271:603-606, 1996; Neufeld et al., FASEB J., 13(1): 9-22, 1999). Its activity is required for normal embryonic development as targeted disruption of one or both alleles of VEGF results in embryonic lethality (Carmeliet et al., Nature, 380(6573): 435-439, 1996; Ferrara et al., Nature, 380(6573): 439-442, 1996).

A wide variety of cells and tissues produce VEGF, which exists in at least five isoforms (121, 145, 165, 189, and 206 amino acids) that are splice variants encoded by the same gene (Houck et al., Molec. Endo., 5(12): 1806-1814, 1991; Ferrara et al., J. Cell. Biochem., 47:211-218, 1991; Tischer et al., J. Biol. Chem., 266:11947-11954, 1991). The two smaller isoforms, 121 and 165, are secreted from cells (Houck et al., Molec. Endo., 5(12):1806-1814, 1991; Anthony et al., Placenta, 15:557-61, 1994). Secreted VEGF is an obligate dimer of between 38-46 kDa in which the monomers are linked by two disulfide bonds.

VEGF dimers bind with high affinity to two well-characterized receptors, VEGFR1 (FLT-1) and VEGFR2 (KDR/Flk-1), which are selectively expressed on endothelial cells (Flt-1 and Flk-1 are the mouse homologues). The Kd of VEGF binding to VEGFR1 and VEGFR2 is 15-100 pM and 400-800 pM, respectively (Terman et al, Growth Factors, 11(3): 187-195, 1994). A recently identified third cell surface protein, neuropilin-1, also binds VEGF with high affinity (Olander et al., Biochem. Biophys. Res. Comm., 175:68-76, 1991; De Vries et al, Science, 255(5047): 989-991, 1992; Terman et al., Biochem. Biophys. Res. Comm., 187:1579-1586, 1992; Soker et al., Cell, 92(6): 735-745, 1998).

VEGFR1 and VEGFR2 are members of the Type III receptor tyrosine kinase (RTK III) family that is characterized by seven extracellular IgG-like repeats, a single spanning transmembrane domain, and an intracellular split tyrosine kinase domain (Mustonen and Alitalo, J. Cell Biol., 129:895-898, 1995). Until very recently, VEGFR1 and VEGFR2 were thought to be almost exclusively expressed on endothelial cells (Mustonen and Alitalo, J. Cell Biol., 129:895-898, 1995). Although VEGFR1 and VEGFR2 have been reported to have different functions with respect to stimulating endothelial cell proliferation, migration, and differentiation (Waltenberger et al., J. Biol. Chem., 269(43): 26988-26995, 1994; Guo et al., Biol. Chem., 270:6729-6733, 1995), the precise role that each receptor plays in VEGF biology and endothelial cell homeostasis has not been clearly defined.

Recent studies using knockout mice have shown each of VEGF, VEGFR1 and VEGFR2 to be essential for vasculogenesis, angiogenesis and embryo development (Fong et al., Nature, 376:66-70, 1995; Shalaby et al., Nature, 376:62-66, 1995; Hiratsuka et al., Proc. Natl. Acad. Sci. USA, 95(16): 9349-9354, 1998). In studies of lethal knockouts, the phenotypes associated with the lack of each receptor were different. Targeted disruption of VEGFR2 resulted in an embryo that lacked endothelial cell differentiation and failed to form yolk sac blood islands or go through vasculogenesis (Shalaby et al., Nature, 376:62-66, 1995). VEGFR1 null mutants showed impaired vasculogenesis, disorganized assembly of endothelial cells, and dilated blood vessels (Fong et al., Nature, 376: 66-70, 1995; Hiratsuka et al., Proc. Natl. Acad. Sci. USA, 95(16): 9349-9354, 1998). VEGFR1 evidently has a vital biological role.

VEGFR1 has a higher affinity for VEGF than VEGFR2, although it has a lower tyrosine kinase activity. This suggests that the extracellular domain of VEGFR1 is particularly important. This hypothesis was strongly supported by results from studies in knockout mice in which the tyrosine kinase domain of VEGFR1 was deleted while leaving the VEGF binding domain intact (Hiratsuka et al., Proc. Natl. Acad. Sci. USA, 95(16): 9349-9354, 1998). The VEGFR1-tyrosine kinase deficient embryos developed normal blood vessels and survived to term (Hiratsuka et al., Proc. Natl. Acad. Sci. USA, 95(16): 9349-9354, 1998).

In addition to the earlier knockouts (Fong et al., Nature, 376:66-70, 1995; Shalaby et al., Nature, 376:62-66, 1995), the Hiratsuka et al. (1998) studies indicate that VEGFR 1 has a vital biological role. However, tyrosine kinase signaling does not seem to be the critical factor. It is interesting to note that macrophages from the VEGFR1 knockout mice did not exhibit VEGF-induced chemotaxis (Hiratsuka et al., Proc. Natl. Acad. Sci. USA, 95(16): 9349-9354, 1998; incorporated herein by reference), thereby implicating VEGFR I as the receptor responsible for mediating this important biological response to VEGF.

Certain groups have reported VEGFR2 to be the dominant signaling receptor in VEGF-induced mitogenesis, and permeability (Waltenberger et al., J. Mol. Cell. Cardiol., 28(7): 1523-1529, 1994; Zachary, Exp. Nephrol., 6(6): 480-487, 1998; Korpelainen and Alitalo, Curr. Opin. Cell Biol., 10(2): 159-164, 1998). The role of VEGFR1 in endothelial cell function is much less clear, although functions in macrophage migration and chemotaxis were documented in the Hiratsuka et al. (1998) studies discussed above.

Clauss et al. (1996; incorporated herein by reference) also reported that VEGFR1 has important roles in monocyte activation and chemotaxis. In fact, cells of the macrophage/monocyte lineage express only VEGFR1, which is the receptor responsible for mediating monocyte recruitment and procoagulant activity (Clauss et al., J. Biol. Chem., 271(30): 17629-17634, 1996). VEGF binding to VEGFR1 on monocytes and macrophages also acts by raising intracellular calcium and inducing tyrosine phosphorylation (Clauss et al., J. Biol. Chem., 271(30): 17629-17634, 1996).

Binding of the VEGF dimer to the VEGF receptor is believed to induce receptor dimerization. Dimerization of the receptor then causes autotransphosphorylation of specific tyrosine residues, Y801 and Y1175, and Y1213 and Y1333 on the intracellular side of VEGFR2 and VEGFR1, respectively. This leads to a signal transduction cascade, which includes activation of phospholipase Cγ(PLCγ) and phosphatidylinositol 3-kinase (PI3K) and an increase in intracellular calcium ions (Hood and Meininger, Am. J. Physiol., 274(3 Pt 2):H1054-1058. 1998; Hood et al., J. Biol. Chem., 273(36): 23504-23508, 1998; Kroll and Waltenberger, Biochem. Biophys. Res. Commun., 252(3):743-746, 1998).

The intracellular events further downstream in VEGF-induced signaling are less clear, although a number of groups have shown that nitric oxide (NO) is produced after VEGF activation of VEGFR2 (Hood and Meininger, Am. J. Physiol., 274(3 Pt 2):H1054-1058. 19981998; Hood et al., J. Biol. Chem., 273(36):23504-23508, 1998; Kroll and Waltenberger, Biochem. Biophys. Res. Commun., 252(3):743-746, 1998). Activation of VEGFR2, but not VEGFR1, by VEGF has also been shown to activate Src and the Ras-MAP kinase cascade, including the MAP kinases, ERK 1 and 2 (Kroll and Waltenberger, Biol. Chem., 272:32521-7, 1997).

The role of VEGFR1 in endothelial cell function is much less clear, particularly as Flt-1 tyrosine kinase-deficient mice are viable and develop normal vessels. It has been suggested that the main biological role of VEGFR1 on endothelial is as a non-signaling ligand-binding molecule, or "decoy" receptor that might be required to present VEGF to VEGFR2.

The connection between VEGF and pathological angiogenic conditions has prompted various attempts to block VEGF activity. These include the development of certain neutralizing polypeptides against VEGF. Polypeptides against VEGF receptors have also been described, such as described in U.S. Pat. Nos. 5,840,301 and 5,874,542 and, subsequent to the present invention, in WO 99/40118. U.S. Pat. Nos. 5,840,301 and 5,874,542 indeed suggest that blocking VEGF receptors rather than VEGF itself is advantageous for various reasons.

Soluble receptor constructs, tyrosine kinase inhibitors, antisense strategies, RNA aptamers and ribozymes against VEGF or VEGF receptors have also been reported (Saleh et al., Cancer Res., 56:393-4011996; Cheng et al., Proc. Natl. Acad. Sci. USA, 93:8502-8507, 1996; each incorporated herein by reference).

SUMMARY OF THE INVENTION

The present invention relates to a purified antiangiogenic polypeptide that comprises about 10 to about 40 amino acids and has an amino acid sequence corresponding to a portion of SEQ ID NO: 2. The polypeptide inhibiting binding of VEGF to VEGFR2 of cells that express VEGFR2.

In aspect of the invention, the portion of SEQ ID NO: 2 can correspond to a portion of at least one of Loop-5, Loop-6, and the tail portion of the C-terminal region of TIMP-3. The amino acid sequence can also comprise at least one of SEQ ID NO: 11, SEQ ID NO: 12, or SEQ ID NO: 13 and the polypeptide can be substantially free of mettaloproteinase inhibiting activity.

The present invention also relates to a method of inhibiting VEGF binding to the VEGF receptor VEGFR2. The method comprises contacting a cell population including cells that express VEGFR1 (FLT-1) and cells that express VEGFR2 with a composition comprising a biologically effective amount of a polypeptide. The polypeptide comprises about 10 to about 40 amino acids and has an amino acid sequence corresponding to a portion of SEQ ID NO: 2. The portion of SEQ ID NO: 2 can correspond to a portion of at least one of Loop-5, Loop-6, and the tail portion of the C-terminal region of TIMP-3. The amino acid sequence can also comprise at least one of SEQ ID NO: 11, SEQ ID NO: 12, or SEQ ID NO: 13 and the polypeptide can be substantially free of mettaloproteinase inhibiting activity.

The present invention further relates to a method of treating an angiogenic disorder in a subject. The method comprises administering to cells of the subject expressing VEGRFR2 a composition comprising a biologically effective amount of a polypeptide. The polypeptide comprises about 10 to about 40 amino acids and has an amino acid sequence corresponding to a portion of SEQ ID NO: 2. The portion of SEQ ID NO: 2 can correspond to a portion of at least one of Loop-5, Loop-6, and the tail portion of the C-terminal region of TIMP-3. The amino acid sequence can also comprise at least one of SEQ ID NO: 11, SEQ ID NO: 12, or SEQ ID NO: 13 and the polypeptide can be substantially free of mettaloproteinase inhibiting activity.

The present invention additionally relates to a method of inhibiting aberrant angiogenesis in a subject. The method comprises administering to cells of the subject expressing VEGRFR2 contributing to the aberrant angiogenesis a composition comprising a biologically effective amount of a polypeptide. The polypeptide comprises about 10 to about 40 amino acids and has an amino acid sequence corresponding to a portion of SEQ ID NO: 2. The portion of SEQ ID NO: 2 can correspond to a portion of at least one of Loop-5, Loop-6, and the tail portion of the C-terminal region of TIMP-3. The amino acid sequence can also comprise at least one of SEQ ID NO: 11, SEQ ID NO: 12, or SEQ ID NO: 13 and the polypeptide can be substantially free of mettaloproteinase inhibiting activity.

The present invention additionally relates to a method of treating age related macular degeneration (AMD) in a subject. The method includes administering to an eye of the subject with AMD a composition comprising a biologically effective amount of a polypeptide. The polypeptide comprises about 10 to about 40 amino acids and has an amino acid sequence corresponding to a portion of SEQ ID NO: 2. The portion of SEQ ID NO: 2 can correspond to a portion of at least one of Loop-5, Loop-6, and the tail portion of the C-terminal region of TIMP-3. The amino acid sequence can also comprise at least one of SEQ ID NO: 11, SEQ ID NO: 12, or SEQ ID NO: 13 and the polypeptide can be substantially free of mettaloproteinase inhibiting activity. The composition can be administered intravitreally (e.g., intravitreal injection) to treat AMD.

BRIEF DESCRIPTION OF THE DRAWINGS

Further features of the present invention will become apparent to those skilled in the art to which the present invention relates from reading the following description of the invention with reference to the accompanying drawings in which:

FIG. 2 shows graphs indicating: (A) Inhibition of VEGF165 (10 ng/ml)-mediated migration of PAE-KDR cells by recombinant TIMP3 (rTIMP3). (B) Comparison of the effects of rTIMP3, rTIMP1 and BB3103 on VEGF165-induced migration of PAE-KDR cells. (C) Migration of PAE-KDR cells expressing TIMP3 (KDR-TIMP3) toward VEGF121 and VEGF165. In all migration experiments, migrating cell number is expressed as mean±s.e.m. of quadruplicate samples. All experiments were done in triplicate. Open symbols, KDR-vector; closed symbols, KDR-TIMP3.*, $P<0.01$; **, $P<0.05$.

FIG. 5 shows graphs illustrating TIMP3 inhibits binding of VEGF to its receptor, KDR. (A) Effect of TIMP3 on the binding of [125I]VEGF to the surface of PAE-KDR cells and [125I]PDGF-BB to the surface of PAE-PDGFR-β cells. The amount of bound radioligand in the absence of TIMP3 is taken as 100%. Radioligand binding is expressed as percent binding and is the mean±s.e.m. of triplicate samples. (B) Confluent cultures of PAE-KDR cells and PAE-KDR-TIMP3 cells were incubated with 250 pM [125I]VEGF165 in the absence or presence of various concentrations of unlabeled VEGF. Results are expressed as percent maximum, with binding to PAE-KDR cells in the absence of unlabeled VEGF as 100%. All values are expressed as mean±s.e.m. of triplicate samples. (C) [125I] PDGF-BB binding to PAE-PDGFR-β and PAE-PDGFR-β-TIMP3. (D) Scatchard representation of specific binding of [125I]VEGF165 to PAE-KDR cells in the absence or presence of recombinant TIMP3. (E) Scatchard representation of specific binding of [125I]VEGF165 to PAE-KDR-vector or PAE-KDR-TIMP3 cells. (F) Scatchard representation of specific binding of [125I]PDGF-BB to PAE-PDGFR-β-vector or PAE-DGFR-β-TIMP3 cells. (G)

Figure 1:
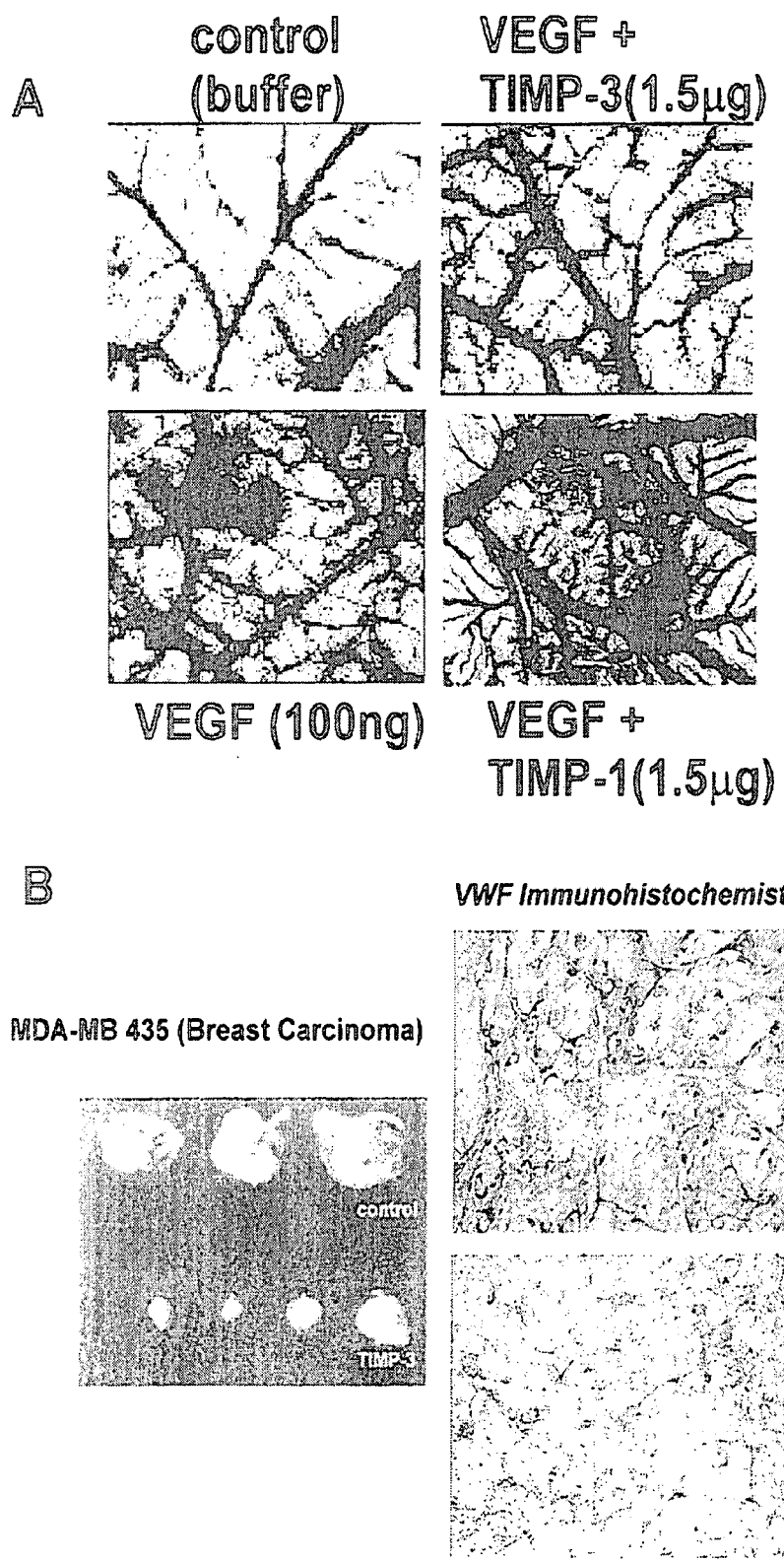
FIG. 1 illustrates that TIMP3 inhibits VEGF-mediated angiogenesis. (A) Chicken CAMs (3 d) were exposed to control buffer (top left), 100 ng VEGF (bottom left), 100 ng VEGF plus 1.5 μg TIMP3 (top right) or 100 ng VEGF plus 1.5 μg TIMP1 (bottom right) for 48 h. (B) Tumors from mice injected subcutaneously with MDA-MB435 human breast carcinoma cells, transfected with empty pCEP4 vector (control) or pCEP4-TIMP3 (TIMP3; left panel). Representative photographs of immunohistochemical staining of 3-μm sections with antibodies to von Willebrand factor (right; control, top; TIMP3, bottom). Brown reaction product depicts endothelial cells lining the vessels.

Comparison of the effect of rTIMP1, rTIMP2, rTIMP3, BB3103 and MMP-2/MMP-9 synthetic inhibitor on the binding of [125I]VEGF165 to PAE-KDR cells. Binding is expressed as mean±s.e.m. Data is shown as percent binding of triplicate samples, with binding to PAE-KDR cells in the absence of any inhibitor as 100%. *, P<0.01. (H) Effect of expression of WT-TIMP3 and TIMP3-C1S on binding of 125I-labeled VEGF165 to MS1 endothelial cells. P<0.01.

FIG. 6 shows TIMP3 inhibits binding of VEGF to KDR but not to Flt-1. (A) Cross-linking of VEGF isoforms to PAE-KDR-vector cells or PAE-KDR-TIMP3 cells, di-KDR, dimeric KDR; mono-KDR, monomeric KDR. (B) Expression of KDR in the lysate and plasma membrane (PM) of PAE-KDR and PAE-KDR-TIMP3 was analyzed by immunoprecipitation (Ip) and western blot (Ib) analysis with antibody specific for KDR. (C) Solid-phase binding of [125I] VEGF165 to purified recombinant soluble KDR-IgG in the absence or presence of recombinant TIMP3. (D) Competitive displacement of [125I]VEGF165 from soluble KDR but not soluble FLT1 with increasing concentrations of recombinant TIMP3 protein. Binding is expressed as percent binding, with binding to KDR and FLT1 in the absence of TIMP3 as 100%. (E) Direct binding of [125I]VEGF165 to TIMP1, TIMP2 or TIMP3. Values are the mean±s.e.m. of triplicate wells.

FIG. 7 illustrates that TIMP3 interacts with KDR. (A) Immunoprecipitation (Ip) analysis of TIMP3 and KDR from KDR-vector and PAE-KDR-TIMP3 cells. (B) Immunoprecipitation (Ip) and western blot (Ib) analysis of TIMP3 and KDR from PAE-KDR-vector and PAE-KDR-TIMP3 cells. Immunoprecipitation of cell lysates with antibodies specific for TIMP3 was followed by immunoblotting with antibodies specific for KDR (top). As a control for KDR receptor, cell lysates were immunoprecipitated with anti-bodies specific for KDR and probed with antibodies specific for KDR Immunoprecipitation with antibodies specific for KDR and immunoblotting with antibodies specific for TIMP3 (bottom) were carried out on PAE-KDR cells exposed to recombinant TIMP3 or PAE-KDR-vector and PAE-KDR cells overexpressing TIMP3, to confirm the interaction. (C) Direct binding of [125I]TIMP3 to soluble KDR protein. Interaction of soluble KDR with [125I]TIMP3 was analyzed after cross-linking, SDS-PAGE and autoradiography. Competition with unlabeled TIMP3 was carried out to ensure specificity. As a control for KDR, cross-linking of [125I]VEGF165 and KDR was carried out in the absence or presence of unlabeled VEGF. (D) Competitive displacement of [125I]TIMP3 from the surface of endothelial cells by unlabeled recombinant VEGF (2 μg/ml) and TIMP3 (10 μg/ml) protein. *, P<0.01. (E) In vivo interaction of KDR and TIMP3 in human placenta. Immunoprecipitation using antibodies specific TIMP3 (top) and KDR (bottom) was followed by immunoblotting with antibodies specific for KDR (top) and TIMP3 (bottom).

FIG. 8 illustrates an assay showing (A) Full length TIMP3, N-terminal TIMP3, and N-terminal TIMP2:C-terminal TIMP3 chimera. (B) C-terminal TIMP3 inhibits binding of VEGF to KDR. 96 well immunoplates were coated with VEGF (80 ng/ml) as per standard procedures. Following washing and blocking the binding of sKDR (receptor IgG chimeric protein) to the plates in the presence or absence of recombinant TIMP3 was quantified by the detection of binding of enzyme linked anti IgG antibody (ELISA assay).

Figure 9:
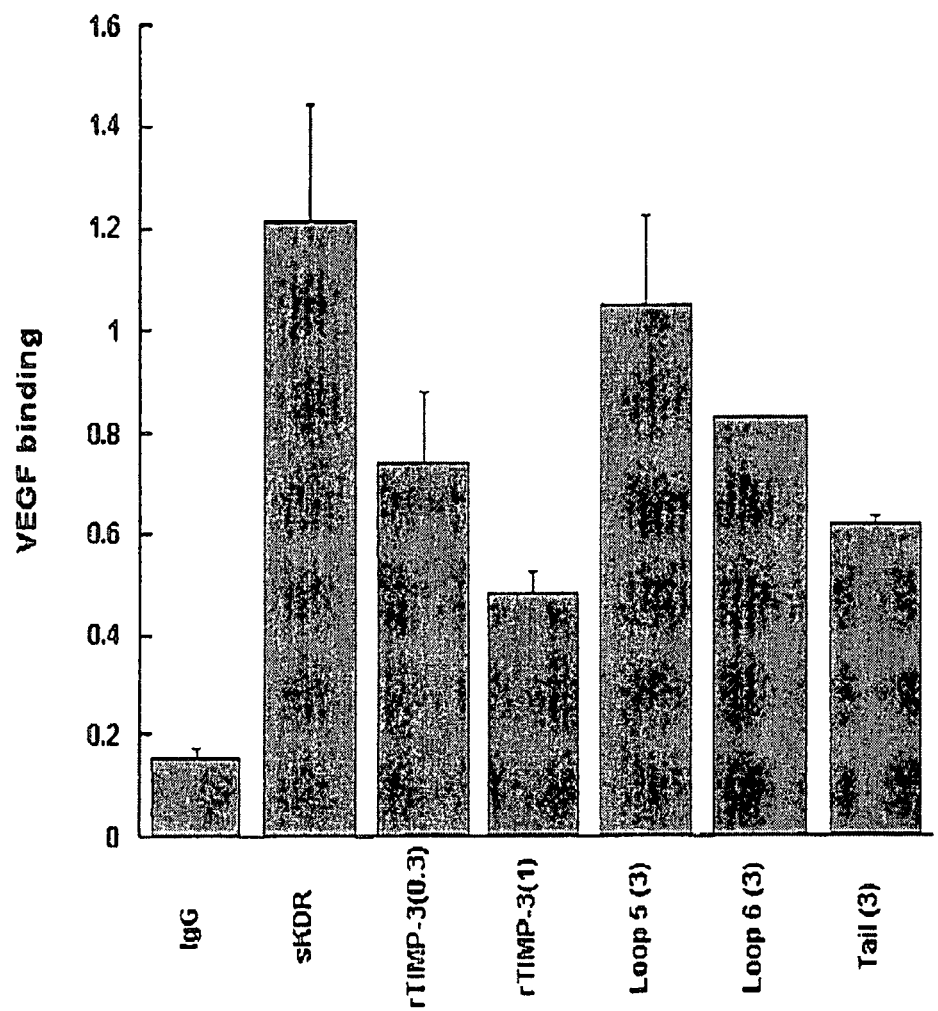

FIG. 9 illustrates a graph showing the ability of peptides in accordance with the present invention to inhibit binding of VEGF to VEGFR2 (KDR).

Figure 10:
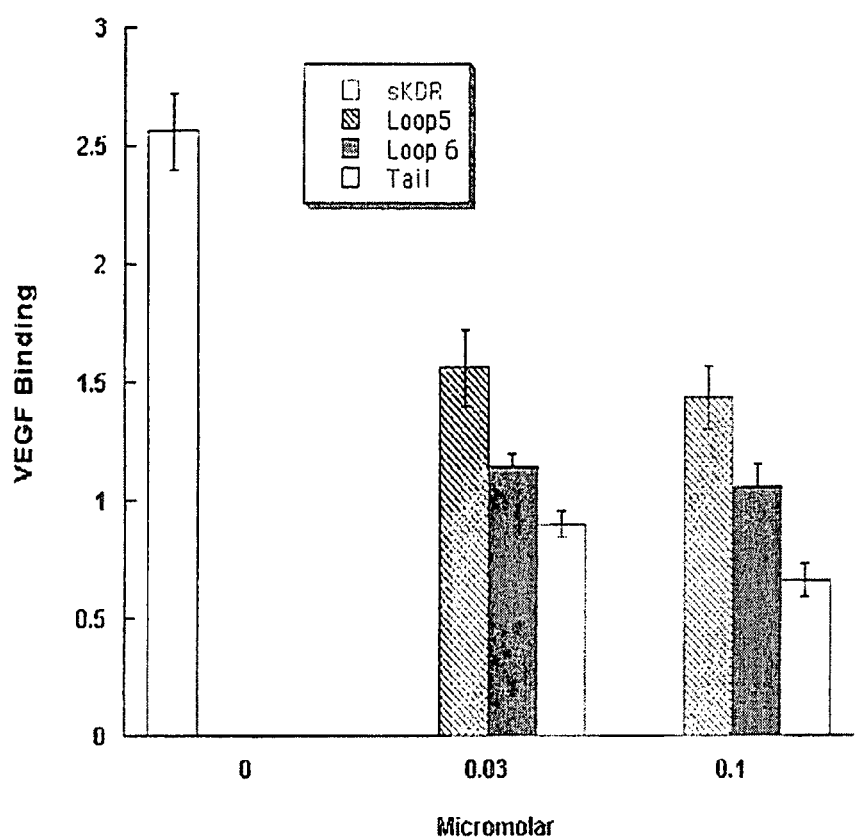

FIG. 10 illustrates a graph showing the ability of peptides in accordance with the present invention to inhibit binding of VEGF to VEGFR2 (KDR) at lower doses.

Figure 11:
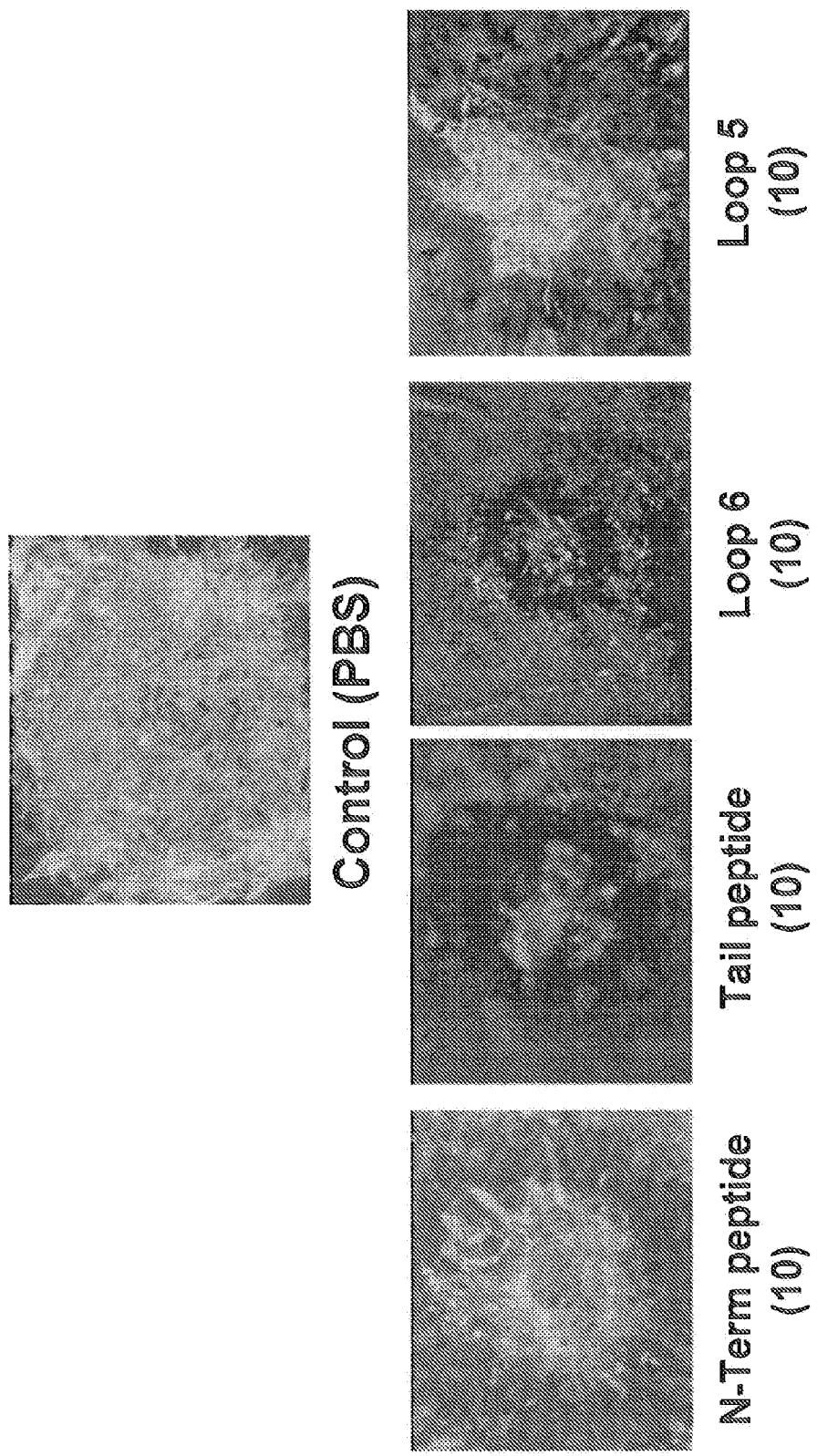

FIG. 11 illustrates the results of a whole mount retina labeled with a fluorescein dextran marker and shows that TIMP-3 peptides inhibit CNV in a mouse model.

Figure 12:
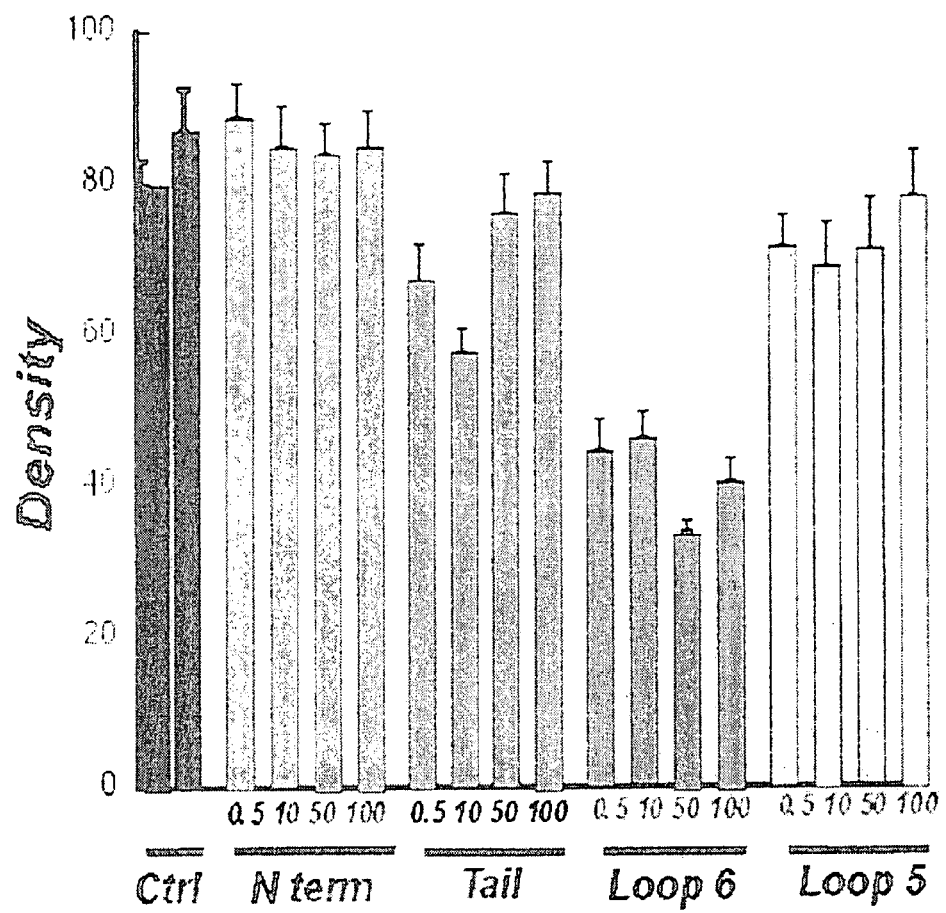

FIG. 12 illustrates a graphical representation of the density of whole mount retina labeled with fluorescein dextran marker and shows that TIMP-3 tail and loop6 peptide inhibit CNV.

FIG. 13 illustrates an analysis of WT-TIMP3 (W1 and W4), S156C-TIMP3-(M7 and M10) and vector-transfected PAEKDR cells (V). (A) Total RNA extracts were analyzed for TIMP-3, KDR and 28S mRNAs by RT-PCR. (B) The expression levels and cellular localization of WT- and S156C-TIMP3 proteins in the ECM and conditioned medium (CM) was determined by immunoblotting with anti-TIMP3 monoclonal antibody. (C) The ECM and CM prepared from mutant cells were treated with or without PNGase F and deglycosylation was analyzed by immunoblotting with anti-TIMP3 monoclonal antibody. WT-TIMP3 in the ECM was used as a positive control for the unglycosylated form. (D) TIMP (MMP inhibitory) activity in the ECM and CM was analyzed by reverse zymography (E) Heparin agarose conditioned medium from WT and mutant cells were analyzed for TIMP-3 by immunoblotting with TIMP-3 monoclonal antibody. (F) Heparin agarose conditioned medium from WT and mutant cells were analyzed for TIMP-3 activity by reverse zymography.

FIG. 14 illustrates that S156-TIMP-3 increases the binding of VEGF to its receptor VEGFR-2. PAEKDR cells expressing WT (W) or S156C-TIMP3 (M) or vector alone (V) were incubated with or without VEGF and analyzed for VEGF binding. (A) 125I-VEGF165 binding is expressed as cpms per well (B) Concentration-dependent 125IVEGF165 binding in PAEKDR cells. All results are mean±SD of a typical experiment. At least three independent experiments gave comparable results. **P<0.01 vs. corresponding vector controls.

FIG. 15 illustrates that S156C-TIMP3 is an inefficient inhibitor of VEGF-mediated EC proliferation, migration and actin reorganization. Serum-starved PAEKDR cells expressing WT (W) or S156C-TIMP3 (M) or vector alone (V) were incubated with or without VEGF and analyzed for proliferation, migration and actin reorganization (A) Proliferation of endothelial cells in response to VEGF (15 ng/ml) for 40 h (right panel). [3H] Thymidine incorporation was measured during the last 4 h of incubation. Optimal concentration of 15 ng/ml was determined from a dose response curve generated using PAEKDR vector transfected cells (left panel). P **p<0.01, *p<0.05 vs unstimulated controls. (B) Migration of endothelial cells towards VEGF (50 ng/ml). Optimal concentration of 15 ng/ml was determined from a dose response curve generated using PAEKDR vector transfected cells (left panel). Migrating cell number is expressed as means±SEM of quadruplicate samples (C). Actin reorganization in PAEKDR cells stimulated with or without 50 ng/ml VEGF for 15 min at 37° C. The arrows indicate membrane edge ruffling. Magnification ×1000.

Figure 16:
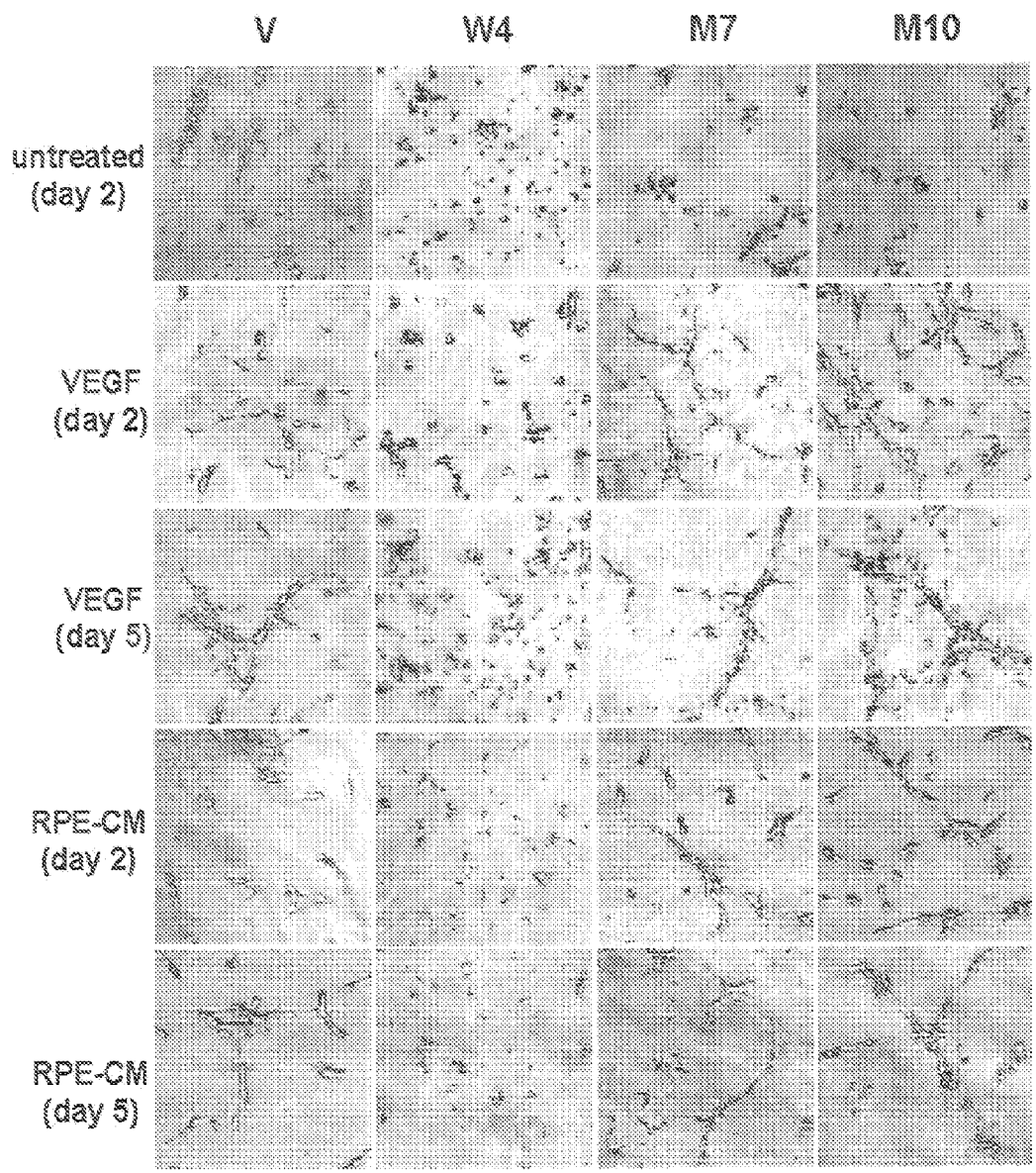

FIG. 16 illustrates that S156C-TIMP3 increases VEGF-dependent EC differentiation but not survival. PAEKDR cells expressing WT (W4) or S156C-TIMP3 (M) or vector alone (V) were cultured between two layers of type 1 collagen gel in the presence or absence of 50 ng/ml VEGF or RPE cell-conditioned media as indicated. Pictures were taken at the indicated times after inoculation. Images of representative microscope fields (×200).

DETAILED DESCRIPTION

The present invention relates generally to the use of polypeptides or proteins comprising tissue inhibitor of mettaloproteinases-3 (TIMP3) or variants of TIMP3 to substantially inhibit vascular endothelial growth factor (VEGF) binding to VEGF receptor-2 (VEGFR2/KDR/Flk-1)) without substantially inhibiting VEGF binding to VEGF receptor 1 (VEGFR1/Flt-1). It was found that polypeptides comprising TIMP3 or variants of TIMP3 can substantially inhibit binding of VEGF to VEGFR2 by blocking VEGF binding to essentially only VEGFR2 or competing with VEGF binding to the VEGFR2. A population of cells or tissues that include a population of endothelial cells that express VEGFR2 and VEGFR1 can thus be contacted with a biologically effective amount of polypeptides or proteins comprising TIMP3 or variants of TIMP3 under conditions effective to substantially inhibit VEGF binding to VEGFR2, without substantially inhibiting VEGF binding to VEGFR1.

The inhibition of VEGF binding to VEGFR2 can potentially inhibit VEGF mediated angiogenesis. Moreover, as VEGFR1 has important biological roles unconnected to angiogenesis, particularly in macrophage migration and chemotaxis, and osteoclast and chondroclast function, the substantial inhibition of VEGF binding to only VEGFR2 and not VEGF provides a distinct advantage.

As used herein, "inhibit", "inhibiting" or "inhibition" includes any measurable reproducible substantial reduction in the interaction of VEGF and VEGFR2 (KDR); angiogenesis; symptoms of diseases correlated to angiogenesis; or any other activities VEGF may mediate. A substantial reduction is a "reproducible", i.e., consistently observed reduction in binding. A "substantial reduction" in terms of the present application is defined as a reproducible reduction (in VEGF binding to VEGFR2) of at least about 25%, or about 50%, at any amount between about 100 fold and about 1000 fold molar excess of polypeptide over VEGF.

Polypeptides comprising TIMP3 or variants of TIMP3 that exhibit a moderate reduction of VEGF binding to VEGFR2 will still be useful, so long as they do not substantially inhibit VEGF binding to VEGFR1. Nonetheless, preferred polypeptides comprising TIMP3 or fragments of TIMP3 will be those that have a more significant ability to inhibit VEGF binding to VEGFR2. These polypeptides are those that exhibit a reproducible ability to reduce VEGF binding to VEGFR2 by at least about 50%, or about 75% at any amount between about 100 fold and about 1000 fold molar excess of polypeptide over VEGF. Although not required to practice the invention, polypeptides comprising TIMP or variants of TIMP3 that reduce VEGF binding to VEGFR2 by at least about 85%, about 90%, about 95% or even higher are by no means excluded. The intention of using polypeptides that do not substantially inhibit VEGF binding to VEGFR1 is to maintain the biological functions mediated by VEGFR1. Therefore, a polypeptide need only maintain sufficient VEGF binding to VEGFR1 so that a biological response is induced by VEGF. Nonetheless, more preferred polypeptides will be those that have a more significant ability to maintain VEGF binding to VEGFR1. These polypeptides are those that exhibit a reproducible ability to maintain VEGF binding to VEGFR1 at levels of at least about 88%, about 90%, about 92%, about 95% or of about 98-99% at any amount between about 100 fold and about 1000 fold molar excess of polypeptide over VEGF.

TIMP3 Polypeptides and Proteins

In accordance with one aspect of the present invention, polypeptides comprising TIMP3 can have part or all of the primary structural conformation (i.e., continuous sequence of amino acid residues) and one or more of the biological properties (e.g., immunological properties and in vitro biological activity) and physical properties (e.g., molecular weight) of the naturally-occurring mammalian TIMP3 protein. For example, the amino acid sequence of the naturally-occurring TIMP3 protein can be substantially identical to SEQ ID No. 1, which is identified as GenBank Accession No. NP 000353. Naturally occurring polypeptides comprising TIMP3 protein can be purified and isolated. The term "purified and isolated" herein means substantially free of unwanted substances so that the present polypeptides of TIMP3 are useful for inhibiting VEGF binding to VEGFR2. For example, one may have a recombinant human TIMP3 substantially free of other human proteins or pathological agents. These polypeptides are also characterized by being a product of mammalian cells, or the product of chemical synthetic procedures or of prokaryotic or eucaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or prokaryote (e.g., *E. coli*) host cells are free of association with any mammalian proteins. The products of expression in vertebrate (e.g., non-human mammalian (e.g., COS or CHO) and avian) cells are free of association with any human proteins. Depending upon the host employed, and other factors, polypeptides of the invention may be glycosylated with mammalian or other eucaryotic carbohydrates or may be non-glycosylated. Polypeptides of the invention may also include an initial methionine amino acid residue (at position −1 with respect to the first amino acid residue of the polypeptide).

It will be appreciated that biologically functional equivalents, or even improvements, of the TIMP3 protein, can be made, generally using TIMP3 as a starting point. Modifications and changes may be made in the structure of such a protein and still obtain a molecule having like or otherwise desirable characteristics. For example, certain amino acids may substituted for other amino acids in the protein structure without appreciable loss of interactive binding capacity.

Since it is the interactive capacity and nature of a protein that defines that protein's biological functional activity, certain amino acid sequence substitutions can be made in a protein sequence (or of course, the underlying DNA sequence) and nevertheless obtain a protein with like (agonistic) properties. It is thus contemplated that various changes may be made in the sequence of the polypeptides without appreciable loss of their biological utility or activity (e.g., TIMP3 ability to inhibit binding of VEGF to VEGFR2).

It is also well understood by the skilled artisan that, inherent in the definition of a "biologically functional equivalent" protein or polypeptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

Following the procedures noted in the published application by Alton et al. (WO83/04053), one can readily design and manufacture genes coding for microbial expression of polypeptides having primary conformations which differ from that herein specified in terms of the identity or location of one or more residues (e.g., substitutions, terminal and intermediate additions and deletions). Alternately, modifications of cDNA and genomic genes may be readily accomplished by well-known site-directed mutagenesis techniques and employed to generate analogs and derivatives of TIMP3. Such products would share at least one of the biological properties of mammalian TIMP3 but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells.

The present invention also embraces TIMP3 variants, such as an analog, derivative, mimetic, or fragment of TIMP3, which inhibits VEGF binding to VEGFR2 (i.e., VEGF inhibiting TIMP3 variants), without substantially inhibiting binding to VEGFR1. Such variants can include a polypeptide encoded by a naturally occurring allelic variant of native TIMP3 gene (i.e., a naturally occurring nucleic that encodes naturally occurring mammalian TIMP3), a polypeptide encoded by an alternative splice form of a native TIMP3 gene, a polypeptide encoded by a homolog of a native TIMP3 gene, and a polypeptide encoded by a non-naturally occurring variant of a TIMP3 gene.

Also comprehended are VEGF inhibiting TIMP3 variants comprising polypeptide fragments duplicating only a part of the continuous amino acid sequence or secondary conformations within TIMP3. These fragments can possess the VEGF inhibiting activity of TIMP3 without possessing any additional functional activities associated with TIMP3 (e.g., metalloproteinase inhibiting activity).

It has been found that only the C-terminal domain of TIMP3 functions in inhibiting VEGF binding to VEGFR2, not the N-terminal domain. The C-terminal domain of TIMP3 generally has amino acid sequence substantially similar to SEQ ID NO: 2; while the N-terminal domain of TIMP3 generally has an amino acid sequence substantially similar to SEQ ID NO: 3. VEGF inhibiting TIMP3 variants in accordance with the invention, therefore, need only comprise a portion of the amino acid sequences of the C-terminal domain of TIMP3 effective to inhibit VEGF binding to VEGFR2 without substantially including the N-terminal domain of TIMP3. This portion can include, for example, residues 122-188 of TIMP3 (i.e., SEQ ID NO: 9) or other residues of the C-terminal domain of TIMP3 effective to inhibit VEGF binding to VEGFR2 without substantially inhibiting VEGF binding to VEGFR1.

These other residues can include, for example, an about 10 to about 30 amino acid synthetic peptide having an amino acid sequence that corresponds (i.e., substantially the same) to a portion of the amino acid sequence loop-5 of the C-terminal region of TIMP-3 (e.g., SEQ ID NO: 11), an about 10 to about 40 amino acid synthetic peptide that has an amino acid sequence that corresponds to a portion of the amino acid sequence of loop-6 of the C-terminal region of TIMP-3 (e.g., SEQ ID NO: 12), and an about 10 to about 30 amino acid synthetic peptide that has an amino acid sequence that corresponds to a portion of the tail portion (i.e., last 30 amino acids of C-terminal region) of the C-terminal region of TIMP-3.

It will be appreciated that as with TIMP3 protein, modifications and changes may be made in the structure and amino acid sequence of the C-terminal domain polypeptide fragment of TIMP3 and still obtain a molecule having like or otherwise desirable characteristics. For example, certain amino acids may substituted for other amino acids in a protein structure without appreciable loss of interactive binding capacity.

Polypeptides or proteins comprising at least a portion of the C-terminal domain of TIMP3 can be operatively linked, conjugated, or attached to a modified N-terminal domain of TIMP3 as well as a modified or natural a N-terminal domain of another TIMP (e.g. TIMP-2 (SEQ ID NO: 7) or TIMP-4). By way of example, a portion of the C-terminal domain of TIMP-3 (SEQ ID NO: 8) can be operatively linked to the N-terminal domain that has been modified to include the attachment of an additional polypeptide to the N-terminal for the creation of a fusion molecule. Additionally, at leas a portion of the C-terminal domain of the TIMP3 can be operatively linked to a molecule or agent, that does not provide metalloproteinase effects to create a fusion protein or conjugate.

VEGF inhibiting TIMP3 variants in accordance with the invention can be obtained by screening polypeptides recombinantly produced from the corresponding fragment of the nucleic acid encoding such polypeptides. In addition, fragments can be chemically synthesized using techniques known in the art, such as conventional Merrifield solid phase f-MOC or t-BOC chemistry.

VEGF inhibiting TIMP3 variants can also include recombinant forms of TIMP3 or fragments of TIMP3. Recombinant polypeptides preferred by the present invention can be encoded by a nucleic acid that has at least 85% sequence identity with the nucleic acid of a gene encoding a mammalian TIMP3 or fragment of TIMP3.

The present invention also includes that class of polypeptides coded for by portions of the DNA complementary to the protein-coding strand of the human cDNA or genomic DNA sequences of TIMP3 i.e., "complementary inverted proteins" as described by Tramontano et al. Nucleic Acid Res. 12: 5049-5059 (1984). Polypeptides or analogs thereof may also contain one or more amino acid analogs, such as peptidomimetics.

TIMP3 Nucleic Acids

A further aspect of the of the present invention relates nucleic acid sequences useful in facilitating expression in prokaryotic or eucaryotic host cells of polypeptides or proteins comprising at least a portion of TIMP3 (e.g., C-terminal domain) and one or more of the biological properties of recombinant human TIMP3, including the ability to substantially inhibit VEGF binding to VEGFR2, without inhibiting VEGF binding to VEGFR1. Such nucleic acid molecules may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence, which encodes a TIMP3, may be substantially identical to a nucleotide sequence SEQ ID NO: 4, GenBank Accession No. NM 000362. It may also be a different coding sequence that, as a result of the redundancy or degeneracy of the genetic code, encodes the same polypeptide as such polynucleotides.

Other nucleic acid molecules within the invention are those that encode variants of TIMP3 such as those that encode fragments, analogs and derivatives of a native TIMP3. One example is a nucleic acid that encodes the C-terminal domain of TIMP3, indicated by SEQ ID NO: 5. Such variants may be, e.g., a naturally occurring allelic variant of a native TIMP3 gene, a homolog of a native TIMP3 gene, or a non-naturally occurring variant of a native TIMP3 gene. These variants have a nucleotide sequence that differs from a native TIMP3 gene in one or more bases. For example, the nucleotide sequence of such variants can feature a deletion, addition, or substitution of one or more nucleotides of a native TIMP3 gene. Nucleic acid insertions are preferably of about 1 to 10 contiguous nucleotides, and deletions are preferably of about 1 to 30 contiguous nucleotides.

In other applications, VEGF inhibiting TIMP3 variants displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of a native TIMP3 gene within the invention are nucleic acids isolated from mammalian tissue that have at least 75% sequence identity with a native TIMP3 gene, and encode polypeptides having structural similarity to a native TIMP3. Homologs of a native TIMP3 gene within the invention are nucleic acids isolated from other species that have at least 75% sequence identity with the native gene, and encode polypeptides having structural similarity to a TIMP3. Public and/or proprietary nucleic acid databases can be searched to identify other nucleic acid molecules having a high percent (e.g., 70, 80, 90% or more) sequence identity to a native TIMP3 gene.

Non-naturally occurring TIMP3 gene variants are nucleic acids that do not occur in nature (e.g., are made by the hand of man), have at least 75% sequence identity with a native TIMP3 gene, and encode polypeptides having structural similarity to a native TIMP3 protein. Examples of non-naturally occurring TIMP3 gene variants are those that encode a fragment of a native TIMP3 protein, those that hybridize to a native TIMP3 gene or a complement of to a native TIMP3 gene under stringent conditions, those that share at least 65% sequence identity with a native TIMP3 gene or a complement of a native TIMP3 gene, and those that encode a TIMP3 fusion protein.

Nucleic acids encoding fragments of a native TIMP3 protein within the invention are those that encode, amino acid residues of a native TIMP3 protein. Shorter oligonucleotides that encode or hybridize with nucleic acids that encode fragments of a native TIMP3 protein can be used as probes, primers, or antisense molecules. Longer polynucleotides that encode or hybridize with nucleic acids that encode fragments of a native TIMP3 protein can also be used in various aspects of the invention. Nucleic acids encoding fragments of a native TIMP3 protein can be made by enzymatic digestion (e.g., using a restriction enzyme) or chemical degradation of the full length native TIMP3 gene or variants thereof.

Nucleic acids that hybridize under stringent conditions to one of the foregoing nucleic acids can also be used in the invention. For example, such nucleic acids can be those that hybridize to one of the foregoing nucleic acids under low stringency conditions, moderate stringency conditions, or high stringency conditions are within the invention.

Nucleic acid molecules encoding a TIMP3 conjugate, such as a fusion protein, may also be used in the invention. Such nucleic acids can be made by preparing a construct (e.g., an expression vector) that expresses a TIMP3 fusion protein when introduced into a suitable host. For example, such a construct can be made by ligating a first polynucleotide encoding a TIMP3 protein fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents. (See, e.g., Zon (1988) Pharm. Res. 5:539-549). To this end, the oligonucleotides may be conjugated to another molecule, e.g., a peptide, hybridization triggered cross-linking agent, transport agent, hybridization-triggered cleavage agent, etc.

According to another aspect of the present invention, the DNA sequences described herein which encode TIMP3 polypeptides are valuable for the information which they provide concerning the amino acid sequence of the mammalian protein which have heretofore been unavailable. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of TIMP3 and its related products.

The DNA provided herein (or corresponding RNAs) may also be used for gene therapy, such as for the treatment of macular degeneration, primary tumor growth, and metastasis. Currently, vectors suitable for gene therapy (such as retroviral or adenoviral vectors modified for gene therapy purposes and of purity and pharmaceutical acceptability) may be administered for therapeutic delivery. Such vectors may incorporate nucleic acid encoding the present polypeptides for expression in the target cells, such as endothelial cells, bone marrow cells, blood cells, liver (or other organ) cells, muscle cells, fibroblasts, or other cells. Additionally, one may use a mixture of such vectors, such as those containing genes for one or more TIMPS, elastase inhibitors or other proteins, which ameliorate the symptoms within the host. Gene therapy may involve a vector containing more than one gene for a desired protein.

Alternatively, one may use no vector so as to facilitate relatively stable presence in the host. For example, homologous recombination may facilitate integration into a host genome. The nucleic acid may be placed within a pharmaceutically acceptable carrier to facilitate cellular uptake, such as a lipid solution carrier (e.g., a charged lipid), a liposome, or polypeptide carrier (e.g., polylysine). A review article on gene therapy is Verma, Scientific American, November 1990, pages 68-84 which is herein incorporated by reference.

The desired nucleic acid may be first placed within a cell, and the cell may be administered to a patient (such as a transplanted tissue) or the desired nucleic acid may be administered directly to the patient for uptake in vivo. The cells to be transferred to the recipient may be cultured using one or more factors affecting the growth or proliferation of such cells, as for example, SCF.

Administration of DNA of the present invention to the target cell may be accomplished by formation of a dispersion of particles, or an aerosol. Typically some type of bulking agent will be involved, and a carrier, such as a lipid or polypeptide. These materials must be pharmaceutically acceptable. One may use a nebulizer for such delivery, such an ultrasonic or dry powder nebulizer. Alternatively, one may use a propellant based system, such as a metered dose inhaler, which may deliver liquid or a suspension of particles.

For gene therapy dosages, one will generally use between one copy and several thousand copies of the present nucleic acid per cell, depending on the vector, the expression system, the age, weight and condition of the recipient and other factors which will be apparent to those skilled in the art.

DNA sequences of the invention are also suitable materials for use as labeled probes in isolating human genomic DNA encoding TIMP3, as mentioned above, and related proteins as well as cDNA and genomic DNA sequences of other mammalian species. DNA sequences may also be useful in various alternative methods of protein synthesis (e.g., in insect cells) or, as described above, in genetic therapy in humans and other mammals. DNA sequences of the invention are expected to be useful in developing transgenic mammalian species which may serve as eucaryotic "hosts" for production of TIMP3 and TIMP3 products in quantity. See, generally, Palmiter et al., Science 222: 809-814 (1983).

Also, one may prepare antisense nucleic acids against the present DNAs. Compare, Khokho et al., Science 243: 947-950 (1989), whereby antisense RNA inhibitor of TIMP conferred oncogenicity on Swiss 3T3 cells. Antisense nucleic acids may be used to modulate or prevent expression of endogenous TIMP3 nucleic acids.

TIMP3 Conjugates

In accordance with another aspect of the invention, polypeptides comprising TIMP3 or VEGF inhibiting TIMP3 variants can also be used to specifically deliver or target therapeutic agents to VEGFR2. The therapeutic agents can be operatively linked, attached, or coupled to TIMP3 or VEGF inhibiting TIMP3 variants. Examples of agents that can be operatively linked, conjugated with or attached to the polypeptides comprising TIMP3 or VEGF inhibiting TIMP3 variants are radiotherapeutic agents (as exemplified by the radiodiagnostics disclosed herein), anti-angiogenic agents, apoptosis-inducing agents, anti-tubulin drugs, anti-cellular or cytotoxic agents and coagulants (coagulation factors).

To generate conjugates recombinant expression may be employed to create a fusion protein, as is known to those of skill in the art and further disclosed herein. Conjugates of TIMP3 or VEGF inhibiting TIMP3 variants may also be generated using avidin:biotin bridges or any of the chemical conjugation and cross-linker technologies developed in reference to polypeptide conjugates.

For certain applications, the therapeutic agents can be cytotoxic or pharmacological agents, particularly cytotoxic, cytostatic or otherwise anti-cellular agents having the ability to kill or suppress the growth or cell division of endothelial cells. In general, these aspects of the invention contemplate the use of any pharmacological agent that can be conjugated TIMP3 or VEGF inhibiting TIMP3 variants and delivered in active form to the targeted endothelium.

Exemplary anti-cellular agents include chemotherapeutic agents, as well as cytotoxins. Chemotherapeutic agents that can be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments can include agents such as cytokines. Basically, any anti-cellular agent may be used, so long as it can be successfully conjugated to, or associated with, a polypeptide in a manner that will allow its targeting, internalization, release and/or presentation to blood components at the site of the targeted endothelial cells.

There may be circumstances, such as when the target antigen does not internalize by a route consistent with efficient intoxication by the toxic compound, where one will desire to target chemotherapeutic agents, such as anti-tumor drugs, cytokines, antimetabolites, alkylating agents, hormones, and the like. A variety of chemotherapeutic and other pharmacological agents have now been successfully conjugated to polypeptides and shown to function pharmacologically, including doxorubicin, daunomycin, methotrexate, vinblastine, neocarzinostatin, macromycin, trenimon and ac-amanitin.

In other circumstances, any potential side-effects from cytotoxin-based therapy may be eliminated by the use of DNA synthesis inhibitors, such as daunorubicin, doxorubicin, adriamycin, and the like. These agents are therefore preferred examples of anti-cellular agents for use in the present invention.

In terms of cytostatic agents, such compounds generally disturb the natural cell cycle of a target cell, preferably so that the cell is taken out of the cell cycle.

A wide variety of cytotoxic agents are known that may be conjugated to polypeptides comprising TIMP3 or VEGF inhibiting TIMP3 variants. Examples include numerous useful plant-, fungus- or bacteria-derived toxins, which, by way of example, include various A chain toxins, particularly ricin A chain; ribosome inactivating proteins, such as saporin or gelonin; α-sarcin; aspergillin; restrictocin; ribonucleases, such as placental ribonuclease; diphtheria toxin; and pseudomonas exotoxin, to name just a few.

Alternatively, the TIMP3 or VEGF inhibiting TIMP3 variants of the invention may be linked to a component that is capable of directly or indirectly stimulating coagulation, to form a coaguligand. Here, the polypeptides may be directly linked to the coagulant or coagulation factor, or may be linked to a second binding region that binds and then releases the coagulant or coagulation factor. As used herein, the terms "coagulant" and "coagulation factor" are each used to refer to a component that is capable of directly or indirectly stimulating coagulation under appropriate conditions, preferably when provided to a specific in vivo environment, such as the tumor vasculature.

Examples of coagulation factors that can be used include Tissue Factor compositions, such as truncated TF (tTF), dimeric, multimeric and mutant TF molecules. "Truncated TF" (tTF) refers to TF constructs that are rendered membrane-binding deficient by removal of sufficient amino acid sequences to effect this change in property. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes. Truncated TF thus substantially fails to convert Factor VII to Factor VIIa in a standard TF assay, and yet retains so-called catalytic activity including activating Factor X in the presence of Factor VIIa.

U.S. Pat. No. 5,504,067 is specifically incorporated herein by reference for the purposes of further describing such truncated Tissue Factor proteins. Preferably, the Tissue Factors for use in these aspects of the present invention will generally lack the transmembrane and cytosolic regions (amino acids 220-263) of the protein. However, there is no need for the truncated TF molecules to be limited to molecules of the exact length of 219 amino acids.

Tissue Factor compositions may also be useful as dimers. Any of the truncated, mutated or other Tissue Factor constructs may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety.

In other embodiments, the tTF constructs may be multimeric or polymeric. In this context a "polymeric construct" contains 3 or more Tissue Factor constructs. A "multimeric or polymeric TF construct" is a construct that comprises a first TF molecule or derivative operatively attached to at least a second and a third TF molecule or derivative. The multimers may comprise between about 3 and about 20 such TF molecules. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

Alternatively, the TIMP3 or VEGF inhibiting TIMP3 variants of the invention may be linked to a component that is capable of directly or indirectly interfering with tubulin. A range of drugs exert their effects via interfering with tubulin activity. As tubulin functions are essential to mitosis and cell viability, certain "anti-tubulin drugs" are powerful chemotherapeutic agents. Some of the more well known and currently preferred anti-tubulin drugs for use with the present invention are colchicine; taxanes, such as taxol; vinca alkaloids, such as vinblastine, vincristine and vindescine; and combretastatins. Other suitable anti-tubulin drugs are cytochalasins (including B, J, E), dolastatin, auristatin PE, paclitaxel, ustiloxin D, rhizoxin, 1069C85, colcemid, albendazole, azatoxin and nocodazole.

The TIMP3 or VEGF inhibiting TIMP3 variants of the present invention may also be used to deliver agents that induce apoptosis in any cells within a tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus EIA (U.S. Pat. No. 5,776,743; incorporated herein by reference) genes.

Other compositions that may be delivered by TIMP3 or VEGF inhibiting TIMP3 variants, include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1p-converting enzyme and family members, which are also reported to stimulate apoptosis Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to the agents of the present invention that target the cell surface receptor, VEGFR1 (as supported by U.S. Pat. No. 5,587,459; incorporated herein by reference).

It will be appreciated that the therapeutic agents conjugated to the TIMP3 or VEGF inhibiting TIMP3 variants are not limited to the therapeutic agents described above and that other therapeutic agents and other agents, which do not have therapeutic properties, can be conjugated to TIMP3 or VEGF inhibiting TIMP3 variants.

In accordance with another aspect of the invention, TIMP3 or VEGF inhibiting TIMP3 variants of the present invention may be readily prepared as fusion proteins using molecular biological techniques. Any fusion protein may be designed and made using any of the therapeutic agents disclosed herein and those known in the art. The fusion protein technology is readily adapted to prepare fusion proteins in which the two portions are joined by a selectively cleavable peptide sequence.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; incorporated herein by reference).

The preparation of such a fusion protein generally entails the preparation of a first and second DNA coding region and the functional ligation or joining of such regions, in frame, to prepare a single coding region that encodes the desired fusion protein. In the present context, the VEGF inhibiting DNA sequence will be joined in frame with a DNA sequence encoding a therapeutic agent. It is not generally believed to be particularly relevant which portion of the construct is prepared as the N-terminal region or as the C-terminal region.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

To obtain a so-called "recombinant" version of the conjugate of TIMP3 or VEGF inhibiting TIMP3 variants, it is expressed in a recombinant cell. The engineering of DNA segment(s) for expression in a prokaryotic or eukaryotic system may be performed by techniques generally known to those of skill in recombinant expression. It is believed that virtually any expression system may be employed in the expression of conjugate constructs comprising TIMP3 or VEGF inhibiting TIMP3 variants.

Such proteins may be successfully expressed in eukaryotic expression systems, e.g., CHO cells, however, it is envisioned that bacterial expression systems, such as E. coli pQE-60 will be particularly useful for the large-scale preparation and subsequent purification of the conjugates comprising TIMP3 or VEGF inhibiting TIMP3 variants. cDNAs may also be expressed in bacterial systems, with the encoded proteins being expressed as fusions with β-galactosidase, ubiquitin, Schistosoma japonicum glutathione S-transferase, and the like. It is believed that bacterial expression will have advantages over eukaryotic expression in terms of ease of use and quantity of materials obtained thereby.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

Recombinantly produced the conjugates comprising TIMP3 or VEGF inhibiting TIMP3 variants may be purified and formulated for human administration. Alternatively, nucleic acids encoding the conjugates may be delivered via gene therapy. Although naked recombinant DNA or plasmids may be employed, the use of liposomes or vectors is preferred. The ability of certain viruses to enter cells via receptor-mediated endocytosis and to integrate into the host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

In accordance with another aspect of the invention, the TIMP3 or VEGF inhibiting TIMP3 variants conjugated to anti-cellular or cytotoxic agents or operatively associated with components that are capable of directly or indirectly stimulating coagulation can be either directly linked or linked to a second binding region. The 'second binding region' approach generally uses a coagulant-binding polypeptide as a second binding region, thus resulting in a bispecific polypeptide construct. The preparation and use of bispecific polypeptides in general is well known in the art, and is further disclosed herein The nucleic acid sequences encoding the chosen polypeptide are attached, in-frame, to nucleic acid sequences encoding the chosen toxin, coagulant, or second binding region to create an expression unit or vector. Recombinant expression results in translation of the new nucleic acid, to yield the desired protein product. Although polypeptide-encoding nucleic acids are employed, rather than protein binding ligands, the recombinant approach is essentially the same as those described hereinabove.

A wide variety of cytotoxic agents are known that may be conjugated to TIMP3 or VEGF inhibiting TIMP3 variants, including plant-, fungus- and bacteria-derived toxins, such as ricin A chain or deglycosylated A chain. The cross-linking of a toxin A chain to a polypeptide, in certain cases, requires a cross-linker that presents disulfide functions. The reason for this is unclear, but is likely due to a need for certain toxin moieties to be readily releasable from the polypeptide once the agent has "delivered" the toxin to the targeted cells.

Each type of cross-linker, as well as how the cross-linking is performed, will tend to vary the pharmacodynamics of the resultant conjugate. Ultimately, in cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Depending on the specific toxin compound used as part of the fusion protein, it may be necessary to provide a peptide spacer operatively attaching the polypeptide and the toxin compound, which is capable of folding into a disulfide-bonded loop structure. Proteolytic cleavage within the loop would then yield a heterodimeric polypeptide wherein the polypeptide and the toxin compound are linked by only a single disulfide bond. An example of such a toxin is a Ricin A-chain toxin.

When certain other toxin compounds are utilized, a non-cleavable peptide spacer may be provided to operatively attach the TIMP3 or VEGF inhibiting TIMP3 variant polypeptide and the toxin compound of the fusion protein. Toxins which may be used in conjunction with non-cleavable peptide spacers are those which may, themselves, be converted by proteolytic cleavage, into a cytotoxic disulfide-bonded form. An example of such a toxin compound is a Pseudonomas exotoxin compound.

Where coagulation factors are used in connection with the present invention, any covalent linkage to the polypeptide should be made at a site distinct from its functional coagulating site. The compositions are thus "linked" in any operative manner that allows each region to perform its intended function without significant impairment. Thus, the polypeptide binds to VEGF, and the coagulation factor promotes blood clotting.

In additional to the general information provided above, TIMP3 or VEGF inhibiting TIMP3 variants may be conjugated to one or more therapeutic agents using certain biochemical cross-linkers. Cross-linking reagents are used to form molecular bridges that tie together functional groups of two different molecules. To link two different proteins in a step-wise manner, hetero-bifunctional cross-linkers can be used that eliminate unwanted homopolymer formation.

Hetero-bifunctional cross-linkers contain two reactive groups: one generally reacting with primary amine group (e.g., N-hydroxy succinimide) and the other generally reacting with a thiol group (e.g., pyridyl disulfide, maleimides, halogens, etc.). Through the primary amine reactive group, the cross-linker may react with the lysine residue(s) of one protein (e.g., the selected polypeptide or fragment) and through the thiol reactive group, the cross-linker, already tied up to the first protein, reacts with the cysteine residue (free sulfhydryl group) of the other protein (e.g., the coagulant).

Compositions therefore generally have, or are derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking.

The spacer arm between the two reactive groups of cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate targeting and toxic or coagulating agents. Linkers that contain a disulfide bond that is sterically hindered may prove to give greater stability in vivo, preventing release of the agent prior to binding at the site of action. These linkers are thus one preferred group of linking agents.

One example of a cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated targeting and therapeutic agents and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

Although it is preferred that any linking moiety will have reasonable stability in blood, to prevent substantial release of the attached agent before targeting to the disease or tumor site, in certain aspects, the use of biologically-releasable bonds and/or selectively cleavable spacers or linkers is contemplated. "Biologically-releasable bonds" and "selectively cleavable spacers or linkers" still have reasonable stability in the circulation.

TIMP3 or VEGF inhibiting TIMP3 variants may thus be linked to one or more therapeutic agents via a biologically-releasable bond. "Biologically-releasable bonds" or "selectively hydrolyzable bonds" include all linkages that are releasable, cleavable or hydrolyzable only or preferentially under certain conditions. This includes disulfide and trisulfide bonds and acid-labile bonds, as described in U.S. Pat. Nos. 5,474,765 and 5,762,918, each specifically incorporated herein by reference.

The use of an acid sensitive spacer for attachment of a therapeutic agent or drug to a polypeptide of the invention is particularly contemplated. In such embodiments, the therapeutic agents or drugs are released within the acidic compartments inside a cell. It is contemplated that acid-sensitive release may occur extracellularly, but still after specific targeting, preferably to the tumor site.

The targeting polypeptides comprising TIMP3 or fragments of TIMP3 may also be derivatized to introduce functional groups permitting the attachment of the therapeutic agent(s) through a biologically releasable bond. The targeting polypeptide may thus be derivatized to introduce side chains terminating in hydrazide, hydrazine, primary amine or secondary amine groups. Therapeutic agents may be conjugated through a Schiff's base linkage, a hydrazone or acyl hydrazone bond or a hydrazide linker (U.S. Pat. Nos. 5,474,765 and 5,762,918, each specifically incorporated herein by reference).

Also as described in U.S. Pat. Nos. 5,474,765 and 5,762,918, each specifically incorporated herein by reference, the targeting anti-VEGF polypeptide may be operatively attached to the therapeutic agent(s) through one or more biologically releasable bonds that are enzyme-sensitive bonds, including peptide bonds, esters, amides, phosphodiesters and glycosides.

Preferred aspects of the invention concern the use of peptide linkers that include at least a first cleavage site for a peptidase and/or proteinase that is preferentially located within a disease site, particularly within the tumor environment. The polypeptide-mediated delivery of the attached therapeutic agent thus results in cleavage specifically within the disease site or tumor environment, resulting in the specific release of the active agent. Certain peptide linkers will include a cleavage site that is recognized by one or more enzymes involved in remodeling.

Peptide linkers that include a cleavage site for urokinase, pro-urokinase, plasmin, plasminogen, TGFβ, staphylokinase, Thrombin, Factor IXa, Factor Xa or a metalloproteinase, such as an interstitial collagenase, a gelatinase or a stromelysin, are particularly preferred. U.S. Pat. Nos. 6,004,555, 5,877,289, and U.S. application Ser. No. 08/482,369, Issue Fee paid Oct. 20, 1998, are specifically incorporated herein by reference for the purpose of further describing and enabling how to make and use targeting agent-therapeutic agent constructs comprising biologically-releasable bonds and selectively-cleavable linkers and peptides. U.S. Pat. No. 5,877,289, issued Mar. 2, 1999, in particular, is specifically incorporated herein by reference for the purpose of further describing and enabling how to make and use targeting agent-therapeutic agent constructs that comprise a selectively-cleavable peptide linker that is cleaved by urokinase, plasmin, Thrombin, Factor IXa, Factor Xa or a metalloproteinase, such as an interstitial collagenase, a gelatinase or a stromelysin, within a tumor environment.

Pharmaceutical Compositions

In accordance with another aspect of the invention, pharmaceutical compositions can be prepared comprising TIMP3, VEGF inhibiting TIMP3 variants, or conjugates thereof. The pharmaceutical compositions will generally comprise an effective amount of TIMP3, VEGF inhibiting TIMP3 variants, or conjugates thereof, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

The TIMP3, VEGF inhibiting TIMP3 variants, or conjugates thereof of the present invention will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such a polypeptide or immunoconjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of TIMP3, VEGF inhibiting TIMP3 variants, or conjugates thereof can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the TIMP3, VEGF inhibiting TIMP3 variants, or conjugates thereof should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of TIMP3, VEGF inhibiting TIMP3 variants, or conjugates thereof admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of polypeptides comprising TIMP3, VEGF inhibiting TIMP3 variants, or conjugates thereof are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver a polypeptides comprising TIMP3, VEGF inhibiting TIMP3 variants, or conjugates thereof in accordance with the present invention. The slow release formulations are typically implanted in the vicinity of the disease site, for example, at the site of a tumor.

Suitable examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the polypeptides comprising TIMP3, VEGF inhibiting TIMP3 variants, or conjugates thereof. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Many diseases with an angiogenic component are associated with the eye. For example, diseases associated with corneal neovascularization that can be treated according to the present invention include, but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

Diseases associated with retinal/choroidal neovascularization that can be treated according to the present invention include, but are not limited to, diabetic retinopathy, macular degeneration, including age-related macular degeneration (AMD) and Sorsby fundus dystrophy, an early-onset, inherited form of macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases that can be treated according to the present invention include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

The polypeptides comprising TIMP3, VEGF inhibiting TIMP3 variants, or conjugates thereof of the present invention may thus be advantageously employed in the preparation of pharmaceutical compositions suitable for use as ophthalmic solutions, including those for intravitreal and/or intracameral administration. For the treatment of any of the foregoing or other disorders a TIMP3, VEGF inhibiting TIMP3 variants, or conjugates thereof composition of the invention would be administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation can contain a TIMP3, VEGF inhibiting TIMP3 variants, or conjugates thereof in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

TIMP3, VEGF inhibiting TIMP3 variants, or conjugates thereof can also be formulated for topical administration. Topical formulations include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of TIMP3, VEGF inhibiting TIMP3 variants, or conjugates thereof for topical use, such as in creams, ointments and gels, includes the preparation of oleaginous or water-soluble ointment bases, as is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

Local delivery via the nasal and respiratory routes is contemplated for treating various conditions. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

Therapeutic Kits

The present invention also provides therapeutic kits including TIMP3, VEGF inhibiting TIMP3 variants, or conjugates thereof for use in the present treatment methods. Such kits will generally contain, in suitable container means, a pharmaceutically acceptable formulation of at least one polypeptide comprising TIMP3, VEGF inhibiting TIMP3 variants, or conjugates thereof. The kits may also contain other pharmaceutically acceptable formulations, either for diagnosis/imaging or combined therapy. For example, such kits may contain any one or more of a range of chemotherapeutic or radiotherapeutic drugs; anti-angiogenic agents; anti-tumor cell polypeptides; and/or anti-tumor vasculature or anti-tumor stroma immunotoxins or coaguligands.

The kits may have a single container (container means) that contains the polypeptides comprising TIMP3, VEGF inhibiting TIMP3 variants, or conjugates thereof, with or without any additional components, or they may have distinct containers for each desired agent. Where combined therapeutics are provided, a single solution may be pre-mixed, either in a molar equivalent combination, or with one component in excess of the other. Alternatively, each of the polypeptides comprising TIMP3, VEGF inhibiting TIMP3 variants, or conjugates thereof and other anti-cancer agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the polypeptides comprising TIMP3, VEGF inhibiting TIMP3 variants, or conjugates thereof, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the polypeptides comprising TIMP3 or fragments of TIMP3 or conjugate to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

Anti-Angiogenic Therapy

In accordance with another aspect of the present invention, the TIMP3, VEGF inhibiting TIMP3 variants, or conjugates thereof may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Harada et al. (1998, specifically incorporated herein by reference) showed that VEGF is involved in the pathogenesis of rheumatoid arthritis and, furthermore, that measurement of serum concentration of VEGF is a noninvasive, useful method for monitoring the disease activity of rheumatoid arthritis. This supports the therapeutic and diagnostic uses of the present invention in connection with rheumatoid arthritis.

Nagashima et al. (1999, specifically incorporated herein by reference) described the inhibitory effects of anti-rheumatic drugs on VEGF in cultured rheumatoid synovial cells. VEGF is constitutively expressed in the synovium of the rheumatoid arthritis. The known anti-rheumatic drug, bucillamine (BUC), was shown to include within its mechanism of action the inhibition of VEGF production by synovial cells. Thus, the anti-rheumatic effects of BUC are mediated by suppression of angiogenesis and synovial proliferation in the arthritic synovium through the inhibition of VEGF production by synovial cells. The use of the present invention as an anti-arthritic therapy is supported by the VEGF inhibitory actions of this existing therapeutic.

Another example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Sorsby fundus dystrophy is an early-onset, inherited form of macular degeneration, characterized by thickening of Bruch's membrane and submacular neovascularization, which are also features of age-related macular degeneration. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, including age-related macular degeneration and Sorsby fundus dystrophy, an early-onset, inherited form of macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. VEGF expression in human coronary atherosclerotic lesions was demonstrated by Inoue et al. (1998, specifically incorporated herein by reference). This evidences the pathophysiological significance of VEGF in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the present invention in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

TIMP3, VEGF inhibiting TIMP3 variants, or conjugates thereof of the invention can also be utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs (see below).

TIMP3, VEGF inhibiting TIMP3 variants, or conjugates thereof provided by this invention are thus broadly applicable to the treatment of any malignant tumor having a vascular component. In using the TIMP3, VEGF inhibiting TIMP3 variants, or conjugates thereof of the invention in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an anti-VEGF polypeptide.

Knowledge of the role of angiogenesis in the maintenance and metastasis of tumors has led to a prognostic indicator for cancers such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies of the present invention will reduce or negate the recurrence of such tumors.

The present invention is contemplated for use in the treatment of any patient that presents with a solid tumor. In light of the specific properties of the polypeptides comprising TIMP3, VEGF inhibiting TIMP3 variants, or conjugates thereof, the therapeutics of the present invention will have reduced side effects. Particular advantages will result in the maintenance or enhancement of host immune responses against the tumor, as mediated by macrophages, and in the lack of adverse effects on bone tissue. The invention will thus be the anti-angiogenic therapy of choice for the treatment of pediatric cancers and patients having, or at risk for developing, osteoporosis and other bone deficiencies.

Although all malignancies and solid tumors may be treated by the invention, the unconjugated polypeptides comprising TIMP3 or VEGF inhibiting TIMP3 variants are particularly contemplated for use in treating patients with more angiogenic tumors, or patients at risk for metastasis.

The present invention is also intended as a preventative or prophylactic treatment. These aspects of the invention include the ability of the invention to treat patients presenting with a primary tumor who may have metastatic tumors, or tumor cells in the earlier stages of metastatic tumor seeding. As an anti-angiogenic strategy, the present invention may also be used to prevent tumor development in subjects at moderate or high risk for developing a tumor, as based upon prognostic tests and/or close relatives suffering from a hereditary cancer.

The conjugated forms of the polypeptides comprising TIMP3 or VEGF inhibiting TIMP3 variants of the invention are particularly contemplated for use in destroying or debulking solid tumors. These aspects of the invention may be used in conjunction with the unconjugated anti-angiogenic polypeptides of the invention, or with other anti-angiogenic approaches.

It will be readily appreciated by those of skill in the art that the immunoconjugate and prodrug forms of the present treatment methods have the distinct advantage of providing a single therapeutic agent with two properties: the inherent anti-angiogenic property of the polypeptide and the therapeutic property of the attached agent (e.g., cytotoxic, coagulative, apoptopic, etc). The conjugated and prodrug treatment forms of the present polypeptides thus have an incredibly wide utility throughout the field of cancer treatment.

The guidance provided herein regarding the more suitable patients for use in connection with the different aspects of the present invention is intended as teaching that certain patient's profiles may assist with the selection of patients for treatment by the present invention. The pre-selection of certain patients, or categories of patients, does not in any way negate the usefulness of the present invention in connection with the treatment of all patients having a vascularized tumor, or other angiogenic disease as described above.

It is not believed that any particular type of tumor should be excluded from treatment using the present invention. However, the type of tumor cells may be relevant to the use of the invention in combination with other therapeutic agents, particularly chemotherapeutics and anti-tumor cell immunotoxins. Both the unconjugated and conjugated aspects of the present therapies will include an anti-angiogenic effect that will inhibit tumor vasculature proliferation. The conjugated and prodrug treatment aspects will further destroy or occlude the tumor vasculature. As the vasculature is substantially or entirely the same in all solid tumors, the present methodology will be understood to be widely or entirely applicable to the treatment of all solid tumors, irrespective of the particular phenotype or genotype of the tumor cells themselves.

Therapeutically effective doses of constructs of TIMP3, VEGF inhibiting TIMP3 variants, or conjugates thereof are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using unconjugated polypeptides comprising TIMP3 or VEGF inhibiting TIMP3 variants in anti-angiogenic therapies, one can also draw on other published data in order to assist in the formulation of doses for clinical treatment. For instance, although the polypeptides of the present invention have distinct advantages over those in the art, the information in the literature concerning treatment with other anti-VEGF polypeptides can still be used in combination with the data and teaching in the present application to design and/or optimize treatment protocols and doses.

The same type of benefits make TIMP3, VEGF inhibiting TIMP3 variants, or conjugates thereof the preferred drugs for the treatment of pediatric cancers. In children with cancer, the need to continue healthy and substantial bone growth is evident. As TIMP3, VEGF inhibiting TIMP3 variants, or conjugates thereof will not substantially impair the activities of osteoclasts and chondroclasts, which are important in developing bone, TIMP3, VEGF inhibiting TIMP3 variants, or conjugates thereof will have important advantages over other polypeptides.

In terms of using conjugated polypeptides comprising TIMP3 or VEGF inhibiting TIMP3 variants in tumor therapy, one may refer to the scientific and patent literature on the success of delivering a wide range of therapeutics to tumor vasculature to achieve a beneficial effect. By way of example, each of U.S. Pat. Nos. 5,855,866; 5,877,289; 5,965,132; 6,051,230; 6,004,555; 5,776,427; 6,004,554; and 6,036,955; are incorporated herein by reference for the purpose of further describing the use of such therapeutic agent-targeting agent constructs. In the present case, the therapeutic agent-targeting agent constructs include targeting agent portions that exert an anti-angiogenic effect, which will magnify or otherwise enhance the anti-tumor activity of the attached therapeutic agent.

Any dose, or combined medicament of TIMP3, VEGF inhibiting TIMP3 variants, or conjugates thereof, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the dose, or combined therapy of TIMP3, VEGF inhibiting TIMP3 variants, or conjugates thereof, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of TIMP3, VEGF inhibiting TIMP3 variants, or conjugates thereof, or combined therapeutics, for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m2) between the experimental animal and the human patient. All such calculations are well known and routine to those of ordinary skill in the art.

It will be understood that lower doses may be more appropriate in combination with other agents, and that high doses can still be tolerated, particularly given the enhanced safety of the polypeptides comprising TIMP3 or VEGF inhibiting TIMP3 variants that bind only to VEGFR2 and the yet further enhanced safety of TIMP3, VEGF inhibiting TIMP3 variants, or conjugates thereof. The use of human or humanized polypeptides (and optionally, human coagulant or anti-angiogenic proteins) renders the present invention even safer for clinical use, further reducing the chances of significant toxicity or side effects in healthy tissues.

The intention of the therapeutic regimens of the present invention is generally to produce significant anti-tumor effects while still keeping the dose below the levels associated with unacceptable toxicity. In addition to varying the dose itself, the administration regimen can also be adapted to optimize the treatment strategy. In administering the particular doses, one would preferably provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

Whether used for treating angiogenic diseases, such as arthritis, psoriasis, atherosclerosis, diabetic retinopathy, age-related macular degeneration, Grave's disease, vascular restenosis, hemangioma and neovascular glaucoma (or other diseases described above), or solid tumors, the present invention can be combined with other therapies.

The TIMP3, VEGF inhibiting TIMP3 variants, or conjugates thereof based treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the polypeptides comprising TIMP3 or VEGF inhibiting TIMP3 variants of TIMP3 based treatment, its combination with the present invention is contemplated.

Diagnostic Imaging

The present invention further provides in vitro and in vivo diagnostic and imaging methods. Such methods are applicable for use in generating diagnostic, prognostic or imaging information for any angiogenic disease, as exemplified by arthritis, psoriasis and solid tumors, but including all the angiogenic diseases disclosed herein. Outside the field of tumor diagnostics and imaging, these aspects of the invention are most preferred for use in in vitro diagnostic tests, preferably either where samples can be obtained non-invasively and tested in high throughput assays and/or where the clinical diagnosis in ambiguous and confirmation is desired.

TIMP3 or VEGF inhibiting TIMP3 variants can linked to one or more detectable agents for use in imaging per se, or for pre-imaging the tumor to form a reliable image prior to treatment. Such compositions and methods can also be applied to the imaging and diagnosis of any other angiogenic disease or condition, particularly non-malignant tumors, atherosclerosis and conditions in which an internal image is desired for diagnostic or prognostic purposes or to design treatment.

TIMP3 or VEGF inhibiting TIMP3 variant based imaging polypeptides will generally comprise a TIMP3 or VEGF inhibiting TIMP3 variant operatively linked, conjugated to, or attached to a detectable label. "Detectable labels" are compounds or elements that can be detected due to their specific functional properties, or chemical characteristics, the use of which allows the component to which they are attached to be detected and further quantified if desired. In polypeptide conjugates for in vivo diagnostic protocols or "imaging methods" labels are required that can be detected using non-invasive methods.

Many appropriate imaging agents are known in the art, as are methods for their attachment to polypeptides and binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the polypeptide (U.S. Pat. No. 4,472,509). Monoclonal polypeptides may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include carbon14, chromium51, chlorine36, cobalt57, copper67, Eu152, gallium67, gallium68, hydrogen3, iodine123, iodine125, iodine131, indium131, iron59, phosphorus32, rhenium186, rhenium188, selenium75, sulphur35, technetium99m and yttrium90. 125I is often being preferred for use in certain embodiments, and technicium99m and indium111 are also often preferred due to their low energy and suitability for long range detection.

Radioactively labeled TIMP3 or VEGF inhibiting TIMP3 variants for use in the present invention may be produced according to well-known methods in the art. For instance, intermediary functional groups that are often used to bind radioisotopic metallic ions to polypeptides are diethylenetriaminepentaacetic acid (DTPA) and ethylene diaminetetraacetic acid (EDTA).

Monoclonal polypeptides can also be iodinated by contact with sodium or potassium iodide and a chemical oxidizing agent such as sodium hypochlorite, or an enzymatic oxidizing agent, such as lactoperoxidase. Polypeptides according to the invention may be labeled with technetium99m by ligand exchange process, for example, by reducing pertechnate with stannous solution, chelating the reduced technetium onto a Sephadex column and applying the polypeptide to this column; or by direct labeling techniques, e.g., by incubating pertechnate, a reducing agent such as SNCl2, a buffer solution such as sodium-potassium phthalate solution, and the polypeptide.

Any of the foregoing type of detectably labeled TIMP3 or VEGF inhibiting TIMP3 variants may be used in the imaging or combined imaging and treatment aspects of the present invention. They are equally suitable for use in in vitro diagnostics. Dosages for in vivo imaging embodiments are generally less than for therapy, but are also dependent upon the age and weight of a patient. One time doses should be sufficient.

The in vivo diagnostic or imaging methods generally comprise administering to a patient a diagnostically effective amount of a TIMP3 or VEGF inhibiting TIMP3 variants that is conjugated to a marker that is detectable by non-invasive methods. The polypeptide-marker conjugate is allowed sufficient time to localize and bind to VEGF within the tumor. The patient is then exposed to a detection device to identify the detectable marker, thus forming an image of the tumor.

In still further embodiments, the present invention provides diagnostic kits, including imaging kits, for use with the imaging methods described above. Accordingly, the TIMP3 or VEGF inhibiting TIMP3 variants are provided in the kit, generally comprised within a suitable container.

The imaging kits will preferably comprise TIMP3 or VEGF inhibiting TIMP3 variants that are already attached to an in vivo detectable label. However, the label and attachment means could be separately supplied.

Either kit may further comprise control agents, such as suitably aliquoted compositions of VEGF, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the polypeptide or antigen may be placed, and preferably, suitably aliquoted. Where a second or third binding ligand or additional component is provided, the kit will also generally contain a second, third or other additional container into which this ligand or component may be placed. The kits may also include other diagnostic reagents for use in the diagnosis of any one or more angiogenic diseases. Preferably, second diagnostics not based upon VEGF binding will be used.

The kits of the present invention will also typically include a means for containing the polypeptide, and any other reagent containers in close confinement for commercial sale. Such containers may include injection or blow-molded plastic containers into which the desired vials are retained.

Methods

In accordance with another aspect of the invention, methods of, and uses in, significantly inhibiting VEGF binding to the VEGF receptor VEGFR2, without significantly inhibiting VEGF binding to the VEGF receptor VEGFR1 are provided. These methods comprise contacting, in the presence of VEGF, a population of cells or tissues that includes a population of endothelial cells that express VEGFR2 (KDR/Flk-1) and VEGFR1 (Flt-1) with a composition comprising a biologically effective amount of at least one of TIMP3, VEGF inhibiting TIMP3 variants, or conjugates thereof under conditions effective to inhibit VEGF binding to the VEGF receptor VEGFR2, without substantially inhibiting VEGF binding to the VEGF receptor VEGFR1.

Further methods and uses of the invention are in analyzing the biological roles of the VEGF receptors termed VEGFR2 and VEGFR1. In the method, a biological composition or tissue that comprises VEGF and a population of cells that express VEGFR2 (KDR/Flk-1) and VEGFR1 (Flt-1) receptors are contacted with a composition comprising a biologically effective amount of at least of at least one of TIMP3, VEGF inhibiting TIMP3 variants, or conjugates thereof. The effect of the VEGFR2-blocking, anti-VEGF polypeptide on at least a first biological response to VEGF is then determined, such that an alteration in a biological response in the presence of the at least one of TIMP3, VEGF inhibiting TIMP3 variants, or conjugates thereof is indicative of a response mediated by the VEGFR2 receptor; and the maintenance of a biological response in the presence of the at least one of TIMP3, VEGF inhibiting TIMP3 variants, or conjugates thereof is indicative of a response mediated by the VEGFR1 receptor.

Proliferation inhibition methods and uses are provided, including those to specifically inhibit VEGF-induced endothelial cell proliferation and/or migration, which generally comprise contacting a population of cells or tissues that includes a population of endothelial cells and VEGF with a composition comprising a biologically effective amount of the at least one of TIMP3, VEGF inhibiting TIMP3 variants, or conjugates thereof under conditions effective to inhibit VEGF-induced endothelial cell proliferation and/or migration.

Methods of, and uses in, inhibiting VEGF-induced endothelial cell proliferation and/or migration, without significantly inhibiting VEGF-induced macrophage chemotaxis are provided, which generally comprise contacting a population of cells or tissues that contains endothelial cells, macrophages and VEGF with a composition comprising a biologically effective amount of the at least one of TIMP3, VEGF inhibiting TIMP3 variants, or conjugates thereof, under conditions effective to inhibit VEGF-induced endothelial cell proliferation and/or migration, without significantly inhibiting VEGF-induced macrophage chemotaxis.

Methods of, and uses in, inhibiting VEGF-induced endothelial cell proliferation and/or migration and, optionally, angiogenesis, without significantly inhibiting VEGF stimulation of macrophages, osteoclasts or chondroclasts are further provided. The methods generally comprise contacting a population of cells or tissues that contain endothelial cells and at least one of macrophages, osteoclasts or chondroclasts, with a composition comprising a biologically effective amount of the at least one of TIMP3, VEGF inhibiting TIMP3 variants, or conjugates thereof under conditions effective to inhibit VEGF-induced endothelial cell proliferation and/or migration or angiogenesis, without significantly inhibiting VEGF stimulation of macrophages, osteoclasts or chondroclasts.

The foregoing methods and uses can be performed in vitro and in vivo. In the latter case the tissues or cells are located within an animal and the at least one of TIMP3, VEGF inhibiting TIMP3 variants, or conjugates thereof is administered to the animal. In both cases, the methods and uses become methods and uses for inhibiting angiogenesis, comprising contacting a tissue comprising, or a population of, potentially angiogenic blood vessels, i.e., those potentially exposed to VEGF, with an anti-angiogenic composition comprising a biologically effective amount of the at least one of TIMP3, VEGF inhibiting TIMP3 variants, or conjugates thereof under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promoter angiogenesis, as well as in the delineation of further information on the angiogenic process. Where the population of potentially angiogenic blood vessels is located within an animal or patient, the anti-angiogenic composition is administered to the animal as a form of therapy.

"Biologically effective amounts", in terms of each of the foregoing inhibitory methods are therefore amounts of the at least one of TIMP3, VEGF inhibiting TIMP3 variants, or conjugates thereof effective to inhibit VEGF-induced endothelial cell proliferation and/or migration; to inhibit VEGF-induced endothelial cell proliferation and/or migration, without substantially inhibiting VEGF-induced macrophage chemotaxis; to inhibit VEGF-induced endothelial cell proliferation and/or migration or angiogenesis, without substantially inhibiting VEGF stimulation of macrophages, osteoclasts or chondroclasts; and, overall, to reduce vascular endothelial cell proliferation and/or migration in a manner effective to inhibit blood vessels growth or angiogenesis.

The invention thus provides methods of, and uses in, inhibiting VEGF-induced angiogenesis and, preferably, treating an angiogenic disease, without substantially inhibiting VEGF stimulation of macrophages, osteoclasts or chondroclasts. The methods generally comprise contacting a population of cells or tissues that contain endothelial cells and at least one of macrophages, osteoclasts or chondroclasts, with a composition comprising a biologically effective amount of the at least one of TIMP3, VEGF inhibiting TIMP3 variants, or conjugates thereof under conditions effective to inhibit VEGF-induced angiogenesis and to treat an angiogenic disease without significantly inhibiting VEGF stimulation of macrophages, osteoclasts or chondroclasts.

Methods of, and uses in, inhibiting VEGF-induced angiogenesis and, preferably, treating an anti-angiogenic disease, without causing significant side effects on bone metabolism are further provided. The methods generally comprise contacting a tissue or a population of angiogenic vessels that contain vascular endothelial cells and at least one of macrophages, osteoclasts or chondroclasts, with a composition comprising a biologically effective of the at least one of TIMP3, VEGF inhibiting TIMP3 variants, or conjugates thereof under conditions effective to inhibit VEGF-induced angiogenesis and to treat an angiogenic disease without causing significant side effects on bone metabolism by not significantly impairing the activities of macrophages, osteoclasts or chondroclasts.

Anti-angiogenic drug screening (in vitro) and therapy (in vivo) are provided in terms of animals and patients that have, or are at risk for developing, any disease or disorder characterized by undesired, inappropriate, aberrant, excessive and/or pathological vascularization. It is well known to those of ordinary skill in the art that as aberrant angiogenesis occurs in a wide range of diseases and disorders, a given anti-angiogenic therapy, once shown to be effective in any acceptable model system, can be used to treat the entire range of diseases and disorders connected with angiogenesis.

Methods of, and uses in, inhibiting VEGF-induced angiogenesis, and, preferably, exerting an anti-tumor or improved anti-tumor effect without significantly inhibiting VEGF stimulation of macrophages, osteoclasts or chondroclasts are further provided. The methods generally comprise contacting a tissue, tumor environment or population of angiogenic vessels that contain vascular endothelial cells and at least one of macrophages, osteoclasts or chondroclasts, with a composition comprising a biologically effective amount of the at least one of TIMP3, VEGF inhibiting TIMP3 variants, or conjugates thereof under conditions effective to inhibit VEGF-induced angiogenesis and to exert an anti-tumor or improved anti-tumor effect without significantly inhibiting VEGF stimulation of macrophages, osteoclasts or chondroclasts.

The present invention thus further provides methods of, and uses in, treating a disease associated with angiogenesis, including all forms of cancer associated with angiogenesis, comprising administering to an animal or patient with such a disease or cancer a therapeutically effective amount of at least a first pharmaceutical composition that comprises at least one of TIMP3, VEGF inhibiting TIMP3 variants, or conjugates thereof.

This invention links both anti-angiogenic methods using unconjugated or naked polypeptides and variants thereof, and vascular targeting methods using conjugates in which the polypeptide, VEGFR2 binding variants thereof, is operatively attached to a therapeutic agent. Unless otherwise specifically stated or made clear in scientific terms, the terms "polypeptide and variant thereof, as used herein, therefore mean an "unconjugated or naked" polypeptide or variant, which is not attached to another agent, particularly a therapeutic or diagnostic agent. These definitions do not exclude modifications of the polypeptide, such as, by way of example only, modifications to improve the biological half life, affinity, avidity or other properties of the polypeptide, or combinations of the polypeptide with other effectors.

The foregoing anti-angiogenic treatment methods and uses will generally involve the administration of the pharmaceutically effective composition to the animal or patient systemically, such as by transdermal, intramuscular, intravenous injection and the like. However, any route of administration that allows the therapeutic agent to localize to the angiogenic site or sites, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the at least one of TIMP3, VEGF inhibiting TIMP3 variants, or conjugates thereof therapeutics in an amount(s) and for a period of time(s) effective to exert anti-angiogenic and/or anti-tumor effects. The passive administration of proteinaceous therapeutics is generally preferred, in part, for its simplicity and reproducibility.

The therapeutic methods and uses of the invention also extend to the provision of nucleic acids that encode at least one of TIMP3, VEGF inhibiting TIMP3 variants, or conjugates thereof therapeutics in a manner effective to result in their expression in the vicinity of the tumor or their localization to the tumor. Any gene therapy technique may be employed, such as naked DNA delivery, recombinant genes and vectors, cell-based delivery, including ex vivo manipulation of patients' cells, and the like.

In yet further embodiments, the invention provides methods for, and uses in, delivering selected therapeutic or diagnostic agents to angiogenic blood vessels associated with disease. Such embodiments are preferably used for delivering selected therapeutic or diagnostic agents to tumor or intratumoral vasculature or stroma, and comprise administering to an animal or patient having a vascularized tumor a biologically effective amount of a composition comprising at least a first immunoconjugate in which a diagnostic or therapeutic agent is operatively attached to of the at least one of TIMP3 or VEGF inhibiting TIMP3 variants.

The delivery of selected therapeutic agents to tumor or intratumoral vasculature or stroma acts to arrest blood flow, or specifically arrest blood flow, in tumor vasculature; to destroy, or specifically destroy, tumor vasculature; and to induce necrosis, or specific necrosis in a tumor. These methods and uses may thus be summarized as methods for treating an animal or patient having a vascularized tumor, comprising administering to the animal or patient a therapeutically effective amount of at least a first pharmaceutical composition comprising at least a first conjugate that comprises at least one of TIMP3 or VEGF inhibiting TIMP3 variants attached to a therapeutic agent.

The "therapeutically effective amounts" for use in the invention are amounts of conjugates of the at least one of TIMP3 or VEGF inhibiting TIMP3 variants effective to specifically kill at least a portion of tumor or intratumoral vascular endothelial cells; to specifically induce apoptosis in at least a portion of tumor or intratumoral vascular endothelial cells; to specifically promote coagulation in at least a portion of tumor or intratumoral blood vessels; to specifically occlude or destroy at least a portion of blood transporting vessels of the tumor; to specifically induce necrosis in at least a portion of a tumor; and/or to induce tumor regression or remission upon administration to selected animals or patients. Such effects are achieved while exhibiting little or no binding to, or little or no killing of, vascular endothelial cells in normal, healthy tissues; little or no coagulation in, occlusion or destruction of blood vessels in healthy, normal tissues; and exerting negligible or manageable adverse side effects on normal, healthy tissues of the animal or patient.

The terms "preferentially" and "specifically", as used herein in the context of promoting coagulation in, or destroying, tumor vasculature, and/or in the context of binding to tumor stroma and/or causing tumor necrosis, thus mean that the conjugates of the at least one of TIMP3 or VEGF inhibiting TIMP3 variants function to achieve stromal binding, coagulation, destruction and/or tumor necrosis that is substantially confined to the tumor stroma, vasculature and tumor site, and does not substantially extend to causing coagulation, destruction and/or tissue necrosis in normal, healthy tissues of the animal or subject. The structure and function of healthy cells and tissues is therefore maintained substantially unimpaired by the practice of the invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Effect of TIMP3 on VEGF-Mediated Angiogenesis

A chick embryo chorioallantoic membrane (CAM) assay was used to determine the effect of TIMP3 on in vivo angiogenesis. Recombinant human VEGF165 (100 ng), incorporated into methylcellulose disks, induced branching and leakage of blood vessels, presumably due to the induction of vascular permeability. At doses of 0.75 µg/disk and 1.5 µg/disk, TIMP3 inhibited both these responses in 75% (n=8) and 90% (n=10) of CAMs, respectively (FIG. 1a). At similar doses, TIMP1 did not show any angiogenesis inhibition (0% of CAMs tested, n=10). Quantitation of tertiary branchpoints of capillaries determined a decreased angiogenic index with VEGF plus TIMP3 (90±1) as compared with VEGF (190±5) and VEGF plus TIMP1 (172±8). It was previously shown that TIMP3 inhibits tumor growth Immunohistochemical staining of human breast tumors expressing TIMP3, with antibodies against von Willebrand factor, showed a decrease in neovascularization as compared with control tumors (FIG. 1B); similar to that recently described in a mouse tumor model 22. These results suggest an important regulatory function for TIMP3 in tumor-induced neovascularization. Considering that VEGF is believed to induce angiogenesis by engaging KDR, we tested the ability of TIMP3 to inhibit VEGF-induced migration and proliferation of endothelial cells expressing KDR. VEGF can induce endothelial cell chemotaxis, an essential component of angiogenesis. When added exogenously to endothelial cells, recombinant TIMP3 inhibited their migration toward VEGF in a dose-dependent manner (FIG. 2A), with complete inhibition occurring at a dose of 3 μg/ml. The inhibition of migration was not observed with TIMP1 or with the synthetic MMP inhibitor BB3103 (FIG. 2B), indicating that TIMP3 is unique in this regard. We generated stable endothelial cell lines that expressed KDR or platelet-derived growth factor receptor-β (PDGFR-β) on their surface as well as functional TIMP3 in their ECM (FIG. 3D). The stable expression of TIMP3 was confirmed by western blot analysis using polyclonal antibodies against TIMP3 (FIG. 3D). Reverse zymography confirmed that TIMP3 was a functional MMP inhibitor in these cells (FIG. 3D). Stable expression of TIMP3 in the endothelial cells resulted in an attenuation of the chemotactic response to VEGF121 and VEGF165 (FIGS. 2C, 2D).

Figure 3C:
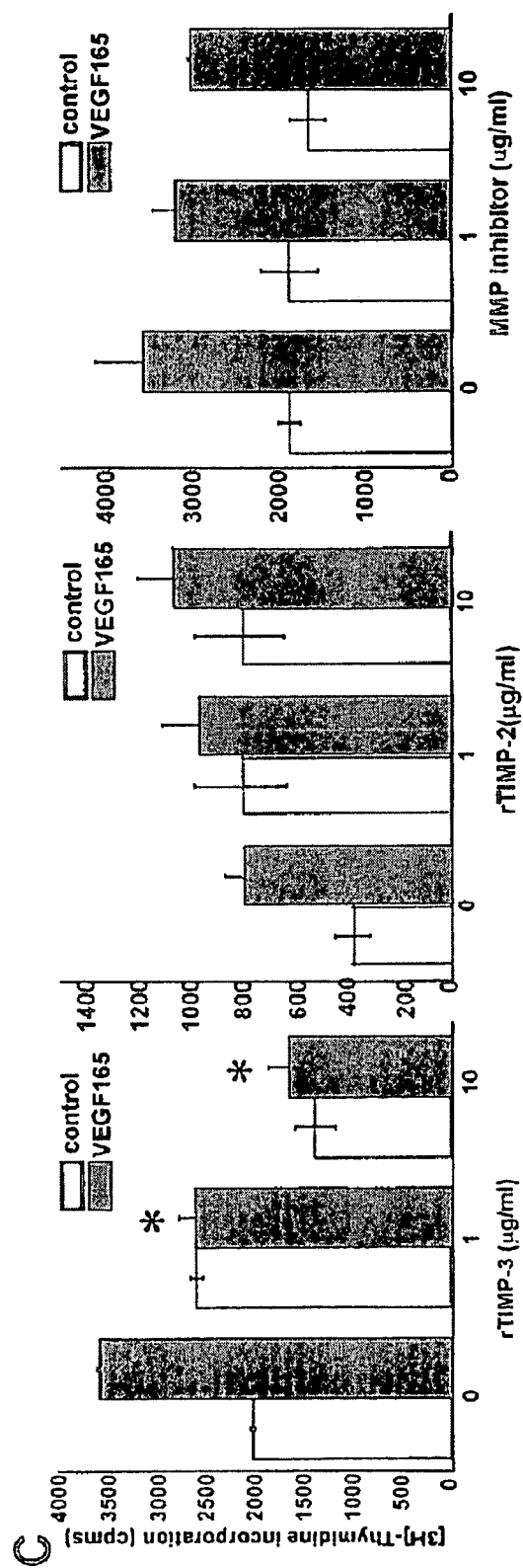
FIG. 3 shows graphs indicating TIMP3 inhibits VEGF-mediated endothelial cell proliferation. (A) Proliferative response of PAE-KDR cells to VEGF165 (5 ng/ml; left) and VEGF121 (30 ng/ml; right). Effects of recombinant TIMP3 (rT3; 0.3 μg/ml and 1 μg/ml), TIMP1 (rT1; 1 μg/ml) and BB3103 (10 μm) were examined by pretreatment of cells for 30 min before the addition of VEGF. (B) Effect of TIMP3 (1 μg/ml and 5 μg/ml) on proliferative response of PAE-PDGFR-β to PDGF-BB and PAE-FGFR1 to bFGF compared to control. (C) DNA synthesis of endothelial cells in response to VEGF165. Effects of rTIMP3, rTIMP2 and synthetic MMP inhibitor were examined by pretreatment of cells before addition of VEGF. [3H]thymidine incorporation was measured during the last 5 h of incubation. (D) Analysis of endothelial cell expressing TIMP3. Expression of TIMP3 protein was confirmed by immunoblotting with TIMP3-specific antibody in PAE-KDR cells (top left). Ability of overexpressed TIMP3 to inhibit felatinases was analyzed by reverse zymography in ECM preparations of PAE-KDR (bottom left) and PAE-PDGFR-β cells (bottom right). (E) Proliferative response of endothelial cells expressing KDR-TIMP3 (left) or PDGFR-β-TIMP3 (right) to VEGF121 and VEGF165 was compared with response in cells lacking TIMP3 (KDR-vector and PDGFR-β-vector, respectively). PDGF-BB (F) Analysis of mouse endothelial cells infected with adenovirus expressing WT-TIMP3 (WT-T3) and TIMP3Cys 1-Ser (T3-C1S). Expression of TIMP3 protein was determined by immunoblotting with antibody against TIMP3 (top left). MMP-inhibitory activity was determined by reverse zymography (top right). Corresponding densitometric quantitation is expressed as arbitrary optical density (OD) units±s.d. (C) DNA synthesis in adenovirus-infected cells in response to VEGF. Effect of expression of 'inactive' TIMP3 on DNA synthesis induced by VEGF was measured by incorporation of [3H]thymidine. In all proliferation experiments, total number of cells was counted at 48 h. Proliferating cell number is expressed as means±s.e.m. of quadruplicate samples. DNA synthesis data represent the means±s.e.m. of triplicate samples; similar results were obtained in at least 2 different experiments. *, $P<0.01$.

Purified recombinant TIMP3, when added exogenously to endothelial cells at doses of 0.3-1 μg/ml, inhibited the proliferative response to VEGF165 and VEGF121 (FIG. 3A). Recombinant TIMP3 (1 μg/ml and 10 μg/ml), but not recombinant TIMP2 or synthetic MMP inhibitor, could also inhibit DNA synthesis of cells in response to VEGF165, as measured by uptake of [3H]thymidine (FIG. 3C). As with exogenously added recombinant TIMP3, over-expression of TIMP3 in endothelial cells resulted in an attenuation of the proliferative response to VEGF165 and VEGF121 (FIG. 3E). Neither recombinant TIMP3 nor TIMP3 overexpression affected the proliferative response of endothelial cells to PDGF-BB or basic fibroblast growth factor (bFGF; FIGS. 3B and 3E), suggesting the inhibitory effect to be specific for VEGF. None of the other TIMPs tested (FIG. 3A) could inhibit this response, indicating that this VEGF-inhibitory function is unique to TIMP3 and may be independent of its MMP-inhibitory activity. The N-terminal domain of TIMP3 contains the Cys 1 residue that is critical for metalloproteinase inhibition. To confirm that MMP inhibition is not required for the anti-angiogenic effect, we infected mouse endothelial cells (MS1) with an adenovirus (Rad66; see Methods) expressing a recombinant TIMP3 protein (TIMP3Cys1-Ser) that has reduced metalloproteinase-inhibitory activity. Earlier studies showed that infection with the adenovirus expressing wild-type TIMP3 could promote apoptosis in some cell lines such as vascular smooth muscle cells, HeLa and HT1080, but not in others such as COS-7 and endothelial cells. No apoptosis was observed in the MS1 cells after infection with wild-type or mutant virus. Whereas expression levels in cells infected with the recombinant adenovirus Rad-TIMP3Cys1-Ser were similar to those produced by the adenovirus expressing wild-type TIMP3 (FIG. 3F), reverse zymography of ECM extracts showed that recombinant TIMP3Cys1-Ser had reduced metalloproteinase-inhibitory activity (FIG. 3F). Endothelial cells infected with Rad-TIMP3Cys1-Ser were still inhibited in their proliferative response to VEGF, as measured by incorporation of [3H]thymidine (FIG. 3G).

TIMP3 Inhibits VEGF-Induced KDR and MAPK Phosphorylation

Figure 4A:
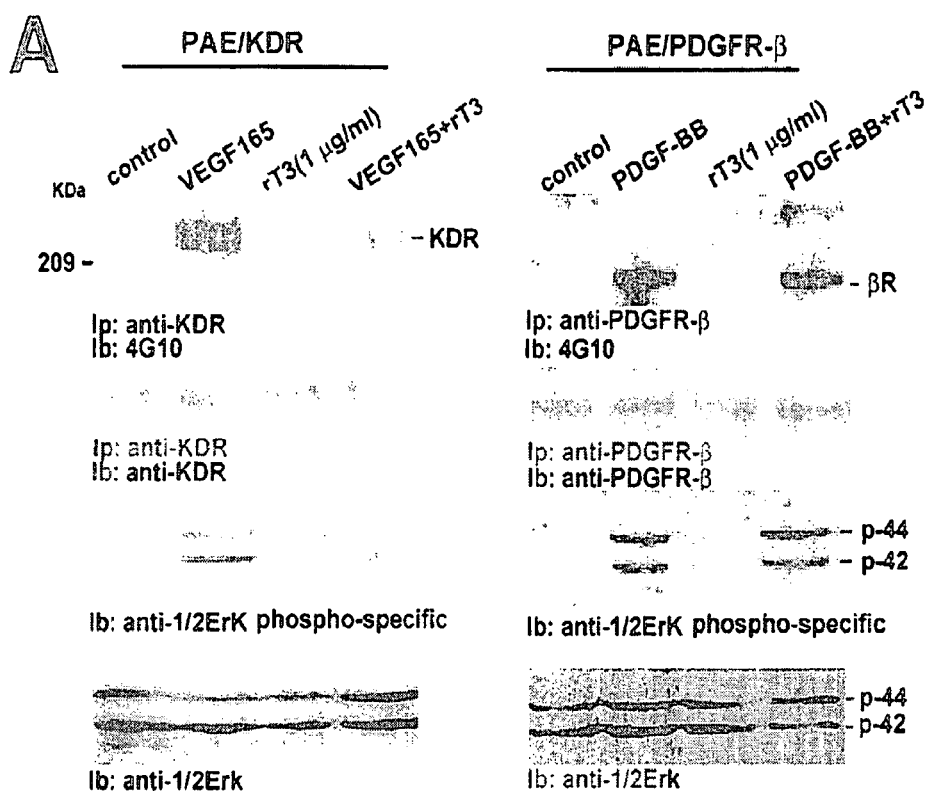
FIG. 4 illustrates that TIMP3 inhibits KDR-mediated signaling. (A) Effect of re-combinant TIMP3 on growth factor-mediated phosphorylation of the receptor was examined by immunoprecipitation (Ip) of cell lysates with antibody specific for KDR (anti-KDR) and immunoblotting (Ib) with phosphotyrosine-specific antibody 4G10 in PAE-KDR cells treated with 50 ng/ml of VEGF165 (top left panel). PDGF-BB-mediated phosphorylation was examined similarly in PAEŠPDGFR-β cells (anti-PDGFR-β; top right panel). (B) VEGF165-mediated phosphorylation of KDR in PAE-KDR cells overexpressing TIMP3 (top left). PDGF-BB-mediated phosphorylation of PDGFR-β in PAE-PDGFR-β cells overexpressing TIMP3 (top right). KDR protein or PDGFR-β protein was analyzed by both immunoprecipitation and immunoblotting with antibodies specific for KDR (left) or for PDGFR-β (right; A and B, second panels from top). Phosphorylation of ERK1 and ERK2 in response to VEGF or PDGF-BB was detected by immunoblotting with phospho-specific ERK1/2 antibodies (anti-ERK1/2 phosphospecific; A and B, third panels from top). Total protein levels of ERK were determined by immunoblotting with antibodies specific for ERK1/2 (anti-ERK1/2; A and B, bottom).
Figure 4B:
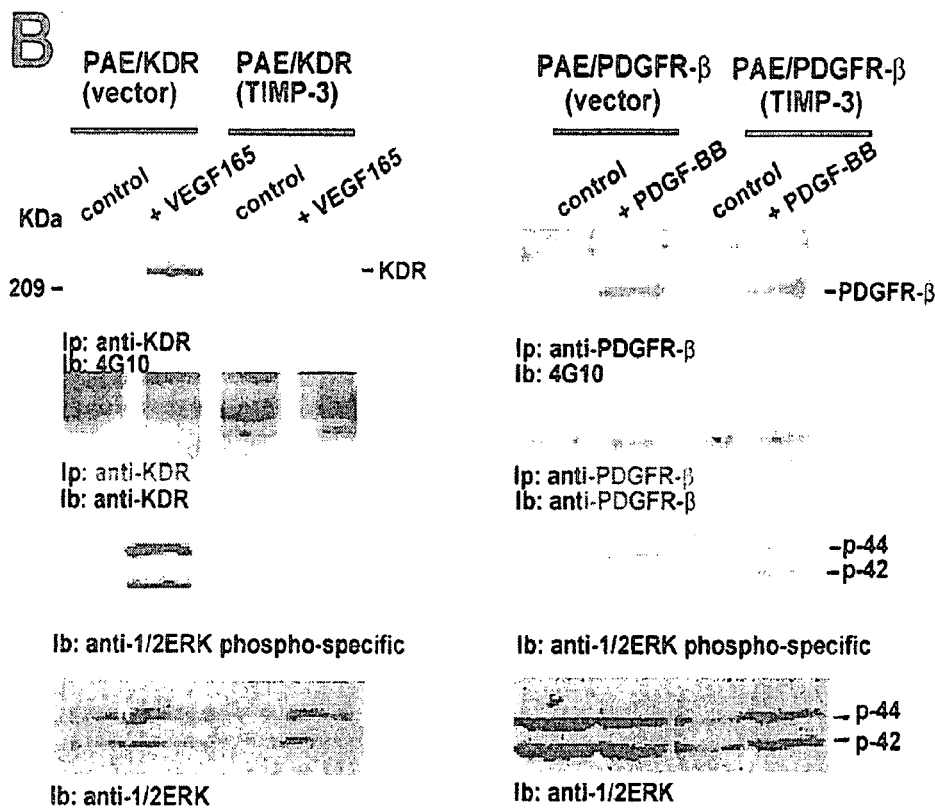

VEGF mediates its activity by binding to its receptor, leading to phosphorylation of the receptor and a series of downstream signaling events. We found that 1 μg/ml of recombinant TIMP3 strongly inhibited VEGF165-induced phosphorylation of KDR in response to VEGF165 (FIG. 4A) but did not affect the phosphorylation of PDGFR-β when stimulated with PDGF-BB. Similarly, overexpression of TIMP3 in endothelial cells also attenuated the response to VEGF165 but not downstream phosphorylation of ERK1 and ERK2 was inhibited in response to VEGF, but not to PDGF-BB, by recombinant TIMP3 (FIG. 4A), as well as in cells overexpressing TIMP3 (FIG. 4B). Neither exogenous addition of TIMP3 nor overexpression of TIMP3 affected the protein expression of KDR, ERK1 or ERK2.

TIMP3 Inhibits Binding of VEGF to KDR Independently of its MMP-Inhibitory Activity We examined the effect of TIMP3 on the binding of VEGF to one of its receptors, KDR, on the surface of endothelial cells. Exogenous addition of recombinant TIMP3 (FIG. 5A) as well as overexpression of TIMP3 in endothelial cells (FIG. 5B) resulted in decreased binding of [125I]VEGF to the surface of cells expressing KDR. Pretreatment of KDR-transduced porcine aortic endothelial (PAE-KDR) cells with recombinant TIMP3 inhibited the binding of [125I]VEGF to PAE-KDR cells in a concentration-dependent manner, with a half-maximal inhibitory concentration (IC50) of 3.3-4.5 μg/ml (FIG. 5A). In comparison, cold VEGF competed with labeled VEGF for binding to PAE-KDR cells with an IC50 of 8.5-15 ng/ml (FIG. 5B). Neither recombinant TIMP3 nor overexpression of TIMP3 could inhibit binding of PDGF-BB to PAE-PDGFR-β cells (FIGS. 5A and 5C) in which PDGF-BB could inhibit binding with an IC50 of 19-23 ng/ml (FIG. 5C). The effect of TIMP3 on the affinity and binding capacity of VEGF for PAE-KDR cells was evaluated in a binding assay (FIG. 5D). Scatchard plot analysis revealed that untreated PAE-KDR cells possessed a large number of high-affinity VEGF-binding sites ($3.3 \times 10^6$-$6.9 \times 10^6$ sites/cell), which bound VEGF with a Kd of 50-100 pM. These results are consistent with those reported earlier for endothelial cells. Treatment with recombinant TIMP3 resulted in reduced binding affinity of VEGF165 with a Kd of 333 pM and expression of $1.9 \times 10^6$ binding sites per cell (FIG. 4d). Similar experiments in PAE-KDR-TIMP3 cells stably transfected with TIMP3 cDNA showed a reduction in the binding affinity of VEGF (Kd=250 pM) and the number of binding sites for VEGF ($1.4 \times 10^5$ binding sites per cell), compared with cells transfected with an empty vector (Kd=50-100 pM; FIG. 5E). These results suggest that the mechanism of inhibition of VEGF binding by TIMP3 is likely to be competitive. Overexpression of TIMP3 in PAE cells expressing PDGFR-β did not affect either the binding affinity of [125I]PDGF (Kd=1 nM) or the number of binding sites per cell ($4.2 \times 10^7$ binding sites per cell), as compared with cells expressing PDGFR-β but not TIMP3 (Kd=1.1 nM and $3.9 \times 10^7$ binding sites per cell; FIGS. 5C and 5F). We also found that recombinant TIMP1, recombinant TIMP2, synthetic MMP inhibitor BB3103, and MMP-2 and MMP-9 inhibitor (2R)-[(4-biphenylylsul-fonyl) amino]-N-hydroxy-3-phenylpropionamide could not inhibit binding of VEGF to PAE-KDR cells under the same conditions (FIG. 5G). Endothelial cells infected with adenovirus expressing TIMP3 with reduced MMP-inhibitory activity (TIMP3Cys1-Ser) also showed reduced binding of VEGF to its cell surfaces (FIG. 5H). This indicated that the inhibition of VEGF binding by TIMP3 was likely to be independent of its MMP-inhibitory activity. Taken together, these results suggest that TIMP3 is capable of specifically and competitively inhibiting VEGF binding to KDR, thereby attenuating receptor activation and downstream signaling. To ensure that TIMP3 was blocking the binding of VEGF to KDR specifically, we conducted cross-linking and immunoprecipitation experiments using KDR antisera. The expected cross-linked monomeric and dimeric KDR receptor forms were recovered from PAE-KDR cells (FIG. 6A), but not in the presence of excess unlabelled VEGF or from PAE-KDR-TIMP3 cells. We ruled out the possibility that TIMP3 induced internalization of surface KDR because the expression of KDR in plasma membrane and lysates of PAE-KDR and PAE-KDR-TIMP3 cells (FIG. 6B) was similar.

TIMP3 Directly Blocks the Interaction Between VEGF and KDR but not FLT1

To determine whether TIMP3 could directly block the interaction between KDR and VEGF, we used an in vitro solid-phase binding assay with soluble KDR-IgG and [125I] VEGF165. Binding of VEGF was decreased in the presence of recombinant TIMP3 (FIG. 6C), in a concentration-dependent manner (FIG. 6D) with an apparent IC50 of 2.9 µg/ml, which is similar to what we observed in PAE-KDR cells. In contrast, similar doses of TIMP3 could not inhibit [125I] VEGF binding to soluble FLT1-IgG (FIG. 5D), indicating the inhibitory effect of TIMP3 to be specific for KDR. These results suggested the possibility of TIMP3 binding to either VEGF or KDR to mediate this inhibition. Solid-phase binding assays using [125I]VEGF and wells coated with KDR-IgG, TIMP1, TIMP2 or TIMP3 did not detect direct binding of VEGF to TIMP3 or any of the other members of the TIMP family (FIG. 6E).

TIMP3 Binds Directly to KDR

To determine whether TIMP3 could interact directly with KDR, we first tested whether TIMP3 and KDR formed a complex on the surface of PAE-KDR-TIMP3 cells. Co-immunoprecipitation experiments with lysates from PAE-KDR and PAE-KDR-TIMP3 cells confirmed this interaction Immunoprecipitation with TIMP3 antisera could pull down KDR protein; reciprocal immunoprecipitation with KDR antisera could pull down TIMP3 protein only in PAE-KDR cells expressing TIMP3 or treated with exogenous recombinant TIMP3 (FIG. 7B). [125I]TIMP3 could be covalently cross-linked to KDR-IgG by bis(sulfosuccinimidyl)suberate (FIG. 7C). In addition, both unlabeled VEGF and TIMP3 (FIG. 7D) could inhibit the binding of labeled TIMP3 to the surface of endothelial cells. To determine if this KDR-TIMP3 interaction occurs in vivo, we conducted immunoprecipitation experiments on extracts of human placenta that are known to be rich in TIMP3 protein. Co-immunoprecipitation experiments confirmed that immunoprecipitation with TIMP3 antisera could pull down KDR and that reciprocal immunoprecipitations with KDR antisera could pull down TIMP3 (FIG. 7E). These data strongly suggest that TIMP3 can bind to KDR in vivo and regulate its interaction with VEGF to inhibit angiogenesis.

Region of TIMP3 Responsible for Angiogenesis Inhibition

Figure 8A:
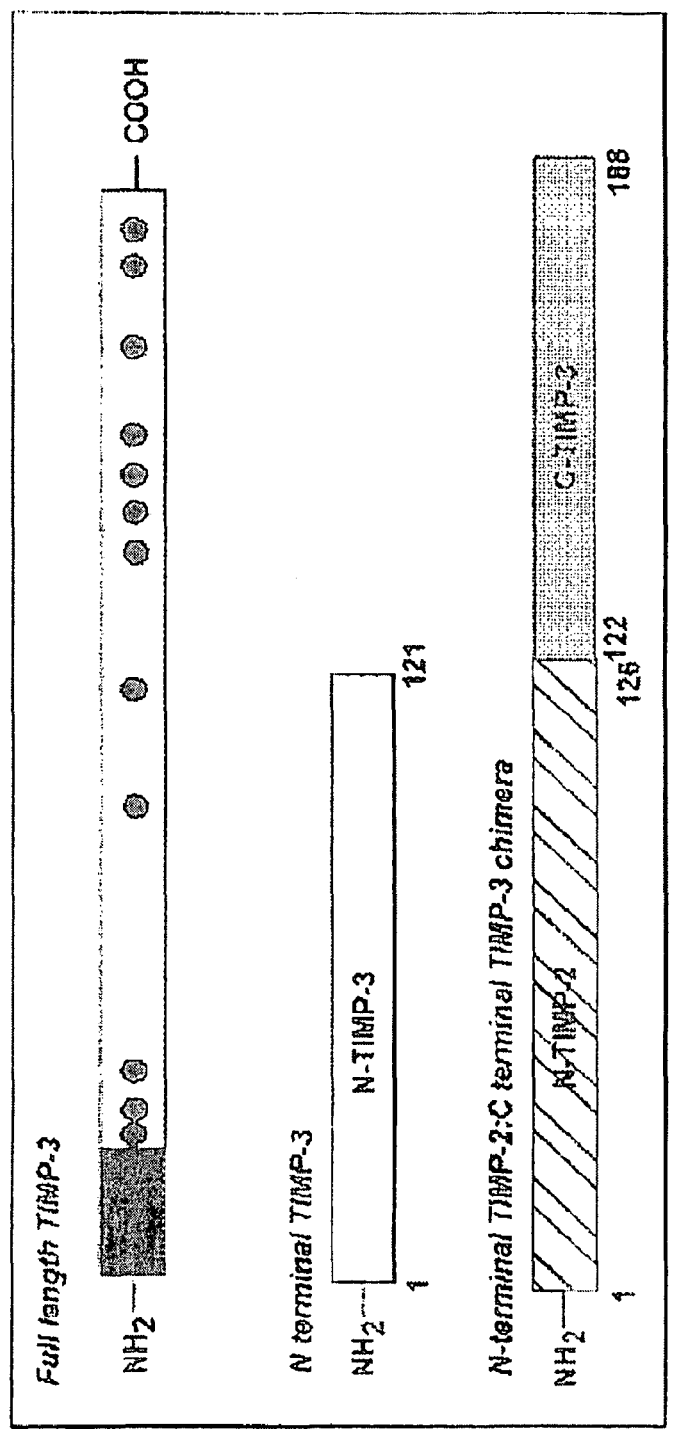
Figure 8B:
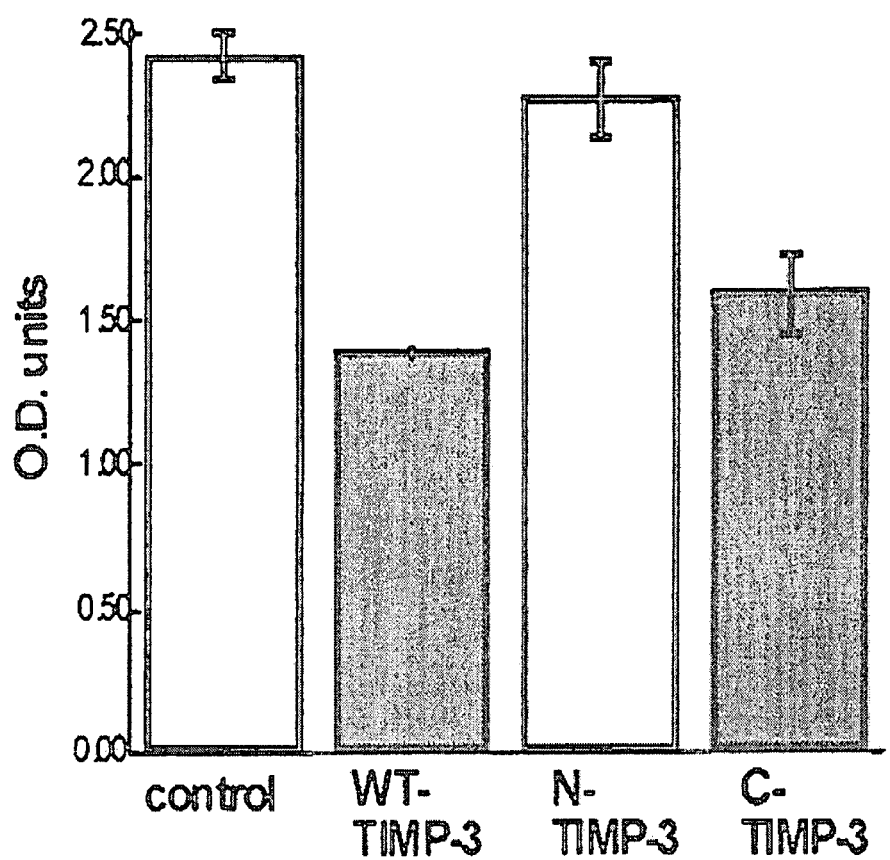

To determine the structural features of the TIMP3 responsible for its anti-angiogenic activity, we used a wild type (wt) TIMP3 (SEQ ID NO:1), and N-terminal domain of TIMP3 (residues 1-121 TIMP3, SEQ ID NO. 6), and an N-terminal TIMP2:C-terminal TIMP3 chimera (SEQ ID NO: 10) representing the isolated C-terminal domain of TIMP3 (residues 1-126 of TIMP-2 (SEQ ID NO: 8) and residues 122-188 of TIMP3 SEQ ID NO. 9) (FIG. 8A). These have purified and tested for their ability to inhibit VEGF binding to KDR (FIG. 8B). Preliminary studies determine that the C-terminal region of TIMP3 is responsible for the angio-inhibitory function of the protein of TIMP3 responsible for the binding to KDR.

Discussion

We discovered that TIMP3 can inhibit angiogenesis by attenuating the binding of VEGF to KDR, thereby inhibiting the downstream signaling pathways necessary to stimulate the cell. This property appeared to be independent of its MMP-inhibitory activity, because other TIMPs (TIMP1 and TIMP2) and synthetic MMP inhibitors could not inhibit the binding of VEGF to KDR in intact cells. TIMP3 could inhibit binding of VEGF to purified soluble KDR in an in vitro system in the absence of cell membranes. In addition, the over-expression of a TIMP3 with reduced activity could inhibit binding of VEGF, a finding that confirmed that MMP inhibition is not required for inhibition of angiogenesis. This inhibition appeared to be specific for VEGF, because signaling by PDGF and bFGF through their receptors was unaffected. A higher dose of TIMP3 (IC50=3.3-4.5 µg/ml) was required to block the binding of VEGF to KDR compared with the dose required to block the biological responses of in vivo angiogenesis, endothelial cell proliferation and migration (0.3-3 µg/ml). Although the difference in the amount of TIMP3 required to induce these effects is probably due to the difference in the sensitivity of readout of the different assays, there is a possibility that TIMP3 might act through two different mechanisms—one at low doses to block the biological responses and the other at a higher dose to compete for binding to KDR. In addition, the inhibition of VEGF binding was specific for KDR with no effect on FLT1. This suggests a unique function for TIMP3 that is independent of its MMP-inhibitory activity. It also suggests a direct specific interaction between TIMP3 and KDR rather than between TIMP3 and VEGF or other receptor-like molecules present on the surface of endothelial cells. We found no evidence of a direct binding of TIMP3 to VEGF, nor could it induce internalization of surface KDR in intact cells. However, in vitro cross-linking analysis showed that TIMP3 could directly bind soluble KDR (KDR-Fc). The affinity of KDR for TIMP3 is weaker than its affinity for VEGF because TIMP3 could inhibit VEGF binding to cells with an IC50 of 3.3-4.5 µg/ml, as compared with 8.5-15 ng/ml for VEGF. TIMP-2 can directly suppress the mitogenic response to tyrosine kinase-type epidermal growth factor (EGF), bFGF and PDGFR-β in an MMP-independent fashion. TIMPs have been shown to alter in vitro cell growth and survival of a variety of cell types, independent of their MMP-inhibitory activity. Thus, TIMPs may be multifunctional, with specific effects based on their localization in tissues.

TIMP3 is a secreted 24-kD protein that distinguishes itself from other members of the TIMP family by its ability to bind to the ECM. In the outer retina, TIMP3 is synthesized by the retinal pigment epithelium (RPE) and deposited into Bruch's membrane. The relationship between the choriocapillaris, Bruch's membrane and the RPE has been a focus of interest to both clinicians and basic scientists for a number of years. The specific localization of KDR at the inner choriocapillaris, facing the RPE, supports the notion that VEGF secreted by the RPE is involved in a physiological paracrine association with the choriocapillaris. By virtue of its angio-inhibitory properties, as well as its presence in Bruch's membrane, a major function can be hypothesized for TIMP3 in the regulation of the angiogenic state of the chorio-capillaris. Sorsby fundus dystrophy is an early-onset, inherited form of macular degeneration, characterized by thickening of Bruch's membrane and submacular neovascularization, which are also features of age-related macular degeneration. Mutations in the TIMP3 gene have been associated with the disease, and increased amounts of the protein were observed in the large sub-retinal deposits in the eye of one patient. TIMP3 levels are elevated in drusen and Bruch's membranes from the eyes of age-related macular degeneration patients. In the same study, TIMP3 immunoreactivity was markedly reduced in areas where choroidal neovascularization was observed, and where the RPE was absent. It is possible that RPE atrophy leads to a decrease in TIMP3 expression, which in turns allows VEGF to bind its receptors on the endothelial cells of the choriocapillaris and promote choroidal neovascularization.

TIMP3 overexpression suppresses primary tumor growth and metastasis. Adenovirally delivered TIMP3 has been shown to have potent antitumor activity as well as a bystander effect in an animal model of human melanoma. Although decreased TIMP3 expression has been observed in a variety of tumor cell lines, its localization in tumor tissue is variable. The expression of TIMP3 in stroma adjacent to cancer cells, as well as a focal concentration around blood vessels in colorectal tumors, might be indicative of a host response to limit and restrict the extent of local tissue degradation, tumor invasion and angiogenesis.

Methods

Cells and Reagents

PAE cell lines expressing KDR, PDGFR-β and fibroblast growth factor receptor- were cultured in Ham's F-12 DMEM supplemented with 10% FBS (Cambrex, East Rutherford, N.J.). Recombinant VEGF121 and bFGF was from R&D Systems (Minneapolis, Minn.); recombinant human PDGF-BB was from Chemicon International (Temecula, Calif.); monoclonal antibodies specific for KDR and PDGFR-β were from Sigma (St Louis, Mo.); MMP-9 and MMP-2 inhibitor (2R)-[(4-biphenylylsulfonyl)amino]-N-hydroxy-3-phenyl-propionamide, MAPK-specific antibody and antibody against phosphorylated MAPK were from Calbiochem (San Diego, Calif.). Recombinant human VEGF165 was a gift from Genentech, B3103 was a gift from British Biotech (Oxford, UK) and TIMP3-specific polyclonal antibody was a gift from S. Apte (Cleveland, Ohio). Recombinant forms of human TIMP1, TIMP2 and TIMP3 were expressed in NSO myeloma cells and purified as described. Monoclonal antibodies against phosphotyrosine (clone 4G10) were purchased from Upstate Biotechnology (Lake Placid, N.Y.).

Generation of TIMP3-Expressing Endothelial Cell Lines

A 550-bp TIMP3 insert from a human cDNA clone was fused in frame with the FLAG epitope DYKDDDK at its C-terminal end and cloned into expression vector pCEP4 (Invitrogen, Carlsbad, Calif.) to be used for transfection.

Adenovirus Infection

Recombinant adenovirus Rad66 containing the cytomegalovirus immediate-early promoter and polyadenylation signal and a wild-type TIMP3 or TIMP3Cys 1-Ser transgene has been described. MS1 mouse endothelial cells\(American Type Culture Collection, Manassas, Va.) were cultured until 80% confluent and infected with adenovirus as described. Cells were infected at 50 or 200 plaque-forming units per cell for 18 h. Medium was then replaced with fresh complete medium and left for 48 h until analysis.

Reverse Zymography

Conditioned medium, cell lysates and ECM fractions from transfected cells were prepared. Equal amounts of protein were loaded onto a 12% gel with 1 mg/ml gelatin plus RPE cell-conditioned medium, as a source of MMPs, for reverse zymography and processed as described.

Immunoprecipitation and Immunoblotting

Serum-deprived cells were pretreated for 30 min with or without 3 µg/ml recombinant TIMP3 and then stimulated for 10 min with the indicated concentrations of ligands. Cell fractions, prepared as described earlier, or immunoprecipitates of the lysates with the indicated antibodies, were subjected to SDS-PAGE. Proteins were detected with horseradish peroxidase-conjugated antibodies specific for either rabbit or mouse IgG (Amersham Pharmacia, Piscataway, N.J.) followed by enhanced chemiluminescence.

Endothelial Cell Migration and Proliferation Assays

A modified Boyden chamber assay for migration and proliferation assays were carried out as described. [H]thymidine incorporation was measured in cells stimulated with 5 ng/ml VEGF for 24 h and subjected for 5 h to the addition of 1 mCi/ml of [3H]thymidine.

CAM Assays

The CAM assay was done as described with slight modifications. Fertilized 3-day-old white Leghorn eggs (Sunnyside, Beaver Dam, Wis.) were cracked and embryos with the yolk intact were placed in glass-bottomed Petri dishes. Methylcellulose disks of 5 mm diameter containing VEGF with or without inhibitors were implanted on the CAM on day 3, injected with India ink and photographed after 3 d. Angiogenesis was reported as the angiogenic index (mean number of tertiary branchpoints from experimental conditions minus the mean number of branchpoints from buffer controls with no angiogenic stimulator).

Radio-Iodination of VEGF165 and TIMP3 and Cross-Linking Experiments

Purified recombinant human VEGF165 or TIMP3 was radiolabeled with $Na^{125}I$ by Iodobeads (Pierce, Rockford, Ill.) to a specific activity of $1.5 \times 10^5$ c.p.m. per ng VEGF or $1.0 \times 10^5$ c.p.m. per ng TIMP3. Ligand-receptor complexes on the cell surface were crosslinked with 0.5 mM disuccinimidyl suberate (Pierce) and analyzed by immunoprecipitation and SDS-PAGE followed by autoradiography. For in vitro assays, radioligand was crosslinked with 250 ng soluble KDR.

Ligand-Binding Experiments

Pre-incubation of PAE cells with unlabeled recombinant TIMPs for 1-2 h at 37° C. was followed by a 2-h incubation with 250-500 pM $[^{125}I]VEGF_{165}$ (specific activity 1,805 Ci/mmol) or $[^{125}I]PDGF$-BB (specific activity 1,325 Ci/mmol; Amersham) on ice. For measurement of Max (maximum number of binding sites) and the $K_d$ value, increasing concentrations of radiolabeled ligand were added to cells that were pre-incubated with or without 30 µg/ml recombinant TIMP3. Data were analyzed by Scatchard plot analyses.

For [125I]VEGF165 binding to soluble KDR or FLT1 receptor (R&D Systems), the wells of 96-well enzyme- and radioimmunoassay strip plates were coated with 100 µl of Fc-specific IgG (8 µg/ml; Sigma). Soluble KDR-Fc or FLT1-Fc (50 ng) was added to each well. After incubation and blocking, the wells were incubated with either (i) 0.8 ng/ml of [125I]VEGF165 in the absence or presence of indicated concentrations of recombinant TIMP3, or (ii) increasing concentrations of [125I]VEGF165 in the absence or presence of 10 µg/ml recombinant TIMP3 for 2 h. After washing, the bound protein was solubilized with 1% SDS and 1 M NaOH and radioactivity measured in a γ-counter.

Statistical Analysis

The statistical significance of differential findings between experimental and control groups was determined by Student's t-test and considered significant if two-tailed P values were <0.05.

Example 2

We synthesized peptide fragments based on the results obtained in Example 1. The following peptides were synthesized based on the following regions from TIMP-3.

```
TIMP-3 Loop-5      KIKSCYYLPCFVTS
                   (SEQ ID NO: 11)

TIMP-3 Loop 6      KNECLWTDMLSNFGYPGYQSKHYACIRQKG
                   (SEQ ID NO: 12)

TIMP-3 Tail        GYCSWYRGWAPPDKSIINATDP
                   (SEQ ID NO: 13)

TIMP-3 N Peptide   RGFTKMPHVQIHTEASESL
                   (SEQ ID NO: 14)
```

These peptides were tested for their ability to inhibit VEGF binding to KDR in vitro. FIG. 9 illustrates a graph showing the results of an assay of the ability of the peptides to inhibit VEGF binding to KDR (VEGFR2). In the assay, 96 well immunoplates were coated with VEG (80 ng/ml) as per standard procedures. Following washing and blocking the binding of sKDR (receptor IgG chimeric protein) to the plates in the presence or absence of peptides was quantified by the detection of binding of enzyme linked anti IgG antibody (ELISA assay. At doses of 3 µM, tail peptide and loop 6 peptide inhibit VEGF binding with the tail peptide inhibiting to the same levels as recombinant TIMP-3.

We also examined the inhibition of VEGF binding by these peptides at lower doses of 0.03 µM and 0.1 µM. FIG. 10 illustrates the results and shows that tail peptide inhibited VEGF binding better than the Loop 6 peptide and the Loop 5 peptide.

Example 3

We next tested the ability of intravitreal TIMP-3 tail and loop 6 peptide to inhibit Choroidal Neovascularization (CNV), a mouse model of age-related macular degeneration (AMD). C57BL6 mice (n=5) in each each group were lasered to induce CNV. On day 3 intravitreal injections [single dose] of control N terminal peptide (116) or TIMP-3 peptides (Tail peptide (SEQ ID NO: 13), Loop 6 (SEQ ID NO: 12), and Loop 5 (SEQ ID NO: 11) were administered. Animals were sacrificed at 14 days following laser and whole mount retinas were examined for evidence of CNV following injection of fluorescein dextran marker.

FIG. 11 illustrates the results of the whole mount retina labeled with fluorescein dextran marker and shows that TIMP-3 peptides inhibit CNV in a mouse model. FIG. 12 illustrates a graph showing the density of the whole mount retina fluorescein dextran marker and shows that TIMP-3 tail and loop 6 peptide inhibit CNV.

Example 4

Introduction

Age-related macular degeneration (AMD) (Congdon et al., Arch. Opthalmol. 122:477-485, 2004; Klein et al., Opthalmology 99:933-943, 1992) is the leading cause of vision loss among people aged 65 and older in the USA. In the exudative form of AMD, the neovascularization arising from the choriocapillaries (choroidal neovascularization, CNV) grows abnormally thorough Bruch's membrane, into the subretinal pigment epithelial (RPE) space and begins to leak blood and fluid resulting in vision loss (Ferris et al., Arch. Opthalmol. 102:1640-1642, 1984; Green, Mol V is 5:27, 1999; Grossniklaus and Green, Am. J. Opthalmol 137:496-503). The molecular mechanism of pathogenesis of choroidal neovascularization (CNV) has not been well defined although a number of studies have suggested Vascular Endothelial Growth Factor (VEGF) to play a role (Baffi et al., Invest. Opthalmol. Vis. Sci. 41:3582-3589, 2000; Kwak et al., Invest. Opthalmol. Vis. Sci. 41:3158-3164, 2000; Lopez et al., Invest. Opthalmol. Vis. Sci. 37:855-868, 1996; Spilsbury et al., J. Pathol. 157:135-144, 2000; Yi et al., Graifes Arch. Clin. Exp. Opthalmol. 235:313-319, 1997).

Sorsby fundus dystrophy (SFD) (Sorsby and Mason, British J. Opthalmology 67-97, 1949) is a dominantly inherited, early onset degenerative disease of the macula which has marked similarities to AMD (Evans, Prog. Retin. Eye Res. 20:227-253, 2001). SFD is of considerable interest as it is the only genetic disorder in which CNV occurs in the majority of affected patients (Holz et al., Retina 14:329-334; Jacobson et al., Nat. Genet. 11:27-32, 1995; Kalmus and Seedburgh, J. Med. Genet. 13:271-276, 1976). SFD is caused by specific mutations in Tissue Inhibitor of Metalloproteinase-3 (TIMP3) gene (Barbazetto et al., Arch. Opthalmol. 123:542-543, 2005; Felbor et al., Arch. Opthalmol 115:1569-1571, 1997; Felbor et al., Hum. Mol. Genet. 4:2415-2416, 1995; Langton et al., J. Biol. Chem. 273:16778-16781, 1998; Langton et al., J. Biol. Chem. 275:27027-27031, 2000; Lin et al., Am. J. Opthalmol. 142:839-848, 2006; Tabata et al., Hum. Genet. 103:179-182, 1998; Weber et al., Nature Genetics 8:352-356, 1994). TIMP3 protein is produced constitutively by retinal pigment epithelial (RPE) cells (Della et al., Invest. Ophthamol. Vis. Sci. 37:1921-1924, 1996; Qi et al., J. Biol. Chem. 30:30, 2002) and is a component of the normal Bruch's membrane (Fariss et al., Am. J. Pathol. 150:323-328, 1997). Functionally, apart from being a key inhibitor of matrix metalloproteinases (MMPs) (Apte et al., J. Biol. Chem. 270:14313-14318, 1995; Pavloff et al., J. Biol. Chem. 267:17321-17326, 1992) and regulating apoptosis in some cells in vitro and in vivo (Ahonen et al., Oncogene 22:2121-2134, 2003; Baker et al., J. Clin. Invest. 101:1478-1487, 1998; Bond et al., J. Biol. Chem. 275:41358-41363, 2000; Fata et al., J. Clin. Invest. 108:831-841, 2001; Mannello and Gazzanelli, Apoptosis 6:479-482, 2001), TIMP3 has been demonstrated to be a potent inhibitor of angiogenesis acting by blocking the binding of VEGF to its VEGFR-2/KDR, and subsequently receptor downstream signaling (Qi et al., Nat. Med. 9:407-415, 2003). SFD-TIMP3 protein is also localized to the Bruch's membrane (Fariss et al., Br. J. Opthalmol. 82:1329-1334, 1998) and shows pro-apoptotic activity (Majid et al., FEBS Lett 529:281-285, 2002) but has reduced MMP inhibitory activity and may promote angiogenesis (Qi et al., 2002). Whether SFD-TIMP3 affects VEGFR-2 mediated VEGF signaling specific to angiogenesis is unknown. In this study, we have generated endothelial cells (ECs) expressing SFD-related S156C TIMP3 mutation as a platform and determined how mutant TIMP3 regulates VEGF signaling via VEGFR-2 during SFD-related angiogenesis.

Materials and Methods

Materials

Porcine Aortic Endothelial (PAE and PAEKDR) cells were cultured in Ham's F-12/DMEM medium supplemented with 10% fetal bovine serum (FBS) (Hyclone), 50 unit/ml penicillin and 50 µg/ml streptomycin as described previously (Qi et al., 2002). Recombinant human VEGF was a kind gift from Genentech, CA. Antibodies: monoclonal anti-TIMP3 antibody (Chemicon International, Inc., Temecula, Calif.), monoclonal anti-Flk-1 (A-3), goat polyclonal anti-actin (C-11), and bovine anti-goat 1gG-HRP (Santa Cruz Biotechnology, Inc), polyclonal phospho-VEGF receptor-2/3 (Ab-1) antibody (Oncogen™ Research Products), monoclonal anti-VEGF receptor-2 (KDR), Clone KDR-2, (Sigma), MAPK and phospho-specific MAPK antibodies (Calbiochem-Novabiochem Corporation), HRP-conjugated anti-rabbit and anti-mouse IgG antibodies (Amersham Pharmacia Biotech).

Generation of EC Cell Lines Expressing Wild-Type or S156C Mutant TIMP3.

A 550 by Timp-3 or S156C Timp3 insert from a human cDNA clone was cloned into expression vector pCEP4 (Invitrogen, Carlsbad, Calif.). PAEKDR cells were transfected with TIMP3 cDNA or empty vector using Lipofectamine reagent (Gibco-BRL Rockville, Md.). Stable clones were isolated using Hygromycin selection. RT-PCR, Western blot and reverse zymography were used to identify and analyze the expression of TIMP3 or mutant TIMP-3, respectively.

RT-PCR.

Total RNA was extracted from the cells by using Totally RNA™ Kit (Amibion Inc. Austin, Tex.). RT-PCR was performed using a RETROscript™ First Strand Synthesis Kit (Amibion Inc., Austin, Tex.). 10 ng of total RNA was used for RT and amplication. The sequences of the PCR primer pairs for human VEGFR-2 or TIMP3 gene were: 5'-CTT CGA AGC ATC AGC ATA AGA AAC T-3' (forward) (SEQ ID NO: 15) and 5'-TGG TCA TCA GCC CAC TGG AT-3'(reverse) (SEQ ID NO: 16), and 5'-CTC TGC AAC TCC GAC ATC GTG AT-3'(forward) (SEQ ID NO: 17), and 5'-CAG CAG GTA CTG GTA CTT GTT GAC-3'(reverse) (SEQ ID NO: 18). 28S primers (forward, 5'-GTT CAC CCA CTA ATA GGG AAC GTG A-3'(SEQ ID NO: 19), and reverse, 5'-GAT TCT GAC TTA GAG GCG TTC AGT-3') (SEQ ID NO: 20) were used as a control for RNA expression. PCR conditions were 94° C. for 3 min, followed by 30 cycles (94° C., 30 s; 55° C., 30 s; 72° C., 1 min), and a final extension step of 72° C. for 5.

Preparation of Cellular Fractions.

2 day serum free conditioned medium (CM) was collected from subconfluent cells cultured on six-well plates (Costar). In some cases the CM was further concentrated with heparin-agarose gels (Bio-rad). The cell monolayer was dislodged from the culture plates following a 10 min incubation in Ca2+, Mg2+ free phosphate buffered saline (PBS) containing 2.5 mM EDTA. After several rinses in PBS and water, the ECM was scraped in a small volume of electrophoresis sample buffer without reducing agent for analyses. Plasma membrane (PM) fractions were prepared from cells centrifuged at 500 g and 4° C. for 5 min The supernatant was discarded and the cell pellets were resuspended in PBS containing protease inhibitors, lysed with a 26-gauge syringe needle, and centrifuged at 3,000 g at 4° C. for 15 minutes. The supernatant was centrifuged at 800,000 g at 4° C. for 1 hr. The PM pellets were suspended in lysis buffer containing protease inhibitors. In some instances the membrane fraction of cells was prepared using ProteoExtract Subcellular Proteome Extaction Kit (EMD Biosciences, Inc).

Ligand Binding Assay.

1×106 cells/well in 12 well plates were incubated with the indicated concentrations of 125I-VEGF165 (specific activity, 1,805 Ci/mmol, Amersham) in the presence or absence of 50-fold excess of unlabeled VEGF for 2 h on ice. After washing, the cell monolayers were solubilized with lysis buffer (20 mM Tris HCl pH 7.5, 1% triton X 100 and 10% glycerol), and the radioactivity measured in a gamma counter.

Immunoprecipitation and Immunoblotting.

Cell fractions or immunoprecipitates of the lysates with the indicated antibodies were subjected to SDS-PAGE. Proteins were detected with either a HRP-conjugated anti-rabbit or anti mouse IgG antibody (Amersham Pharmacia Biotech., Piscataway, N.J.) followed by ECL. The blots were restripped with Western ReProbe™ solution (Genotech) for 30 minutes and reprobed as indicated.

Reverse Zymography.

Conditioned medium, cell lysates and ECM fractions from transfected cells were prepared as described previously (Qi et al., 2002). Equal amounts of protein were loaded onto a 12% gel with 1 mg/ml gelatin plus RPE cell-conditioned media, as a source of MMPs, for reverse zymography and processed as described previously (Pavloff et al., 1992).

Immunofluorescence Staining Analyses.

For immunostaining, subconfluent cells cultured on Falcon cultureslides (BD, Biosciences) were used. For surface KDR detection, cells were fixed in 1% paraformaldehyde for 10 min at 4° C. Following blocking with 1% BSA cells were incubated with anti-extracellular VEGFR-2 monoclonal antibody for 1 h at room temperature. Surface KDR was detected with biotinylated anti-mouse 1 g G (1:1000) and Texas Red avidin D (1:1500) using standard procedures. For actin reorganization cells were stimulated for 15 min at 37° C. with 50 ng/ml VEGF or control buffer. The cells were fixed with 3.7% paraformaldehyde in PBS for 30 min at 4° C. and permeabilized with 0.2 Triton X-100 for 20 min at room temperature. Following rinsing with PBS the cells were incubated with fluorescein isothiocyanate (FITC)-labeled phalloidin in PBS (0.66 µg/ml, Sigma) for 20 min at room temperature washed with PBS and analyzed by fluorescence microscopy.

Enzyme-Linked Immunoassay (ELISA).

VEGF, bFGF and soluble VEGFR-2 levels in the conditioned media were measured by ELISA Kit according to the manufacturer's protocol (R&D.).

Proliferation Assay.

Cells were seeded at a density of 5000 cells/well in 24 well culture plates and cultured for 24 h in growth medium. After synchronization overnight in serum-free medium supplemented with 0.1% BSA (Sigma), cells were stimulated with or without VEGF for 36 h, followed by the addition of 0.4 µCi/ml of [3H]thymidine for 4 h. High molecular weight DNA was precipitated using 5% trichloroacetic acid at 4° C. for 30 min After two washes with ice-cold H2O, 3H radioactivity was solubilized in 1 N NaOH for 20 min at room temperature, acidified by addition of 2 N HCl, and measured using a liquid scintillation counter. Each sample was assayed in triplicate and the assays were repeated at least twice.

Migration Assay.

A modified Boyden chamber assay was carried out as described previously 34. Briefly, 8.0 µm pore PVPF polycarbonate membranes were pre-coated with 100 µg/ml collagen type I in 0.2 N acetic acid (Cohesion technologies, INC. Pala Alto, Calif.). VEGF at the indicated concentrations was placed in the lower chamber, and cells (2×106) in serum-free medium were placed in the upper chambers. Chamber was then incubated for 4 hrs at 37° C. in a 5% CO2 humidified incubator. Cells remaining on the top of the filter were removed. Cells on the bottom surface of the filter were fixed, stained and mounted. The number of migrating cells per well was counted microscopically.

Tube Formation Assay.

Type 1 collagen was mixed with 10×DMEM and 0.1 M NaOH (8:1:1), adjusted to a solution containing 10 µg/ml growth factor reduced matrigel matrix (BD, Biosciences), and then distributed in 48-well dishes. After gelling, serum-starved cells were seeded on the collagen gels at 1.5×104 cells/well, and maintained in serum-free medium in the presence or absence of 50 ng/ml VEGF or RPE cell-conditioned media. After 4 h of incubation at 37° C., a second layer of collagen was added, and cultures were kept under the same conditions as above described. Tube formation was examined using a phase-contrast microscopy at the indicated time points.

Statistical Analysis.

The p values were calculated from Student's t test using comparisons with control samples tested at the same time.

Results

S156C TIMP3 is Abnormally Distributed in Endothelial Cells.

Stable endothelial cell lines (PAEKDR) expressing wild-type (WT) or S156C mutant TIMP3 cDNA or vector alone were generated. Two independent clones expressing similar levels of mRNA (identified by RTPCR) encoding WT (W1, W4) or mutant TIMP3 (M7, M10) were identified (FIG. 13A). Endogenous TIMP3 mRNA was detected in other endothelial cell lines including monkey choroidal endothelial cells, CRL-1780. RT-PCR was used to ascertain that the independent clones utilized in this study expressed similar levels of KDR and 28S RNA (FIG. 13A). This indicated that neither WT nor mutant TIMP3 affected transcriptional activation of KDR. Western Blot analysis using monoclonal antibodies against TIMP3 determined that WT-TIMP3 was predominantly localized in the extracellular matrix (ECM) in a 23-kDa form with a very smaller fraction being secreted into the conditioned medium (CM) (FIG. 13B), confirming previous reports that TIMP3 is an ECM bound protein in endothelial cells (Qi et al., Nat. Med. 9:407-415, 2003). On the other hand, mutant S156 TIMP 3 was detected predominantly in the CM as a 28-kDa protein (FIG. 13B) suggesting a possible reduced ECM binding property for the mutant protein. To determine if the higher molecular weight form of mutant TIMP-3 was a result of glycosylation, samples were treated with PNGase F (an amidase which removes N-linked glycoproteins) prior to analyses. This treatment resulted in a conversion to the 23 kDa form (FIG. 13C), which suggests that the 28-kDa protein is a glycosylated variant of mutant TIMP3. The spatial expression of mutant TIMP3 and its molecular mass species in endothelial cells are distinct from those observed in RPE cells (Qi et al., 2002: Langton et al., Hum. Mol. Genet. 14:3579-3586, 2005). The reason for this discrepancy is likely due to unique distributions and expressions in different cell types. The MMP inhibitory activity of WT and mutant TIMP3 was further analyzed by reverse zymography. ECM and CM of PAEKDR cells expressing WT-TIMP3 (W1, W4) showed a marked MMP inhibitory species with an approximate molecular mass of 23-kDa corresponding to the protein visualized on western blot (FIG. 13D). However, the cells expressing mutant TIMP3 (M cells) exhibited minimal MMP inhibitory activity in CM or ECM samples (FIG. 13D) similar to our previous observations in RPE cells (Qi et al., 2002). A similar result was obtained by western blot analyses (FIG. 13E) and reverse zymography (FIG. 13F) of heparin-agarose concentrated the CM (FIG. 13B). These results indicate that mutant S156-TIMP3 exhibits characteristics of an abnormal protein, including reduced binding to the ECM of endothelial cells in addition to a reduction in MMP inhibitory activity.

S156C TIMP3 Expression in ECs Increases VEGF Binding to KDR.

To determine whether expression of mutant TIMP3 regulates the interaction of VEGF with VEGFR-2, we examined VEGF binding in parental PAE and the transfected PAEKDR cell lines using a [125I] VEGF binding assay. Mock cells (V, PAEKDR cells transfected with empty vector) but not parental PAE (P, ECs not expressing KDR) cells showed a specific concentration dependent [125I]VEGF binding. As we have shown previously, WT-TIMP3 expression dramatically inhibited the binding of [125I] VEGF to KDR, with a downward shift of the concentration-binding curve (FIGS. 14A,B). Surprisingly, the expression of mutant TIMP3 resulted in a 2-3 fold increase in [125I] VEGF binding with an upward shift in the concentration-binding curve (FIGS. 14A,B).

S156C TIMP3 Expression in ECs Accentuates VEGFR-2 Signaling Via Elevated Receptor Levels.

Since mutant cells had increased VEGF binding to VEGFR-2, we tested whether these cells had elevated levels of functional VEGFR-2 on their surface. Western blot analysis using a phospho-VEGF receptor-2/3 polyclonal antibody demonstrated that VEGF stimulated the tyrosine phosphorylation of a 210-kDa KDR protein in membrane fractions prepared from both mock transfected cells (V) and mutant cells (M) (Data not shown). However, the level of phosphorylated KDR detected in mutant cells after VEGF stimulation was consistently ~2 fold higher than those observed in mock cells (Data not shown). In contrast, as reported previously no receptor autophosphorylation was seen in WT-TIMP3 cells (Data not shown). Western blot analysis with monoclonal antibody directed against the C-terminus of VEGFR-2 (C-term VEGFR-2 mAb) was used to detect total KDR levels in membrane fractions. Mock cells showed a mature form of KDR corresponding to a molecular size of 210-kDa that phosphorylated in response to VEGF. In addition two other receptor forms (a 200-kDa precursor and smaller fragment at ~160 kDa) were also observed that were not phosphorylated (Data not shown). These bands were also detected in receptor immunoprecipitates prepared with total lysates isolated from PAE/KDR (Data not shown). consistent with those previously reported for KDR (Waltenberger et al., Circulation 94:1647-1654, 1996). To determine whether these receptor isoforms represent full-length VEGFR-2, the total lysates were immunoprecipitated with C-term VEGFR-2 mAb, and the immunoprecipitates were separated on SDS-PAGE, and subjected to Western blot analysis with monoclonal antibodies directed against the extracellular domain of VEGF receptor-2 (clone KDR-2). Clone KDR-2 recognized the 160-, 200- and 210-kDa KDR isoforms immunoprecipitated with the C-term VEGFR-2 mAb (Data not shown). There was a marked increase in intensity of the mature form and smaller fragment of receptor in mutant cells, whereas a similar level of the mature form was seen in WT-TIMP3 cells, but the smaller fragment was missing (Data not shown). WT- and mutant TIMP3 expression did not affect KDR receptor precursor levels (Data not shown). To further confirm that surface KDR is elevated in mutant cells, we labeled PAEKDR cells with clone KDR-2 antibody and analyzed the distribution of surface KDR by immunofluorescence staining assay. Cells expressing S156C mutant TIMP-3 showed increased fluorescent labeling for surface KDR (Data not shown) relative to cells expressing empty vector or WT-TIMP3. In vitro studies have determined that the soluble VEGFR-2 fragment (sKDR) can be found in the CM of endothelial cells, suggesting that it may be secreted, similar to sflt-1, or proteolytically cleaved from cells. To investigate whether sKDR is related to elevated KDR on the surface of mutant cells, we measure sKDR levels in the CM of cells using ELISA. A significant amount of sKDR was observed in the CM of mock cells, but not in parental PAE cells. Interestingly, mutant cells showed 7- to 8-fold more cleaved sVEGFR-2 in the CM, whereas WT-TIMP3 cells showed 10 fold less than mock cells (Data not shown). Overall, these data indicate that mutant TIMP3 potentiates VEGF-stimulated tyrosine phosphorylation of KDR via elevated receptor levels on cell surface.

Activation of MAP kinase is a known activated VEGFR-2 downstream signaling event. We measured the phosphorylation of two MAP kinases, ERK1 (p44) and ERK2 (p42) by western blot analysis of membrane fractions in WT and mutant ECs. VEGF stimulated the phosphorylation of ERK1/2 in mock cells (V), but not in WT-TIMP3 cells (Data not shown). Interestingly, the VEGF-stimulated ERK1/2 phosphorylation was increased by 2-3 fold in mutant cells (Data not shown) while the expression of WT and mutant TIMP3 had no impact on total ERK1/2 levels. These results determine that elevated phosphorylated KDR in mutant cells is associated with enhanced activation of ERK1/2.

S156C TIMP3 Enhances VEGF-Stimulated Migration and Actin Reorganization, but not Proliferation.

Figure 15C:
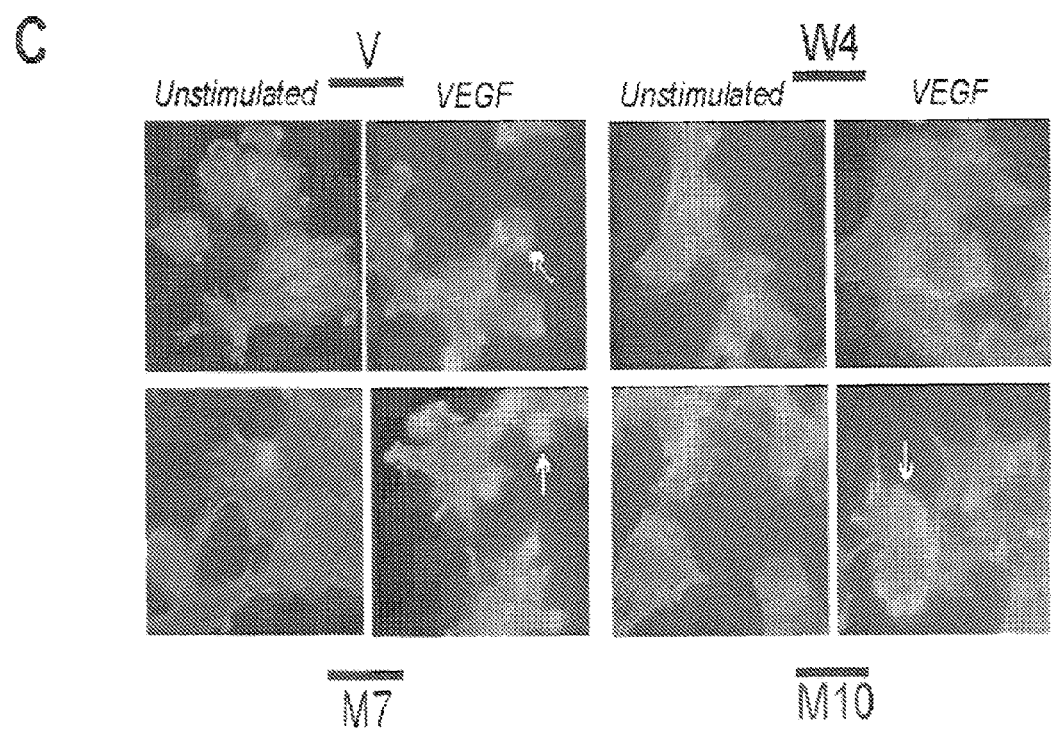

To investigate whether elevated VEGFR-2 signaling in cells expressing mutant TIMP3 could be translated into enhanced biological responses, we examined VEGF-stimulated proliferation and migration, two critical steps in the angiogenic process, in the transfected PAEKDR cell lines. Quiescent endothelial cells were stimulated with VEGF, and evaluated by incorporation of [3H] thymidine. As shown in FIG. 15A, VEGF stimulated the proliferation of mock cells in a concentration-dependent fashion with a maximum activity at 15 ng/ml. Mutant cells exhibited similar mitogenic responses to VEGF, whereas WT-TIMP3 cells showed a dramatic attenuation in the VEGF response (FIG. 15C), indicating that mutant TIMP3 is an inefficient inhibitor of VEGF-stimulated EC proliferation.

A mini-Boyden chamber assay was used to examine VEGF-stimulated cell migration. VEGF stimulated a concentration-dependent migratory response in mock cells with a maximum effect at 50 ng/ml (FIG. 15B). While WT-TIMP3 expression but not mutant TIMP3 dramatically reduced basal and VEGF-stimulated migration. Mutant TIMP3 expressing cells had an accentuated migratory response towards VEGF (FIG. 15B). EC migration involves reorganization of the actin cytoskeleton with the formation of veil-like dense structures at the cell margin, denoted membrane edge ruffles, have previously been shown to be an integral part of cellular motility. We analyzed VEGF-stimulated formation of membrane ruffles in the PAEKDR cell lines. Treatment of quiescent cells with VEGF for 15 min resulted in the formation membrane ruffles in a small percentage of mock transfected cells (V) (FIG. 15C) while a majority of mutant cells showed more striking edge ruffles (FIG. 15C). In contrast, WT-TIMP3 cells (FIG. 15C) did not form membrane ruffles in response to VEGF. These data provide convincing evidence that mutant TIMP3 is an enhancer of VEGF-induced EC migration.

S156C TIMP3 Increases Differentiation but not Survival During VEGF Dependent Tube Formation.

An in vitro angiogenesis assay using a type1 collagen substrate was employed to study whether mutant TIMP3 affected VEGF-stimulated tube formation, which recapitulates the later stages of angiogenesis. In this assay, cells were grown in three-dimensional collagen gels in the presence or absence of VEGF for up to 14 days in culture. After 24 h, VEGF stimulated the differentiation of mock cells to form tube-like structures that survived over the 8 days of culture (FIG. 16). In contrast, the ability of WT-TIMP3 cells to form tube-like structures was severely compromised (FIG. 16). However, mutant cells treated with VEGF organized rapidly, forming extensive tubular networks, but by day 5 the tubular structures started to regress and collapse. Both WT-TIMP3 and mutant cells exhibited morphologic features characteristic of cell death relative to mock cells under basal conditions (FIG. 16).

Retinal pigment epithelium (RPE) secretes angiogenic growth factors and inhibitors including bFGF and VEGF. RPE plays a critical role in maintaining the highly vascularized and permeable fenestrated choriocapillaris and is also involved in the pathogenesis of CNV in AMD (Blaauwgeers et al., Am. J. Pathol. 155:421-428, 1999; Marneros et al., Am. J. Pathol. 167:1451-1459, 2005). Since RPE-derived VEGF was shown to stimulate tube formation of the underlying endothelial cells we tested whether RPE cells mediate an enhanced tube formation in mutant cells. Conditioned medium (CM) from RPE cells were collected and added to all transfected PAEKDR cell lines and parental PAE cells cultured in 3-D collagen gels. As with VEGF, the CM induced a similar pattern of tubular morphogenesis in mock and mutant cells, and had no effect on WT cells. The CM also failed to stimulate tube formation in parental PAE cells. ELISA demonstrated that the amount of VEGF was much higher than that of bFGF (543±8 pg/ml/mg protein vs 24±8) in the CM. These data suggest that mutant TIMP3 might potentiate RPE-driven angiogenesis by increasing VEGF signaling via elevated VEGFR-2.

Discussion

Sorsby Fundus Dystrophy (SFD) is a rare autosomal dominant, fully penetrant disease that commonly manifests as an early onset hemorrhagic maculopathy secondary to choroidal neovascularization (CNV) (Sorsby and Mason, 1949). The onset of symptoms typically occurs in the third to fifth decades of life with rapidly evolving loss of central vision or increasing nyctalopia (night blindness) over the course of several years (Capon et al., Eye 2:114-122, 1988; Polkinghorne et al., Opthalmology 96:1763-1768, 1989). The clinical features of SFD very closely resemble those of age-related macular degeneration (AMD) being distinguished from each other primarily on the basis of age of onset of symptoms and family history. Given that mutations in TIMP3 cause SFD, it is important to determine the role played by TIMP3 protein in patho-physiological responses of the retina.

This study has shown that the expression of mutant S156C-TIMP3 augments VEGF induced angiogenesis in vascular endothelial cells that is mediated by elevated levels and activation of functional surface VEGFR-2/KDR and could potentially play a crucial role in the development of CNV in the disease. There has been an increasing debate on whether the SFD mutant TIMP3 results in a loss of function, gain of function or dominant-negative effect for the protein (Li et al., Expert Rev. Mol. Med. 7:1-15, 2005).

The identification of TIMP3 as an endogenous inhibitor of VEGFR-2-mediated angiogenesis (Qi et al., 2003) led us to postulate that S156C TIMP3, a mutation that results in an earlier onset phenotype as well as prominent CNV, might be deficient in this function. Unexpectedly, S156CTIMP3 expression resulted in an increase in the levels of the mature form of KDR protein in the membrane fraction, concomitant with an increase of soluble KDR in the conditioned medium. Elevated membrane-associated KDR was sufficient to increase VEGF binding and subsequent KDR autophosphorylation and MAP kinase phosphorylation with downstream consequences of enhanced VEGF-dependent migration and tube formation in vitro. It should be noted that S156CTIMP3 protein did not augment VEGF-dependent proliferation or the survival phase of in vitro angiogenesis. The exact molecular mechanism by which S156C TIMP3 increases membrane-associated KDR is unknown. In PAE-KDR cells, the KDR protein is expressed under the control of the human cytomegalovirus promoter. The expression of mutant TIMP3 results in an increase in membrane-bound KDR protein in endothelial cells, while the relative amount of specific mRNA level remains stable suggesting a post-transcriptional upregulation of the receptor level independent of the KDR promoter, similar to that observed previously in PAE/KDR cells cultured under hypoxic conditions (Waltenberger et al., 1996).

Pulse-chase experiments have revealed that KDR/Flk-1 is initially synthesized as an immature 150-kDa protein and rapidly glycosylated to a 200-kDa intermediate form, and further glycosylated at a slower rate to a mature 230-kDa protein that is expressed on the cell surface (Takahashi and Shibuya, Oncogene 14:2079-2089, 1997). Our studies confirmed the presence of three KDR isoforms on the surface of PAEKDR cells. In addition to the mature protein, mutant TIMP3 markedly increased the levels of the immature form, whereas cells expressing WT-TIMP3 had reduced levels of this immature form with no effect on the intermediate and mature forms. These data indicate that WT and mutant TIMP3 have distinctive effects on the early steps of maturation of the receptor. It has been recently reported that novel highly efficient intrabodies can bind newly synthesized KDR in the endoplasmic reticulum and block receptor transport to the cell surface (Boldicke et al., J. Immunol. Methods, 300: 146-159, 2005; Boldicke et al., J. Cell Mol. Med. 11:54-70, 2007). It is an interesting possibility that WT and mutant TIMP3 may differentially affect immature receptor translocation via distinct interactions with newly synthesized KDR in the endoplasmic reticulum. In addition, it has been also suggested that β3 integrin negatively regulates VEGFR-2 expression (Reynolds et al., Nat. Med. 8:27-34, 2002) and that caveolin plays a role in KDR internalization (Labrecque et al., Mol. Biol. Cell 14:334-347, 2003). The role of TIMP-3 in these mechanisms is unknown.

The ADAMs (a disintegrin and metalloproteinases) family of membrane-spanning proteins combines features of both adhesion molecules and proteinases (Blobel, Cell 90:589-592, 1997). ADAM-17 (TACE), the sole mammalian cell surface-associated metalloproteinase sheddase so far identified, can affect the shedding of transmembrane-anchored proteins, such as TNF-α (Black et al., Nature 385:729-733, 1997), L-selectin (Borland et al., J. Biol. Chem. 274:2810-2815, 1999) and interleukin-6 receptor (Hargreaves et al., Br. J. Haematol. 101:694-702, 1998) that are sensitive to TIMP3. A TIMP3-sensitive metalloproteinase also mediates the shedding of transmembrane protein syndecan-1 (Fitzgerald et al., J. Cell Biol. 148:811-824). Since VEGFR-2 can be proteolytically, cleaved from endothelial cells (Ebos et al., Mol. Cancer res. 2:315-326, 2004) and SFD mutant TIMP3 has attenuated MMP inhibitory activities, we hypothesized that mutant TIMP3 could regulate the shedding of KDR from endothelial cells. Our data suggests that a TIMP3-sensitive sheddase mediates KDR shedding in endothelial cells. Conversely, the presence of mutant TIMP3 increased KDR shedding, indicating that mutant TIMP3 could activate the KDR sheddase. Although it is not clear whether the KDR sheddase is a known TACE or syndecan sheddase, our results are in contrast to the finding that syndecan-1 shedding is concomitant with the loss of surface syndecan-1. In our case, KDR sheddase-mediated KDR shedding is accompanied by increased surface KDR, suggesting that other mechanisms may be simultaneously involved.

Taken together, these data indicate that the upregulation of surface KDR by mutant TIMP3 is a dynamic process the exact molecular mechanism(s) by which this occurs remains to be determined.

Ten independent mutations resulting in SFD have been identified to date. Seven of the ten mutations introduce a new cysteine residue at the C-terminus (S156C, G166C, G167C, Y168C, S170C, Y172C and S181C). The E139X mutation which introduces a stop codon at residue 139 results in an odd number of cysteine residues at the C-terminus The last 2 mutations, a mutation of the intron4/exon5 splice acceptor site as well as His158Arg mutation do not create a cysteine residue. Previous studies have reported that some TIMP3 mutations gave rise to several additional higher molecular mass protein complexes (possibly TIMP3 dimers) that retained their ability to inhibit MMPs and localized to the ECM when expressed in COS7 cells (Langton et al., 2002). Higher molecular weight complexes were also detected in mutant murine TIMP3 S156C/S156C fibroblast cells, but lost their inhibitory activity (Soboleva et al., J. Cell Physiol. 197: 149-156). In contrast to these findings, we have detected a heavily glycosylated variant of mutant TIMP3 protein with reduced MMP inhibitory activity and attenuated binding to ECM in endothelial cells. The discrepancy between previous reports and ours is most likely due to differences in cell type examined. Reduced binding of mutant TIMP3 to the ECM could be a result of an excessive glycosylation, which can potentially decrease its apparent affinity for the ECM, presumably by making basic residues (Langton et al., J. Biol. Chem. 273:16778-16781, 1998). Excessive glycosylation might also lead to a reduction of MMP inhibitory activity of mutant TIMP3, presumably by a conformation change or reduced ECM binding (Butler et al., J. Biol. Chem. 274: 10846-10851, 1999). Indeed, our data have shown that the unglycosylated form of mutant TIMP3 in the ECM, but not the glycosylated form in the conditioned medium retained some MMP inhibitory activity. We have previously demonstrated that expression of S156CTIMP3 in human RPE cell line results in reduced inhibition of MMPs and increased activation of MMP2 and MMP9 (Qi et al., 2002). More recently, the inability of S156C mutation to inhibit MT1-MMP activation of pro-MMP2 has been confirmed independently, in addition to the finding of accumulation of a turnover-resistant fraction of mutant TIMP-3 protein in RPE cells (Langton et al., 2005).

In summary, we have shown that SFD S156C mutation specifically and dynamically upregulates surface KDR level and activity resulting in enhanced VEGF-dependent angiogenesis. This points to a novel mechanism for the regulation of angiogenesis by S156C TIMP3 in SFD. Systemic bevacizumab has been recently shown to be a promising treatment option for CNV in a patient with SFD (Prager et al., Acta Opthalmol Scand, 2007). Our data also show that S156CTIMP3 is highly glycosylated, soluble and inefficient in MMP inhibitory activity suggesting that in addition to anti VEGF therapies, MMP inhibitors might provide therapeutic benefit.

Having described the invention, the following is claimed:

1. A method of inhibiting aberrant angiogenesis in a subject, comprising: administering to cells of the subject expressing vascular endothelial growth factor receptor 2 (VEGFR2) contributing to the aberrant angiogenesis a composition comprising a biologically effective amount of a polypeptide, the polypeptide consisting of the amino acid sequence of SEQ ID NO:11, SEQ ID NO:12 or SEQ ID NO:13.

* * * * *

SEQUENCE LISTING

<160> NUMBER OF SEQ ID NOS: 20

<210> SEQ ID NO 1
<211> LENGTH: 211
<212> TYPE: PRT
<213> ORGANISM: Homo sapiens -continued

```
<400> SEQUENCE: 1

Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 2
<211> LENGTH: 91
<212> TYPE: PRT
<213> ORGANISM: Homo sapiens

<400> SEQUENCE: 2

Val Glu Arg Trp Asp Gln Leu Thr Leu Ser Gln Arg Lys Gly Leu Asn
1               5                   10                  15

Tyr Arg Tyr His Leu Gly Cys Asn Cys Lys Ile Lys Ser Cys Tyr Tyr
            20                  25                  30

Leu Pro Cys Phe Val Thr Ser Lys Asn Glu Cys Leu Trp Thr Asp Met
        35                  40                  45

Leu Ser Asn Phe Gly Tyr Pro Gly Tyr Gln Ser Lys His Tyr Ala Cys
    50                  55                  60

Ile Arg Gln Lys Gly Gly Tyr Cys Ser Trp Tyr Arg Gly Trp Ala Pro
65                  70                  75                  80

Pro Asp Lys Ser Ile Ile Asn Ala Thr Asp Pro
                85                  90

<210> SEQ ID NO 3
<211> LENGTH: 120
<212> TYPE: PRT
<213> ORGANISM: Homo sapiens

<400> SEQUENCE: 3

Met Thr Pro Trp Leu Gly Leu Ile Val Leu Leu Gly Ser Trp Ser Leu
1               5                   10                  15
```

```
Gly Asp Trp Gly Ala Glu Ala Cys Thr Cys Ser Pro Ser His Pro Gln
             20                  25                  30

Asp Ala Phe Cys Asn Ser Asp Ile Val Ile Arg Ala Lys Val Val Gly
         35                  40                  45

Lys Lys Leu Val Lys Glu Gly Pro Phe Gly Thr Leu Val Tyr Thr Ile
 50                  55                  60

Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
             85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe
            115                 120

<210> SEQ ID NO 4
<211> LENGTH: 1240
<212> TYPE: DNA
<213> ORGANISM: Homo sapiens

<400> SEQUENCE: 4
ggcggcgggc gctcagacgg cttctcctcc tcctcttgct cctccaagct cctgctcctt    60
cgccgggagc ccgccgccg agtcctgcgc cagcgccgag gcagcctcgc tgcgcccat    120 cccgtcccgc cgggcactcg gagggcagcg cgccggaggc caaggttgcc ccgcacggcc   180
cggcgggcga gcgagctcgg gctgcagcag ccccgccggc ggcgcgcacg gcaactttgg   240
agaggcgagc agcagccccg gcagcggcgg cagcagcggc aatgacccct tggctcgggc   300
tcatcgtgct cctgggcagc tggagcctgg gggactgggg cgccgaggcg tgcacatgct   360
cgcccagcca cccccaggac gccttctgca actccgacat cgtgatccgg gccaaggtgg   420
tggggaagaa gctggtaaag gagggccct tcggcacgct ggtctacacc atcaagcaga   480
tgaagatgta ccgaggcttc accaagatgc ccatgtgca gtacatccat acggaagctt   540
ccgagagtct ctgtggcctt aagctggagg tcaacaagta ccagtacctg ctgacaggtc   600
gcgtctatga tggcaagatg tacacggggc tgtgcaactt cgtggagagg tgggaccagc   660
tcaccctctc ccagcgcaag gggctgaact atcggtatca cctgggttgt aactgcaaga   720
tcaagtcctg ctactacctg ccttgctttg tgacttccaa gaacgagtgt ctctggaccg   780
acatgctctc caatttcggt taccctggct accagtccaa acactacgcc tgcatccggc   840
agaagggcgg ctactgcagc tggtaccgag gatgggcccc ccggataaa agcatcatca   900 atgccacaga cccctgagcg ccagaccctg ccccacctca cttccctccc ttcccgctga   960
gcttcccttg gacactaact cttcccagat gatgacaatg aaattagtgc ctgttttctt  1020
gcaaatttag cacttggaac atttaaagaa aggtctatgc tgtcatatgg ggtttattgg  1080
gaactatcct cctggcccca ccctgcccct tcttttggt tttgacatca ttcatttcca  1140
cctgggaatt tctggtgcca tgccagaaag aatgaggaac ctgtattcct cttcttcgtg  1200
ataatataat ctctattttt ttaggaaaaa aaaaaaaaaa                         1240

<210> SEQ ID NO 5
<211> LENGTH: 273
<212> TYPE: DNA
<213> ORGANISM: Homo sapiens

<400> SEQUENCE: 5
```

```
gtggagaggt gggaccagct caccctctcc cagcgcaagg ggctgaacta tcggtatcac    60
ctgggttgta actgcaagat caagtcctgc tactacctgc cttgctttgt gacttccaag   120
aacgagtgtc tctggaccga catgctctcc aatttcggtt accctggcta ccagtccaaa   180
cactacgcct gcatccggca gaagggcggc tactgcagct ggtaccgagg atgggccccc   240
ccggataaaa gcatcatcaa tgccacagac ccc                                 273
```

<210> SEQ ID NO 6
<211> LENGTH: 121
<212> TYPE: PRT
<213> ORGANISM: Homo sapiens

<400> SEQUENCE: 6

```
Cys Thr Cys Ser Pro Ser His Pro Gln Asp Ala Phe Cys Asn Ser Asp
  1               5                  10                  15

Ile Val Ile Arg Ala Lys Val Val Gly Lys Lys Leu Val Lys Glu Gly
                 20                  25                  30

Pro Phe Gly Thr Leu Val Tyr Thr Ile Lys Gln Met Lys Met Tyr Arg
             35                  40                  45

Gly Phe Thr Lys Met Pro His Val Gln Tyr Ile His Thr Glu Ala Ser
         50                  55                  60

Glu Ser Leu Cys Gly Leu Lys Leu Glu Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn
        115                 120
```

<210> SEQ ID NO 7
<211> LENGTH: 220
<212> TYPE: PRT
<213> ORGANISM: Homo sapiens

<400> SEQUENCE: 7

```
Met Gly Ala Ala Ala Arg Thr Leu Arg Leu Ala Leu Gly Leu Leu Leu
  1               5                  10                  15

Leu Ala Thr Leu Leu Arg Pro Ala Asp Ala Cys Ser Cys Ser Pro Val
                 20                  25                  30

His Pro Gln Gln Ala Phe Cys Asn Ala Asp Val Val Ile Arg Ala Lys
             35                  40                  45

Ala Val Ser Glu Lys Glu Val Asp Ser Gly Asn Asp Ile Tyr Gly Asn
         50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160
```

```
Met Ile Pro Cys Tyr Ile Ser Ser Pro Asp Glu Cys Leu Trp Met Asp
            165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
            210                 215                 220

<210> SEQ ID NO 8
<211> LENGTH: 126
<212> TYPE: PRT
<213> ORGANISM: Homo sapiens

<400> SEQUENCE: 8

Cys Ser Cys Ser Pro Val His Pro Gln Gln Ala Phe Cys Asn Ala Asp
1               5                   10                  15

Val Val Ile Arg Ala Lys Ala Val Ser Glu Lys Glu Val Asp Ser Gly
            20                  25                  30

Asn Asp Ile Tyr Gly Asn Pro Ile Lys Arg Ile Gln Tyr Glu Ile Lys
        35                  40                  45

Gln Ile Lys Met Phe Lys Gly Pro Glu Lys Asp Ile Glu Phe Ile Tyr
    50                  55                  60

Thr Ala Pro Ser Ser Ala Val Cys Gly Val Ser Leu Asp Val Gly Gly
65                  70                  75                  80

Lys Lys Glu Tyr Leu Ile Ala Gly Lys Ala Glu Gly Asp Gly Lys Met
                85                  90                  95

His Ile Thr Leu Cys Asp Phe Ile Val Pro Trp Asp Thr Leu Ser Thr
            100                 105                 110

Thr Gln Lys Lys Ser Leu Asn His Arg Tyr Gln Met Gly Cys
            115                 120                 125

<210> SEQ ID NO 9
<211> LENGTH: 67
<212> TYPE: PRT
<213> ORGANISM: Homo sapiens

<400> SEQUENCE: 9

Cys Lys Ile Lys Ser Cys Tyr Tyr Leu Pro Cys Phe Val Thr Ser Lys
1               5                   10                  15

Asn Glu Cys Leu Trp Thr Asp Met Leu Ser Asn Phe Gly Tyr Pro Gly
            20                  25                  30

Tyr Gln Ser Lys His Tyr Ala Cys Ile Arg Gln Lys Gly Gly Tyr Cys
        35                  40                  45

Ser Trp Tyr Arg Gly Trp Ala Pro Pro Asp Lys Ser Ile Ile Asn Ala
    50                  55                  60

Thr Asp Pro
65

<210> SEQ ID NO 10
<211> LENGTH: 193
<212> TYPE: PRT
<213> ORGANISM: Homo sapiens

<400> SEQUENCE: 10

Cys Ser Cys Ser Pro Val His Pro Gln Gln Ala Phe Cys Asn Ala Asp
1               5                   10                  15

Val Val Ile Arg Ala Lys Ala Val Ser Glu Lys Glu Val Asp Ser Gly
            20                  25                  30
```

Asn Asp Ile Tyr Gly Asn Pro Ile Lys Arg Ile Gln Tyr Glu Ile Lys
            35                  40                  45

Gln Ile Lys Met Phe Lys Gly Pro Glu Lys Asp Ile Glu Phe Ile Tyr
 50                  55                  60

Thr Ala Pro Ser Ser Ala Val Cys Gly Val Ser Leu Asp Val Gly Gly
 65                  70                  75                  80

Lys Lys Glu Tyr Leu Ile Ala Gly Lys Ala Glu Gly Asp Gly Lys Met
                 85                  90                  95

His Ile Thr Leu Cys Asp Phe Ile Val Pro Trp Asp Thr Leu Ser Thr
            100                 105                 110

Thr Gln Lys Lys Ser Leu Asn His Arg Tyr Gln Met Gly Cys Cys Lys
        115                 120                 125

Ile Lys Ser Cys Tyr Tyr Leu Pro Cys Phe Val Thr Ser Lys Asn Glu
    130                 135                 140

Cys Leu Trp Thr Asp Met Leu Ser Asn Phe Gly Tyr Pro Gly Tyr Gln
145                 150                 155                 160

Ser Lys His Tyr Ala Cys Ile Arg Gln Lys Gly Gly Tyr Cys Ser Trp
                165                 170                 175

Tyr Arg Gly Trp Ala Pro Pro Asp Lys Ser Ile Ile Asn Ala Thr Asp
            180                 185                 190

Pro

<210> SEQ ID NO 11
<211> LENGTH: 14
<212> TYPE: PRT
<213> ORGANISM: Homo sapiens

<400> SEQUENCE: 11

Lys Ile Lys Ser Cys Tyr Tyr Leu Pro Cys Phe Val Thr Ser
 1               5                  10

<210> SEQ ID NO 12
<211> LENGTH: 30
<212> TYPE: PRT
<213> ORGANISM: Homo sapiens

<400> SEQUENCE: 12

Lys Asn Glu Cys Leu Trp Thr Asp Met Leu Ser Asn Phe Gly Tyr Pro
 1               5                  10                  15

Gly Tyr Gln Ser Lys His Tyr Ala Cys Ile Arg Gln Lys Gly
            20                  25                  30

<210> SEQ ID NO 13
<211> LENGTH: 22
<212> TYPE: PRT
<213> ORGANISM: Homo sapiens

<400> SEQUENCE: 13

Gly Tyr Cys Ser Trp Tyr Arg Gly Trp Ala Pro Pro Asp Lys Ser Ile
 1               5                  10                  15

Ile Asn Ala Thr Asp Pro
            20

<210> SEQ ID NO 14
<211> LENGTH: 20
<212> TYPE: PRT
<213> ORGANISM: Homo sapiens

<400> SEQUENCE: 14

```
Arg Gly Phe Thr Lys Met Pro His Val Gln Tyr Ile His Thr Glu Ala
1               5                   10                  15

Ser Glu Ser Leu
            20

<210> SEQ ID NO 15
<211> LENGTH: 25
<212> TYPE: DNA
<213> ORGANISM: Homo sapiens

<400> SEQUENCE: 15
cttcgaagca tcagcataag aaact                                          25

<210> SEQ ID NO 16
<211> LENGTH: 20
<212> TYPE: DNA
<213> ORGANISM: Homo sapiens

<400> SEQUENCE: 16
tggtcatcag cccactggat                                                20

<210> SEQ ID NO 17
<211> LENGTH: 23
<212> TYPE: DNA
<213> ORGANISM: Homo sapiens

<400> SEQUENCE: 17
ctctgcaact ccgacatcgt gat                                            23

<210> SEQ ID NO 18
<211> LENGTH: 24
<212> TYPE: DNA
<213> ORGANISM: Homo sapiens

<400> SEQUENCE: 18
cagcaggtac tggtacttgt tgac                                           24

<210> SEQ ID NO 19
<211> LENGTH: 25
<212> TYPE: DNA
<213> ORGANISM: Homo sapiens

<400> SEQUENCE: 19
gttcacccac taatagggaa cgtga                                          25

<210> SEQ ID NO 20
<211> LENGTH: 24
<212> TYPE: DNA
<213> ORGANISM: Homo sapiens

<400> SEQUENCE: 20
gattctgact tagaggcgtt cagt                                           24
```